United States Patent
Witschel et al.

(10) Patent No.: US 6,440,899 B1
(45) Date of Patent: Aug. 27, 2002

(54) CYCLOHEXENONEDIOXOTHIOCHROMANOYL DERIVATIVES

(75) Inventors: Matthias Witschel, Ludwigshafen; Klaus Langemann, Worms; Wolfgang von Deyn; Ulf Misslitz, both of Neustadt; Ernst Baumann, Dudenhofen; Stefan Engel, Nieder-Olm; Guido Mayer, Neustadt; Ulf Neidlein, Mannheim; Oliver Wagner, Ludwigshafen; Roland Götz, Ludwigshafen; Martina Otten, Ludwigshafen; Karl-Otto Westphalen, Speyer; Helmut Walter, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/674,248

(22) PCT Filed: Apr. 22, 1999

(86) PCT No.: PCT/EP99/02703
§ 371 (c)(1),
(2), (4) Date: Oct. 30, 2000

(87) PCT Pub. No.: WO99/57111
PCT Pub. Date: Nov. 11, 1999

(30) Foreign Application Priority Data

Apr. 30, 1998 (DE) .......................... 198 19 290

(51) Int. Cl.$^7$ .......................... A01N 25/26; A01N 43/84; A01N 43/40; A01N 43/56
(52) U.S. Cl. .......................... 504/100; 504/225; 504/242; 504/248; 504/251; 504/271; 504/272; 504/275; 504/280; 504/283; 504/288; 549/5; 549/15; 549/23; 548/247; 548/268.6; 548/311.7; 548/315.1; 548/364.4; 548/525; 548/526; 546/197; 546/202; 546/280.1; 544/145; 544/146; 544/318

(58) Field of Search .......................... 549/5, 15, 23; 548/247, 364.4, 268.6, 311.7, 315.1, 525, 526; 546/197, 202, 280.1; 544/145, 146, 318; 504/242, 225, 248, 251, 271, 272, 275, 280, 283, 288, 100

(56) References Cited

FOREIGN PATENT DOCUMENTS

| DE | 19532311 | 3/1997 |
|----|----------|--------|
| EP | 283 261  | 9/1988 |
| WO | 97/01550 | 1/1997 |
| WO | 97/08164 | 3/1997 |
| WO | 97/30986 | 8/1997 |

OTHER PUBLICATIONS

JP 07/082240 Derwent Abst.
JP 07/196585 Derwent Abst.
JP 0625144 Derwent Abst.

*Primary Examiner*—Amelia Owens
(74) *Attorney, Agent, or Firm*—Keil & Weinkauf

(57) ABSTRACT

Cyclohexenonedioxothiochromanoyl derivatives of the formula I

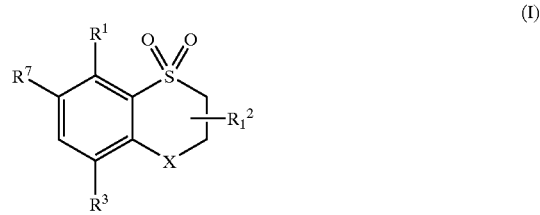

(I)

where
X is oxygen, sulfur, S=O, S(=O)$_2$, CR$^4$R$^5$, C=O or C=NR$^6$, the other substituents are as defined in the specification, and and agriculturally useful salts thereof; processes for preparing the cyclohexenonedioxotheiochromanoyl derivatives; compositions comprising them, and the use of these derivatives or of compositions comprising them for controling undesirable piants.

9 Claims, No Drawings

CYCLOHEXENONEDIOXOTHIOCHROMANOYL DERIVATIVES

The present invention relates to novel cyclohexenonedioxothiochromanoyl derivatives of the formula I, $$\text{[Structure I: benzene ring fused with a 6-membered ring containing S(=O)}_2\text{ and X, bearing substituents } R^1, R^2, R^3, R^7]$$

where:
- X is oxygen, sulfur, S=O, S(=O)$_2$, CR$^4$R$^5$, C=O or C=NR$^6$;
- R$^1$ is hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, aminosulfonyl, N—(C$_1$–C$_6$-alkyl)aminosulfonyl, N,N-di(C$_1$–C$_6$-alkyl)aminosulfonyl, N—(C$_1$–C$_6$-alkylsulfonyl)amino, N—(C$_1$–C$_6$-haloalkylsulfonyl)amino, N—(C$_1$–C$_6$-alkyl)-N—(C$_1$–C$_6$-alkylsulfonyl)amino or N—(C$_1$–C$_6$-alkyl)-N—(C$_1$–C$_6$-haloalkylsulfonyl)amino;
- R$^2$ is C$_1$–C$_6$-alkyl, C$_1$–C$_6$-haloalkyl, C$_1$–C$_6$-alkoxy or C$_1$–C$_6$-haloalkoxy;
- R$^3$ is hydrogen, C$_1$–C$_6$-alkyl or halogen;
- R$^4$, R$^5$ are hydrogen, nitro, halogen, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, N—C$_1$–C$_6$-alkylamino, N—C$_1$–C$_6$-haloalkylamino, N,N-di(C$_1$–C$_6$-alkyl)amino, N—C$_1$–C$_6$-alkoxyamino, N—(C$_1$–C$_6$-alkoxy)-N—(C$_1$–C$_6$-alkyl)amino, 1-tetrahydropyrrolyl, 1-piperidinyl, 4-morpholinyl or 1-hexahydropyrazinyl; or
- R$^4$ and R$^5$ together form an —O—(CH$_2$)$_m$—O—, —O—(CH$_2$)$_m$—S—, —S—(CH$_2$)$_m$—S— or —O—(CH$_2$)$_n$— chain which may be substituted by one to three radicals selected from the following group:
  - halogen, cyano, C$_1$–C$_4$-alkyl, C$_1$–C$_4$-haloalkyl or C$_1$–C$_4$-alkoxycarbonyl; or
- R$^4$ and R$^5$ together form a —(CH$_2$)$_p$— chain which may be interrupted by oxygen or sulfur and/or may be substituted by one to four radicals selected from the following group:
  - halogen, cyano, C$_1$–C$_4$-alkyl, C$_1$–C$_4$-haloalkyl or C$_1$–C$_4$-alkoxycarbonyl; or
- R$^4$ and R$^5$ together form a methylidene group which may be substituted by one or two radicals selected from the following group:
  - halogen, hydroxyl, formyl, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl or C$_1$–C$_6$-haloalkylsulfonyl;
- R$^6$ is C$_1$–C$_6$-alkyl, C$_1$–C$_6$-haloalkyl, C$_1$–C$_6$-alkoxy or C$_1$–C$_6$-haloalkoxy;
- l is 0 to 4;
- m is 2 to 4;
- n is 1 to 5;
- p is 2 to 5;
- R$^7$ is a compound IIa or IIb $$\text{[Structure IIa: cyclohexenone with acyl substituent, bearing (R}^9\text{)}_q \text{ and } R^8\text{]}$$

$$\text{[Structure IIb: cyclohexanedione with exocyclic =CR}^8\text{ group, bearing (R}^9\text{)}_q\text{]}$$

where
- R$^8$ is halogen, OR$^{10}$, SR$^{10}$, SOR$^{11}$, SO$_2$R$^{11}$, OSO$_2$R$^{11}$, POR$^{11}$R$^{12}$, OPOR$^{11}$R$^{12}$, OPSR$^{11}$R$^{12}$, NR$^{13}$R$^{14}$, ONR$^{14}$R$^{14}$, N-bonded heterocyclyl or O—(N-bonded heterocyclyl), where the heterocyclyl radical of the two lastmentioned substituents may be partially or fully halogenated and/or may carry one to three of the following radicals:
  - nitro, cyano, C$_1$–C$_4$-alkyl, C$_1$–C$_4$-haloalkyl, C$_1$–C$_4$-alkoxy or C$_1$–C$_4$-haloalkoxy;
- R$^9$ is nitro, halogen, cyano, C$_1$–C$_6$-alkyl, C$_1$–C$_6$-haloalkyl, di(C$_1$–C$_6$-alkoxy)methyl, di(C$_1$–C$_6$-alkylthio)methyl, (C$_1$–C$_6$-alkoxy)(C$_1$–C$_6$-alkylthio)methyl, hydroxyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl, C$_1$–C$_6$-alkylcarbonyl, C$_1$–C$_6$-haloalkylcarbonyl, C$_1$–C$_6$-alkoxycarbonyl or C$_1$–C$_6$-haloalkoxycarbonyl; or
- two radicals R$^9$ which are attached to the same carbon together form an —O—(CH$_2$)$_m$O—, —O—(CH$_2$)$_m$—S—, —S—(CH$_2$)$_m$—S— or —O—(CH$_2$)$_n$— chain which may be substituted by one to three radicals selected from the following group:
  - halogen, cyano, C$_1$–C$_4$-alkyl, C$_1$–C$_4$-haloalkyl or C$_1$–C$_4$-alkoxycarbonyl; or
- two radicals R$^9$ which are attached to the same carbon together form a —(CH$_2$)$_p$— chain which may be interrupted by oxygen or sulfur and/or may be substituted by one to four radicals selected from the following group:
  - halogen, cyano, C$_1$–C$_4$-alkyl, C$_1$–C$_4$-haloalkyl or C$_1$–C$_4$-alkoxycarbonyl; or
- two radicals R$^9$ which are attached to the same carbon together form a methylidene group which may be substituted by one to two radicals selected from the following group:
  - halogen, hydroxyl, formyl, cyano, C$_1$–C$_6$-alkyl, C$_1$–C$_6$-haloalkyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsulfinyl, C$_1$–C$_6$-alkylsulfonyl, C$_1$–C$_6$-haloalkylsulfonyl; or
- two radicals R$^9$ which are attached to the same carbon together with this carbon form a carbonyl group; or
- two radicals R$^9$ which are attached to different carbons together form a —(CH$_2$)$_n$— chain which may be substituted by one to three radicals selected from the following group:

halogen, $C_1$–$C_6$-alkyl, $C_1$–$C_6$-alkoxy, hydroxyl or $C_1$–$C_6$-alkoxycarbonyl;

$R^{10}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, N-($C_3$–$C_6$-alkynyl)-N—($C_1$–$C_6$-alkoxy)aminocarbonyl, di-($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino) imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N—($C_1$–$C_6$-alkyl)-N-(phenyl)aminocarbonyl, heterocyclylaminocarbonyl, N—($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di-($C_1$–$C_6$-alkyl)amino or di-($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)aminno-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals selected from the following group:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-alkynyl or $C_1$–$C_6$-alkylcarbonyl;

q is 0 to 6 and agriculturally useful salts thereof.

The invention additionally relates to processes for preparing compounds of the formula I, to compositions comprising them and to the use of these derivatives or of compositions comprising them for controlling harmful plants.

Dioxothiochroman derivatives which are linked to a (1-hydroxy-3-oxocyclohex-1-en-2-yl)carbonyl radical with or without substitution are known from the literature, for example from DE-A 19 532 311 and WO 97/08164. However, the herbicidal properties of the prior art compounds and their compatibility with crop plants are not entirely satisfactory.

It is an object of the present invention to provide novel biologically, in particular herbicidally, active ingredients having improved properties.

We have found that this object is achieved by the cyclohexenonedioxothiochromanoyl derivatives of the formula I and their herbicidal action.

Furthermore, the invention provides herbicidal compositions comprising the compounds I and having very good herbicidal activity. Additionally, the invention provides processes for preparing these compositions and methods for controlling undesirable plant growth using the compounds I.

Depending on the substitution pattern, the compounds of the formula I may contain one or more chiral centers and, if this is the case, be present as enantiomers or mixtures of diastereomers. The invention provides both pure enantiomers or diastereomers and mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium, and furthermore phosphonium ions, sulfonium ions, preferably tri($C_1$–$C_4$-alkyl)sulfonium and sulfoxonium ions, preferably tri ($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and also the anions of $C_1$–$C_4$-alkanoic acids, preferably formate, acetate, propionate and butyrate.

The organic molecular moieties mentioned for the substituents $R^1$–$R^{14}$ or as radicals on phenyl and heterocyclyl radicals represent collective terms for individual listings of the individual group members. All hydrocarbon chains, i.e. all alkyl, haloalkyl, alkoxy, haloalkoxy, alkylthio, haloalkylthio, alkylsulfinyl, halo-alkylsulfinyl, alkylsulfonyl, haloalkylsulfonyl, N-alkylaminosulfonyl, N,N-dialkylaminosulfonyl, N-alkylamino, N,N-dialkylamino, N-haloalkylamino, N-alkoxyamino, N-alkoxy-N-alkylamino, N-alkylcarbonylamino, N-alkylsulfonylamino, N-haloalkylsulfonylamino, N-alkyl-N-alkylsulfonylamino, N-alkyl-N-haloalkylsulfonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, dialkoxymethyl, dialkylthiomethyl, (alkoxy)(alkylthio)methyl, alkylcarbonylalkyl, alkoxyiminoalkyl, N-(alkylamino)iminoalkyl, N-(dialkylamino)iminoalkyl, phenylalkenylcarbonyl, heterocyclylalkenylcarbonyl, N-alkoxy-N-alkyl aminocarbonyl, N-alkyl-N-phenylaminocarbonyl, N-alkyl-N-heterocyclylaminocarbonyl, phenylalkyl, heterocyclylalkyl, phenylcarbonylalkyl, heterocyclylcarbonylalkyl, dialkylaminoalkoxycarbonyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy and alkoxyalkoxy moieties may be straight-chain or branched. Unless stated otherwise, halogenated substituents preferably carry one to five identical or different halogen atoms. Halogen is in each case fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkoxyimino-$C_1$–$C_6$-alkyl, N—($C_1$–$C_6$-alkylamino)imino-$C_1$–$C_6$-alkyl, N-(di-$C_1$–$C_6$-alkylamino)imino-$C_1$–$C_6$-alkyl, N—($C_1$–$C_6$-alkoxy)-N—($C_1$–$C_6$-alkyl)aminocarbonyl, N—($C_3$–$C_6$-alkenyl)-N—($C_1$–$C_6$-alkyl)aminocarbonyl, ($C_3$–$C_6$-alkynyl)-N—($C_1$–$C_6$-alkyl)aminocarbonyl, N—($C_1$–$C_6$-alkyl)-N-phenylaminocarbonyl, N—($C_1$–$C_6$-alkyl)-N-heterocyclylaminocarbonyl, phenyl-$C_1$–$C_6$-alkyl, N—($C_1$–$C_6$-alkyl)-N—($C_1$–$C_6$-alkylsulfonyl)amino, N—($C_1$–$C_6$-alkyl)-N—($C_1$–$C_6$-haloalkylsulfonyl)amino, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl, as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N—$C_1$–$C_6$-haloalkylamino: $C_1$–$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N—$C_1$–$C_6$-alkoxyamino, di($C_1$–$C_6$-alkoxy)methyl, ($C_1$–$C_6$-alkoxy)($C_1$–$C_6$-alkylthio)methyl, $C_1$–$C_6$-alkoxyimino-$C_1$–$C_6$-alkyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl and N—($C_3$–$C_6$-alkynyl)-N—($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e. for example fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1-C_6$-haloalkoxy: $C_1-C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1-C_4$-alkylthio: for example methylthio, ethylthio, propylthio, 1-methylethylthio, butylthio, 1-methylpropylthio, 2-methylpropylthio or 1,1-dimethylethylthio;

$C_1-C_6$-alkylthio and the alkylthio moieties of $C_1-C_6$-alkylthiocarbonyl, di-($C_1-C_6$-alkylthio)methyl and ($C_1-C_6$-alkoxy)($C_1-C_6$-alkylthio)methyl: $C_1-C_4$-alkylthio as mentioned above, and also, for example pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1-C_4$-haloalkylthio: a $C_1-C_4$-alkylthio radical as mentioned above which is partially or fully substituted by fluorine, chlorine, bromine and/or iodine, i.e. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1-C_6$-haloalkylthio: $C_1-C_4$-haloalkylthio as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1-C_6$-alkylsulfinyl ($C_1-C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1-C_6$-haloalkylsulfinyl: a $C_1-C_6$-alkylsulfinyl radical as mentioned above which is partially or fully substituted by fluorine, chlorine, bromine and/or iodine, i.e. for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluoro-butylsulfinyl, 5-fluoropentylsulfinyl, 5-chloropentyl-sulfinyl, 5-bromopentylsulfinyl, 5-iodopentylsulfinyl, undecafluoropentylsulfinyl, 6-fluorohexylsulfinyl, 6-chloro-hexylsulfinyl, 6-bromohexylsulfinyl, 6-iodohexylsulfinyl or dodecafluorohexylsulfinyl;

$C_1-C_6$-alkylsulfonyl ($C_1-C_6$-alkyl-S(=O)$_2$—), and the alkylsulfonyl radicals of N—($C_1-C_6$-alkylsulfonyl)amino and N—($C_1-C_6$-alkyl)-N—($C_1-C_6$-alkylsulfonyl)amino: for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkyl radicals of N—($C_1$–$C_6$-haloalkylsulfonyl)amino and N—($C_1$–$C_6$-alkyl)-N—($C_1$–$C_6$-haloalkylsulfonyl)amino: a $C_1$–$C_6$-alkylsulfonyl radical as mentioned above which is partially or fully substituted by fluorine, chlorine, bromine and/or iodine, i.e. for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutyl-sulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N—($C_1$–$C_6$-alkylamino)imino-$C_1$–$C_6$-alkyl, i.e. for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_4$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl or 1,1-dimethylethylaminosulfonyl;

($C_1$–$C_6$-alkylamino)sulfonyl: ($C_1$–$C_4$-alkylamino)sulfonyl as mentioned above, and also, for example, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di($C_1$–$C_4$-alkyl)aminosulfonyl: for example N,N-dimethylaminosulfonyl, N,N-diethylaminosulfonyl, N,N-di(1-methylethyl)aminosulfonyl, N,N-dipropylaminosulfonyl, N,N-dibutylaminosulfonyl, N,N-di(1-methylpropyl)aminosulfonyl, N,N-di(2-methylpropyl)aminosulfonyl, N,N-di(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propylaminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl or N-(1,1-dimethylethyl)-N-(2-methylpropyl)aminosulfonyl;

di($C_1$–$C_6$-alkyl)aminosulfonyl: di-($C_1$–$C_4$-alkyl)aminosulfonyl as mentioned above, and also, for example, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4- methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethylpropyl)aminosulfonyl, N-ethyl-N-(1-ethylpropyl)aminosulfonyl, N-ethyl-N-hexylaminosulfonyl, N-ethyl-N-(1,1-dimethylpropyl)aminosulfonyl, N-ethyl-N-(1,2-dimethylpropyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-dimethylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethylpropyl)aminosulfonyl, N-ethyl-N-(1-ethyl-1-methylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di($C_1$–$C_4$-alkyl)amino, and the dialkylamino radicals of di($C_1$–$C_4$-alkyl)amino-$C_1$–$C_4$-alkoxycarbonyl and N-(di-$C_1$–$C_4$-alkylamino)imino-$C_1$–$C_6$-alkyl, for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino, and the dialkylamino radicals of di($C_1$–$C_6$-alkyl)aminoimino-$C_1$–$C_6$-alkyl: di-($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of $C_1$–$C_6$-alkylcarbonylamino, $C_1$–$C_6$-alkylcarbonyl-$C_1$–$C_6$-alkyl: $C_1$–$C_4$-alkylcarbonyl as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethyl-propylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl as mentioned above, and also heptylcarbonyl, octylcarbonyl, pentadecylcarbonyl or heptadecylcarbonyl;

$C_1$–$C_6$-haloalkylcarbonyl: a $C_1$–$C_6$-alkylcarbonyl radical as mentioned above which is partially or fully substituted by fluorine, chlorine, bromine and/or iodine, i.e. for example chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-difluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, 5-fluoropentylcarbonyl, 5-chloropentylcarbonyl, 5-bromopentylcarbonyl, perfluoropentylcarbonyl, 6-fluorohexylcarbonyl, 6-chlorohexylcarbonyl, 6-bromohexylcarbonyl or perfluorohexylcarbonyl;

$C_1$–$C_4$-alkoxycarbonyl, and the alkoxycarbonyl moieties of di($C_1$–$C_4$-alkyl)amino-$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl: ($C_1$–$C_4$-alkoxy)carbonyl as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethyl-butoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_6$-haloalkoxycarbonyl: a $C_1$–$C_4$-alkoxycarbonyl radical as mentioned above which is partially or fully substituted by fluorine, chlorine, bromine and/or iodine, for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl, 4-iodobutoxycarbonyl, 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, Hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di($C_1$–$C_4$-alkyl)aminocarbonyl: for example N,N-dimethylaminocarbonyl, N,N-diethylaminocarbonyl, N,N-di(1-methylethyl)aminocarbonyl, N,N-dipropylaminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl) aminocarbonyl;

di($C_1$–$C_6$-alkyl)aminocarbonyl: di-($C_1$–$C_4$-alkyl) aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl- N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-propyl-N-pentylaminocarbonyl, N-butyl-N-pentylaminocarbonyl, N,N-dipentylaminocarbonyl, N-propyl-N-hexylaminocarbonyl, N-butyl-N-hexylaminocarbonyl, N-pentyl-N-hexylaminocarbonyl or N,N-dihexylaminocarbonyl;

di($C_1$–$C_6$-alkyl)aminothiocarbonyl: for example N,N-dimethylaminothiocarbonyl, N,N-diethylaminothiocarbonyl, N,N-di(1-methylethyl)aminothiocarbonyl, N,N-dipropylaminothiocarbonyl, N,N-dibutylaminothiocarbonyl, N,N-di(1-methylpropyl)aminothiocarbonyl, N,N-di(2-methylpropyl)aminothiocarbonyl, N,N-di(1,1-dimethylethyl)aminothiocarbonyl, N-ethyl-N-methylaminothiocarbonyl, N-methyl-N-propylaminothiocarbonyl, N-methyl-N-(1-methylethyl)aminothiocarbonyl, N-butyl-N-methylaminothiocarbonyl, N-methyl-N-(1-methylpropyl)aminothiocarbonyl, N-methyl-N-(2-methylpropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-methylpropyl) aminothiocarbonyl, N-ethyl-N-(1,1-dimethylethyl) aminothiocarbonyl, N-(1-methylethyl)-N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1-methylethyl)aminothiocarbonyl, N-(1-methylethyl)-N-(1-methylpropyl)aminothiocarbonyl, N-(1-methylethyl)-N-(2-methylpropyl)aminothiocarbonyl, N-(1,1-dimethylethyl)-N-(1-methylethyl)aminothiocarbonyl, N-butyl-N-(1-methylpropyl)aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl)aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethylpropyl)aminothiocarbonyl, N-methyl-N-(1,2-dimethylpropyl)aminothiocarbonyl, N-methyl-N-(1-methylpentyl)aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl)aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1- ethyl-1-methylpropyl)aminothiocarbonyl, N-ethyl-N-(1-ethyl-2-methylpropyl)aminothiocarbonyl, N-propyl-N-pentylaminothiocarbonyl, N-butyl-N-pentylaminothiocarbonyl, N,N-dipentylaminothiocarbonyl, N-propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy, and the alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N—($C_3$–$C_6$-alkenyl)-N—($C_1$–$C_6$-alkyl)aminocarbonyl, N—($C_3$–$C_6$-alkenyl)-N—($C_1$–$C_6$-alkoxy)aminocarbonyl: for example prop-2-en-1-yl, but-1-en-4-yl, 1-methylprop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-en-1-yl, 2-ethylbut-2-en-1-yl, 2-ethylbut-3-en-1-yl, 1,1,2-trimethylprop2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkynyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)-N—($C_1$–$C_6$-alkyl)aminocarbonyl, N—($C_{36}$-alkynyl)-N—($C_1$–$C_6$-alkoxy)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$-alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclylcarbonyl, heterocyclyl-$C_1$–$C_6$-alkyl, heterocyclyloxycarbonyl, heterocyclyloxythiocarbonyl, heterocyclylcarbonyl-$C_1$–$C_6$-alkyl, N—($C_1$–$C_6$-alkyl)-N-(heterocyclyl) aminocarbonyl, heterocyclylaminocarbonyl: a saturated, partially saturated or unsaturated 5- or 6-membered heterocyclic ring which is attached via carbon and contains one to four identical or different heteroatoms selected from the following group: oxygen, sulfur or nitrogen, i.e., for example, 5-membered rings having one heteroatom:
  tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having 2 heteroatoms such as:
  tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxa-zol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings having 3 heteroatoms such as: 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having 4 heteroatoms such as: tetrazol-5-yl, 6-membered rings having one heteroatom such as:
  tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin- 2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-di-hydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings having two heteroatoms such as:

1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered rings having 3 heteroatoms such as: 1,3,5-triazin-2-yl, 1,2,4-triazin-3-yl, 1,2,4-triazin-5-yl or 1,2,4-triazin-6-yl;

6-membered rings having 4 heteroatoms such as: 1,2,4,5-tetrazin-3-yl;

where, if appropriate, the sulfur of the abovementioned heterocycles may be oxidized to S=O or S(=O)$_2$ and where a bicyclic ring system may be formed with a fused-on phenyl ring or with a $C_3$–$C_6$-carbocycle or with a further 5- or 6-membered heterocycle.

N-bonded heterocyclyl: a saturated, partially saturated or unsaturated 5- or 6-membered N-bonded heterocyclic ring which contains at least one nitrogen and, if appropriate, one to three identical or different heteroatoms selected from the following group: oxygen, sulphur or nitrogen, i.e., for example, N-bonded 5-membered rings such as:
tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydroisothiazol-2-yl, tetrahydroimidazol-1-yl, tetrahydroooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl, imidazol-1-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl, 1,2,3-triazol-1-yl, 1,2,4-triazol-1-yl, tetrazol-1-yl;

and also N-bonded 6-membered rings such as:
piperidin-1-yl, 1,2,3,4-tetrahydropyridin-1-yl, 1,2,5,6-tetrahydropyridin-1-yl, 1,4-dihydropyridin-1-yl, 1,2-dihydropyridin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazinoxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl, and also N-bonded cyclic imides such as: phthalimide, tetrahydrophthalimide, succinimide, maleimide or glutarimide.

All phenyl rings or heterocyclyl radicals and also all phenyl components in phenyl-$C_1$–$C_6$-alkyl, phenylcarbonyl-$C_1$–$C_6$-alkyl, phenylcarbonyl, phenylalkenylcarbonyl, phenoxycarbonyl, phenylaminocarbonyl and N—($C_1$–$C_6$-alkyl)-N-phenylaminocarbonyl or heterocyclyl components in heterocyclyl-$C_1$–$C_6$-alkyl, heterocyclylcarbonyl-$C_1$–$C_6$-alkyl, heterocyclylcarbonyl, heterocyclylalkenylcarbonyl, heterocyclyloxycarbonyl, heterocyclylaminocarbonyl and N—($C_1$–$C_6$-alkyl)-N-heterocyclylaminocarbonyl, are, unless stated otherwise, preferably unsubstituted or carry one to three halogen atoms and/or a nitro group, a cyano radical and/or one or two methyl, trifluoromethyl, methoxy or trifluoromethoxy substituents.

The compounds of the formula I according to the invention where $R^7$=IIa are designated as compounds of the formula Ia, and the compounds of the formula I where $R^7$=IIb are designated as Ib.

With respect to the use of the compounds of the formula I according to the invention as herbicides, the variables preferably have the meanings below, in each case on their own or in combination:

X is S(=O)$_2$ or $CR^4R^5$;

$R^1$ is nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl;

$R^3$ is hydrogen;

$R^4$, $R^5$ are hydrogen, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl; or $R^4$ and $R^5$ together form an —O—$(CH_2)_m$—O—, —O—$(CH_2)_m$—S—, —S—$(CH_2)_m$—S— or —O—$(CH_2)_n$— chain which may be substituted by one to three radicals selected from the following group:
halogen, cyano, $C_1$–$C_4$-alkyl, $C_1$–$C_4$-haloalkyl or $C_1$–$C_4$-alkoxycarbonyl; or $R^4$ and $R^5$ together form a —$(CH_2)_p$— chain which may be interrupted by oxygen or sulfur and/or may carry one to four radicals selected from the following group:
halogen, cyano, $C_1$–$C_4$-alkyl, $C_1$–$C_4$-haloalkyl or $C_1$–$C_4$-alkoxycarbonyl; or $R^4$ and $R^5$ together form a methylidene group which may be substituted by one to two radicals selected from the following group:
halogen, cyano, $C_1$–$C_6$alkyl, $C_1$–$C_6$-haloalkyl, $C_1$–$C_6$-alkoxy or $C_1$–$C_6$-haloalkoxy;

l is 0;

m is 2 to 4;

n is 1 to 5;

p is 2 to 5;

$R^7$ is a compound IIa or IIb

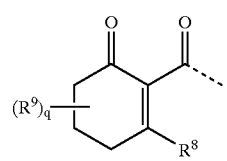

IIa

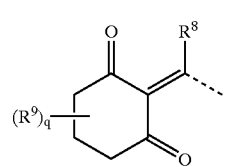

IIb where
$R^8$ is halogen, $OR^{10}$, $SR^{10}$, $SO_2R^{11}$, $OSO_2R^{11}$, $OPOR^{11}R^{12}$, $OPSR^{11}R^{12}$, $NR^{13}R^{14}$, $ONR^{14}R^{14}$, N-bonded heterocyclyl or O—(N-bonded heterocyclyl), where the heterocyclyl radical of the two lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl; or two radicals $R^9$ which are attached to the same carbon together form an —O—$(CH_2)_m$—O—, —O—$(CH_2)_m$—S—, —S—$(CH_2)_m$—S— or —O—$(CH_2)_n$— chain which may be substituted by one to three radicals selected from the following group:
halogen, cyano, $C_1$–$C_4$-alkyl, $C_1$–$C_4$-haloalkyl or $C_1$–$C_4$-alkoxycarbonyl; or two radicals $R^9$ which are attached to the same carbon together form a —$(CH_2)_p$— chain which may be interrupted by oxygen or sulfur and/or may be substituted by one to four radicals selected from the following group:
halogen, cyano, $C_1$–$C_4$-alkyl, $C_1$–$C_4$-haloalkyl or $C_1$–$C_4$-alkoxycarbonyl; or two radicals $R^9$ which are attached to the same carbon together with this carbon form a carbonyl group; or two radicals $R^9$ which are attached to different carbons together form a —$(CH_2)_n$— chain which may be substituted by one to three radicals selected from the following group:
halogen, $C_1$–$C_6$-alkyl, $C_1$–$C_6$-alkoxy, hydroxyl or $C_1$–$C_6$-alkoxycarbonyl;

$R^{10}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, N—($C_3$–$C_6$-alkynyl)-N—($C_1$–$C_6$-alkoxy)aminocarbonyl, di-($C_1$–$C_6$-alkyl)aminothiocarbonyl, $C_1$–$C_6$-alkyl-carbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl or N,N-di-($C_1$–$C_6$-alkylamino)imino-$C_1$–$C_6$-alkyl, where the above-mentioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenyl-$C_2$–$C_6$-alkenylcarbonyl or heterocyclyl-$C_2$–$C_6$-alkenylcarbonyl, where the phenyl and the heterocyclyl radical of the 14 lastmentioned substituents may be partially or fully halogenated and/or may carry one to three of the following radicals: nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl, $C_3$–$C_6$-alkenyl, $C_3$–$C_6$-haloalkenyl, $C_{3-6}$cycloalkyl, hydroxyl, $C_1$–$C_6$-alkoxy or di-($C_1$–$C_6$-haloalkyl)amino, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals selected from the following group: cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl or $C_3$–$C_6$-alkenyl;

q 0 to 6.

Particular preference is given to compounds of the formula I, where the variables have the following meanings, in each case on their own or in combination:

X is S(=O)$_2$ or $CR^4R^5$, $R^1$ is halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl;
in particular halogen such as chlorine or bromine, $C_1$–$C_6$-alkyl such as methyl or ethyl or $C_1$–$C_6$-alkoxy such as methoxy or ethoxy;
particularly preferably chlorine, methyl or methoxy;

$R^3$ is hydrogen;

$R^4$, $R^5$ are hydrogen, $C_1$–$C_6$-alkyl, $C_1$–$C_6$-haloalkyl, $C_1$–$C_6$-alkoxy or $C_1$–$C_6$-haloalkoxy,
in particular hydrogen, $C_1$–$C_6$-alkyl or $C_1$–$C_6$-alkoxy;
particularly preferably hydrogen or $C_1$–$C_6$-alkyl such as methyl or ethyl; or $R^4$ and $R^5$ together form an —O—$(CH_2)_m$—O—, —O—$(CH_2)_m$—S— or —S—$(CH_2)_m$—S— chain, which may be substituted by one to three radicals selected from the following group: $C_1$–$C_4$-alkyl or $C_1$–$C_4$-haloalkyl; or $R^4$ and $R^5$ together form a —$(CH_2)_p$— chain which may be substituted by one to four radicals selected from the following group:
halogen, $C_1$–$C_4$-alkyl or $C_1$–$C_4$-haloalkyl; or $R^4$ and $R^5$ together form a methylidene group which may be substituted by one to two radicals selected from the following group:
halogen, cyano, $C_1$–$C_6$-alkyl, $C_1$–$C_6$-haloalkyl, $C_1$–$C_6$-alkoxy or $C_1$–$C_6$-haloalkoxy;

l is 0;
m is 2 to 4; in particular 2 or 3
p is 2 to 5;
$R^7$ is a compound IIa or IIb

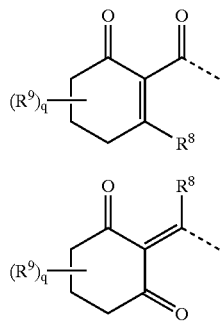

where
$R^8$ is halogen, $OR^{10}$, $SR^{10}$, $SO_2R^{11}$, $OSO_2R^{11}$, $NR^{13}R^{14}$, $ONR^{14}R^{14}$, N-bonded heterocyclyl or O—(N-bonded heterocyclyl), where the heterocyclyl radical of the two lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkylthio or $C_1$–$C_6$-haloalkylthio, or two radicals $R^9$ which are attached to the same carbon together with this carbon form a carbonyl group;

$R^{10}$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_3$–$C_6$-cycloalkylcarbonyl, $C_1$–$C_6$-alkoxycarbonyl, $C_3$–$C_6$-alkenyloxycarbonyl, $C_1$–$C_6$-alkylaminocarbonyl, $C_3$–$C_6$-alkenylaminocarbonyl, N,N-di-($C_1$–$C_6$-alkyl)aminocarbonyl, N—($C_3$–$C_6$-alkenyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, di-($C_1$–$C_6$-alkyl)aminothiocarbonyl or $C_1$–$C_6$-alkylcarbonyl-$C_1$–$C_6$-alkyl, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl or heterocyclyloxythiocarbonyl, where the phenyl and the heterocyclyl radical of the 12 lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy or di-($C_1$–$C_6$-haloalkyl)amino, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals selected from the following group:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl or $C_3$–$C_6$-alkenyl;
q is 0 to 6.

Particular preference is given to compounds of the formula I, where
$R^4$ is hydrogen, $C_1$–$C_6$-alkyl, $C_1$–$C_6$-haloalkyl, $C_1$–$C_6$-alkoxy or $C_1$–$C_6$-haloalkoxy;
particularly preferably hydrogen, $C_1$–$C_6$-alkyl such as methyl or ethyl or $C_1$–$C_6$-alkoxy such as methoxy or ethoxy;

$R^5$ is hydrogen or $C_1$–$C_6$-alkyl; particularly preferably hydrogen or methyl; or $R^4$ and $R^5$ together form an —O—$(CH_2)_2$—O—, —O—$(CH_2)_3$—O—, —O—$(CH_2)_2$—S—, —O—$(CH_2)_3$—S—, —S—$(CH_2)_2$—S—, —S—$(CH_2)_3$—S—, —$(CH_2)_2$—, —$(CH_2)_4$— or —$(CH_2)_5$— chain which may be substituted by one to three $C_1$–$C_4$-alkyl or $C_1$–$C_4$-haloalkyl radicals; or R$^4$ and R$^5$ together form a methylidene group which may be substituted by a radical selected from the following group:
- halogen such as chlorine or bromine, C$_1$–C$_6$-alkyl such as methyl or ethyl, C$_1$–C$_6$-haloalkyl such as chloromethyl, fluoromethyl, dichloromethyl, difluoromethyl or trifluoromethyl, C$_1$–C$_6$-alkoxy such as methoxy or ethoxy.

Very particular preference is given to the compounds of the formula I, where
- R$^4$ is hydrogen, C$_1$–C$_6$-alkyl, C$_1$–C$_6$-haloalkyl, C$_1$–C$_6$-alkoxy or C$_1$–C$_6$-haloalkoxy;
  - particularly preferably hydrogen, C$_1$–C$_6$-alkyl such as methyl or ethyl or C$_1$–C$_6$-alkoxy such as methoxy or ethoxy;
- R$^5$ is hydrogen or C$_1$–C$_6$-alkyl;
  - particularly preferably hydrogen or methyl.

Likewise, particular preference is given to compounds of the formula I, where
- R$^9$ is nitro, halogen, cyano, C$_1$–C$_6$-alkyl, C$_1$–C$_6$-haloalkyl, di-(C$_1$–C$_6$-alkoxy)methyl, di-(C$_1$–C$_6$-alkylthio)methyl, (C$_1$–C$_6$-alkoxy)(C$_1$–C$_6$-alkylthio)methyl, hydroxyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsufinyl, C$_1$–C$_6$-alkylsulfonyl, C$_1$–C$_6$-haloalkylsulfonyl, C$_1$–C$_6$-alkylcarbonyl, C$_1$–C$_6$-haloalkylcarbonyl, C$_1$–C$_6$-alkoxycarbonyl or C$_1$–C$_6$-haloalkoxycarbonyl; or
- two radicals R$^9$ which are attached to the same carbon together form an —O—(CH$_2$)$_m$—O—, —O—(CH$_2$)$_m$—S—, —S—(CH$_2$)$_m$—S— or —O—(CH$_2$)$_n$— chain which may be substituted by one to three radicals selected from the following group:
  - halogen, cyano, C$_1$–C$_4$-alkyl, C$_1$–C$_4$-haloalkyl or C$_1$–C$_4$-alkoxycarbonyl; or
- two radicals R$^9$ which are attached to the same carbon form a —(CH$_2$)$_p$— chain which may be interrupted by oxygen or sulfur and/or may be substituted by one to four radicals selected from the following group:
  - halogen, cyano, C$_1$–C$_4$-alkyl, C$_1$–C$_4$-haloalkyl or C$_1$–C$_4$-alkoxycarbonyl; or
- two radicals R$^9$ which are attached to the same carbon together with this carbon form a carbonyl group.

Very particular preference is given to compounds of the formula I, where
- R$^9$ is nitro, halogen, cyano, C$_1$–C$_6$-alkyl, C$_1$–C$_6$-haloalkyl, di-(C$_1$–C$_6$-alkoxy)methyl, di-(C$_1$–C$_6$-alkylthio)methyl, (C$_1$–C$_6$-alkoxy)(C$_1$–C$_6$-alkylthio)methyl, hydroxyl, C$_1$–C$_6$-alkoxy, C$_1$–C$_6$-haloalkoxy, C$_1$–C$_6$-alkylthio, C$_1$–C$_6$-haloalkylthio, C$_1$–C$_6$-alkylsulfinyl, C$_1$–C$_6$-haloalkylsufinyl, C$_1$–C$_6$-alkylsulfonyl, C$_1$–C$_6$-haloalkylsulfonyl, C$_1$–C$_6$-alkylcarbonyl, C$_1$–C$_6$-haloalkylcarbonyl, C$_1$–C$_6$-alkoxycarbonyl or C$_1$–C$_6$-haloalkoxycarbonyl; or
- two radicals R$^9$ which are attached to the same carbon together with this carbon form a carbonyl group.

Likewise, particular preference is given to the compounds of the formula I, where
- R$^8$ is NR$^{13}$R$^{14}$ or N-bonded heterocyclyl which may be partially or fully halogenated and/or may carry one to three of the following radicals:
  - nitro, cyano, C$_1$–C$_4$-alkyl, C$_1$–C$_4$-haloalkyl, C$_1$–C$_4$-alkoxy or C$_1$–C$_4$-haloalkoxy.

Likewise, particular preference is given to the compounds of the formula I, where
- R$^8$ is SR$^{10}$, NR$^{13}$R$^{14}$ or N-bonded heterocyclyl, where the heterocyclyl radical may be partially or fully halogenated and/or may carry one to three of the following radicals:
  - nitro, cyano, C$_1$–C$_4$-alkyl, C$_1$–C$_4$-haloalkyl, C$_1$–C$_4$-alkoxy or C$_1$–C$_4$-haloalkoxy.

Very particular preference is given to compounds of the formula I, where
- R$^8$ is NR$^{13}$R$^{14}$ or tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydrothiazol-2-yl, tetrahydroimidazol-1-yl, tetrahydrooxazol-3-yl, tetrahydrothiazol-3-yl, pyrazol-1-yl, imidazol-1-yl, 1,2,4-triazol-1-yl, tetrazol-1-yl, piperidin-1-yl, hexahydropyrimidin-1-yl, hexahydropyrazin-1-yl, tetrahydro-1,4-oxazin-4-yl, tetrahydro-1,2-oxazin-2-yl, succinimide, maleinimide or glutarimide, where the abovementioned heterocycles may be partially or fully halogenated and/or may carry one to three of the following radicals:
  - nitro, cyano, C$_1$–C$_4$-alkyl, such as methyl or ethyl, C$_1$–C$_4$-haloalkyl such as chloromethyl, difluoromethyl or trifluoromethyl, C$_1$–C$_4$-alkoxy such as methoxy or ethoxy or C$_1$–C$_4$-haloalkoxy such as difluoromethoxy or trifluoromethoxy.

Very particular preference is furthermore given to the compounds of the formula Ia.

Likewise, very particular preference is given to the compounds of the formula Ia where the variables are as defined below, in each case on their own or in combination:
- X is S(=O)$_2$ or CR$^4$R$^5$;
- R$^1$ is halogen or C$_1$–C$_6$-alkyl;
  - in particular chlorine, bromine or C$_1$–C$_4$-alkyl;
  - particularly preferably chlorine or methyl;
- R$^3$ is hydrogen;
- R$^4$ is hydrogen, C$_1$–C$_6$-alkyl or C$_1$–C$_6$-alkoxy;
  - in particular C$_1$–C$_6$-alkyl or C$_1$–C$_6$-alkoxy;
  - particularly preferably methyl or methoxy;
- R$^5$ is hydrogen or C$_1$–C$_6$-alkyl;
  - in particular hydrogen or methyl;
- 1 [sic] is O;
- R$^8$ is halogen, OR$^{10}$, SR$^{10}$, SO$_2$R$^{11}$, NR$^{13}$R$^{14}$ or N-bonded heterocyclyl, where the heterocyclyl radical may be partially or fully halogenated and/or may carry one to three of the following radicals:
  - nitro, cyano, C$_1$–C$_4$-alkyl, C$_1$–C$_4$-haloalkyl, C$_1$–C$_4$-alkoxy or C$_1$–C$_4$-haloalkoxy;
- R$^9$ is C$_1$–C$_6$-alkyl, such as methyl or ethyl;
  - in particular methyl; or
- two radicals R$^9$ which are attached to the same carbon form, together with this carbon, a carbonyl group;
- R$^{10}$ is C$_1$–C$_6$-alkyl, C$_3$–C$_6$-alkenyl or C$_3$–C$_6$-haloalkenyl, where the alkyl radical may be partially or fully halogenated and/or may carry one to three of the following groups:
  - C$_1$–C$_4$-alkoxy, C$_1$–C$_4$-alkylcarbonyl or C$_1$–C$_4$-alkoxycarbonyl;
  - phenyl, heterocyclyl, phenyl-C$_1$–C$_6$-alkyl, heterocyclyl-C$_1$–C$_6$-alkyl or phenylcarbonyl, where the five lastmentioned radicals may be partially or fully halogenated and/or may carry one to three of the following radicals:
    - nitro, C$_1$–C$_4$-alkyl, C$_1$–C$_4$-haloalkyl or C$_1$–C$_4$-alkoxy;
- R$^{11}$ is C$_1$–C$_6$-alkyl, C$_3$–C$_6$-alkenyl or C$_3$–C$_6$-haloalkenyl, where the alkyl radical may be partially or fully halogenated and/or may carry one to three of the following groups:
  - C$_1$–C$_4$-alkoxy, C$_1$–C$_4$-alkylcarbonyl or C$_1$–C$_4$-alkoxycarbonyl;

phenyl, heterocyclyl, phenyl-$C_1$–$C_6$-alkyl, heterocyclyl-$C_1$–$C_6$-alkyl or phenylcarbonyl, where the five lastmentioned radicals may be partially or fully halogenated and/or may carry one to three of the following radicals:

nitro, $C_1$–$C_4$-alkyl, $C_1$–$C_4$-haloalkyl or $C_1$–$C_4$-alkoxy; in particular $C_1$–$C_6$-alkyl or phenyl which may be partially or fully halogenated;

$R^{13}$ is $C_1$–$C_6$-alkyl, such as methyl or ethyl;

$R^{14}$ is $C_1$–$C_6$-alkoxy, such as methoxy or ethoxy;

q is from 0 to 6.

Particular preference is given to the compounds of the formula Ia where:

$R^8$ is halogen, $OR^{10}$, $SR^{10}$, $SO_2R^{11}$, $NR^{13}R^{14}$, 4-morpholinyl, 2-tetrahydroisoxazolyl, 1-pyrrolidinyl or 1-(1,2,4-triazolyl).

Extraordinary preference is given to the compounds of the formula Ia1 and Ib1 (=I where X=$CR^4R^5$ and l, q=0), in particular to the compounds Ia1.1 to Ia1.342 and the compounds Ib1.1 to Ib1.342, where the radical definitions $R^1$ to $R^9$, l and q not only in combination with one another, but in each case also on their own, have a particular meaning for the compounds according to the invention.

TABLE 1

Ia1

Ib1

| No. | $R^1$ | $R^3$ | $R^4$ | $R^5$ | $R^8$ |
|---|---|---|---|---|---|
| Ia1.1 or Ib1.1 | $CH_3$ | H | H | H | F |
| Ia1.2 or Ib1.2 | $CH_3$ | H | H | H | Cl |
| Ia1.3 or Ib1.3 | $CH_3$ | H | H | H | Br |
| Ia1.4 or Ib1.4 | $CH_3$ | H | H | H | I |
| Ia1.5 or Ib1.5 | $CH_3$ | H | H | H | $SO_2CH_3$ |
| Ia1.6 or Ib1.6 | $CH_3$ | H | H | H | $SO_2CH_2CH_3$ |
| Ia1.7 or Ib1.7 | $CH_3$ | H | H | H | $SC_6H_5$ |
| Ia1.8 or Ib1.8 | $CH_3$ | H | H | H | $S(4\text{-}CH_3\text{—}C_6H_4)$ |
| Ia1.9 or Ib1.9 | $CH_3$ | H | H | H | $S(4\text{-}Cl\text{—}C_6H_4)$ |
| Ia1.10 or Ib1.10 | $CH_3$ | H | H | H | $SO_2C_6H_5$ |
| Ia1.11 or Ib1.11 | $CH_3$ | H | H | H | $SO_2(4\text{-}CH_3\text{—}C_6H_4)$ |
| Ia1.12 or Ib1.12 | $CH_3$ | H | H | H | $SO_2(4\text{-}Cl\text{—}C_6H_4)$ |
| Ia1.13 or Ib1.13 | $CH_3$ | H | H | H | 4-morpholinyl |
| Ia1.14 or Ib1.14 | $CH_3$ | H | H | H | 1-pyrrolidinyl |
| Ia1.15 or Ib1.15 | $CH_3$ | H | H | H | 1-(1,2,4-triazolyl) |
| Ia1.16 or Ib1.16 | $CH_3$ | H | H | H | 1-imidazolyl |
| Ia1.17 or Ib1.17 | $CH_3$ | H | H | H | $N(OCH_3)CH_3$ |
| Ia1.18 or Ib1.18 | $CH_3$ | H | H | H | 2-tetrahydroisoxazolyl |
| Ia1.19 or Ib1.19 | $CH_3$ | H | H | H | $N(CH_3)N(CH_3)_2$ |
| Ia1.20 or Ib1.20 | $CH_3$ | H | H | H | $N(CH_2CH\text{=}CH_2)N(CH_3)_2$ |
| Ia1.21 or Ib1.21 | $CH_3$ | H | H | H | $OPO(OCH_3)_2$ |
| Ia1.22 or Ib1.22 | $CH_3$ | H | H | H | $OPO(OCH_2CH_3)_2$ |
| Ia1.23 or Ib1.23 | $CH_3$ | H | H | H | $OPO(OC_6H_5)_2$ |
| Ia1.24 or Ib1.24 | $CH_3$ | H | H | H | $OPO(CH_3)_2$ |
| Ia1.25 or Ib1.25 | $CH_3$ | H | H | H | $OPO(CH_2CH_3)_2$ |
| Ia1.26 or Ib1.26 | $CH_3$ | H | H | H | $OPO(C_6H_5)_2$ |
| Ia1.27 or Ib1.27 | $CH_3$ | H | H | H | $OPS(OCH_3)_2$ |
| Ia1.28 or Ib1.28 | $CH_3$ | H | H | H | $OPS(OCH_2CH_3)_2$ |
| Ia1.29 or Ib1.29 | $CH_3$ | H | H | H | $PO(OCH_3)_2$ |
| Ia1.30 or Ib1.30 | $CH_3$ | H | H | H | $PO(OCH_2CH_3)_2$ |
| Ia1.31 or Ib1.31 | $CH_3$ | H | H | H | $PO(C_6H_5)_2$ |
| Ia1.32 or Ib1.32 | $CH_3$ | H | H | H | $OCH_2C_6H_5$ |
| Ia1.33 or Ib1.33 | $CH_3$ | H | H | H | $OCH_2(2\text{-furyl})$ |
| Ia1.34 or Ib1.34 | $CH_3$ | H | H | H | $OCH_2(3\text{-furyl})$ |
| Ia1.35 or Ib1.35 | $CH_3$ | H | H | H | $OCOOCH_3$ |
| Ia1.36 or Ib1.36 | $CH_3$ | H | H | H | $OCOOCH_2CH_3$ |
| Ia1.37 or Ib1.37 | $CH_3$ | H | H | H | $OCOOCH(CH_3)_2$ |
| Ia1.38 or Ib1.38 | $CH_3$ | H | H | H | $OCOOC_6H_5$ |
| Ia1.39 or Ib1.39 | $CH_3$ | H | H | H | $OCOOC(CH_3)_3$ |

TABLE 1-continued

Ia1

Ib1

| No. | R¹ | R³ | R⁴ | R⁵ | R⁸ |
|---|---|---|---|---|---|
| Ia1.40 or Ib1.40 | CH₃ | H | H | H | OCSOC₆H₅ |
| Ia1.41 or Ib1.41 | CH₃ | H | H | H | OCSN(CH₃)₂ |
| Ia1.42 or Ib1.42 | CH₃ | H | H | H | OCON(CH₃)₂ |
| Ia1.43 or Ib1.43 | CH₃ | H | H | H | OCOSCH₃ |
| Ia1.44 or Ib1.44 | CH₃ | H | H | H | ON(CH₃)₂ |
| Ia1.45 or Ib1.45 | CH₃ | H | H | H | O-1-piperidyl |
| Ia1.46 or Ib1.46 | CH₃ | H | H | H | OCO(CH₂)₆CH₃ |
| Ia1.47 or Ib1.47 | CH₃ | H | H | H | OCO(CH₂)₇CH₃ |
| Ia1.48 or Ib1.48 | CH₃ | H | H | H | OCO(CH₂)₁₆CH₃ |
| Ia1.49 or Ib1.49 | CH₃ | H | H | H | OCO(CH₂)₁₄CH₃ |
| Ia1.50 or Ib1.50 | CH₃ | H | H | H | OCOCH₂CH₂CH=CH₂ |
| Ia1.51 or Ib1.51 | CH₃ | H | H | H | OCOcyclopropyl |
| Ia1.52 or Ib1.52 | CH₃ | H | H | H | OCOcyclopentyl |
| Ia1.53 or Ib1.53 | CH₃ | H | H | H | OCOcyclohexyl |
| Ia1.54 or Ib1.54 | CH₃ | H | H | H | OCO(2-tetrahydrofuryl) |
| Ia1.55 or Ib1.55 | CH₃ | H | H | H | OCO(2-furyl) |
| Ia1.56 or Ib1.56 | CH₃ | H | H | H | OCO(2-thienyl) |
| Ia1.57 or Ib1.57 | CH₃ | H | H | H | OCO(3-pyridyl) |
| Ia1.58 or Ib1.58 | CH₃ | H | CH₃ | H | F |
| Ia1.59 or Ib1.59 | CH₃ | H | CH₃ | H | Cl |
| Ia1.60 or Ib1.60 | CH₃ | H | CH₃ | H | Br |
| Ia1.61 or Ib1.61 | CH₃ | H | CH₃ | H | I |
| Ia1.62 or Ib1.62 | CH₃ | H | CH₃ | H | SO₂CH₃ |
| Ia1.63 or Ib1.63 | CH₃ | H | CH₃ | H | SO₂CH₂CH₃ |
| Ia1.64 or Ib1.64 | CH₃ | H | CH₃ | H | SC₆H₅ |
| Ia1.65 or Ib1.65 | CH₃ | H | CH₃ | H | S(4-CH₃—C₆H₄) |
| Ia1.66 or Ib1.66 | CH₃ | H | CH₃ | H | S(4-Cl—C₆H₄) |
| Ia1.67 or Ib1.67 | CH₃ | H | CH₃ | H | SO₂C₆H₅ |
| Ia1.68 or Ib1.68 | CH₃ | H | CH₃ | H | SO₂(4-CH₃—C₆H₄) |
| Ia1.69 or Ib1.69 | CH₃ | H | CH₃ | H | SO₂(4-Cl—C₆H₄) |
| Ia1.70 or Ib1.70 | CH₃ | H | CH₃ | H | 4-morpholinyl |
| Ia1.71 or Ib1.71 | CH₃ | H | CH₃ | H | 1-pyrrolidinyl |
| Ia1.72 or Ib1.72 | CH₃ | H | CH₃ | H | 1-(1,2,4-triazolyl) |
| Ia1.73 or Ib1.73 | CH₃ | H | CH₃ | H | 1-imidazolyl |
| Ia1.74 or Ib1.74 | CH₃ | H | CH₃ | H | N(OCH₃)CH₃ |
| Ia1.75 or Ib1.75 | CH₃ | H | CH₃ | H | 2-tetrahydroisoxazolyl |
| Ia1.76 or Ib1.76 | CH₃ | H | CH₃ | H | N(CH₃)N(CH₃)₂ |
| Ia1.77 or Ib1.77 | CH₃ | H | CH₃ | H | N(CH₂CH=CH₂)N(CH₃)₂ |
| Ia1.78 or Ib1.78 | CH₃ | H | CH₃ | H | OPO(OCH₃)₂ |
| Ia1.79 or Ib1.79 | CH₃ | H | CH₃ | H | OPO(OCH₂CH₃)₂ |
| Ia1.80 or Ib1.80 | CH₃ | H | CH₃ | H | OPO(OC₆H₅)₂ |
| Ia1.81 or Ib1.81 | CH₃ | H | CH₃ | H | OPO(CH₃)₂ |
| Ia1.82 or Ib1.82 | CH₃ | H | CH₃ | H | OPO(CH₂CH₃)₂ |
| Ia1.83 or Ib1.83 | CH₃ | H | CH₃ | H | OPO(C₆H₅)₂ |
| Ia1.84 or Ib1.84 | CH₃ | H | CH₃ | H | OPS(OCH₃)₂ |
| Ia1.85 or Ib1.85 | CH₃ | H | CH₃ | H | OPS(OCH₂CH₃)₂ |
| Ia1.86 or Ib1.86 | CH₃ | H | CH₃ | H | PO(OCH₃)₂ |
| Ia1.87 or Ib1.87 | CH₃ | H | CH₃ | H | PO(OCH₂CH₃)₂ |
| Ia1.88 or Ib1.88 | CH₃ | H | CH₃ | H | PO(C₆H₅)₂ |
| Ia1.89 or Ib1.89 | CH₃ | H | CH₃ | H | OCH₂C₆H₅ |
| Ia1.90 or Ib1.90 | CH₃ | H | CH₃ | H | OCH₂(2-furyl) |
| Ia1.91 or Ib1.91 | CH₃ | H | CH₃ | H | OCH₂(3-furyl) |
| Ia1.92 or Ib1.92 | CH₃ | H | CH₃ | H | OCOOCH₃ |
| Ia1.93 or Ib1.93 | CH₃ | H | CH₃ | H | OCOOCH₂CH₃ |

TABLE 1-continued

Ia1

Ib1

| No. | R¹ | R³ | R⁴ | R⁵ | R⁸ |
|---|---|---|---|---|---|
| Ia1.94 or Ib1.94 | CH₃ | H | CH₃ | H | OCOOCH(CH₃)₂ |
| Ia1.95 or Ib1.95 | CH₃ | H | CH₃ | H | OCOOC₆H₅ |
| Ia1.96 or Ib1.96 | CH₃ | H | CH₃ | H | OCOOC(CH₃)₃ |
| Ia1.97 or Ib1.97 | CH₃ | H | CH₃ | H | OCSOC₆H₅ |
| Ia1.98 or Ib1.98 | CH₃ | H | CH₃ | H | OCSN(CH₃)₂ |
| Ia1.99 or Ib1.99 | CH₃ | H | CH₃ | H | OCON(CH₃)₂ |
| Ia1.100 or Ib1.100 | CH₃ | H | CH₃ | H | OCOSCH₃ |
| Ia1.101 or Ib1.101 | CH₃ | H | CH₃ | H | ON(CH₃)₂ |
| Ia1.102 or Ib1.102 | CH₃ | H | CH₃ | H | O-1-piperidyl |
| Ia1.103 or Ib1.103 | CH₃ | H | CH₃ | H | OCO(CH₂)₆CH₃ |
| Ia1.104 or Ib1.104 | CH₃ | H | CH₃ | H | OCO(CH₂)₇CH₃ |
| Ia1.105 or Ib1.105 | CH₃ | H | CH₃ | H | OCO(CH₂)₁₆CH₃ |
| Ia1.106 or Ib1.106 | CH₃ | H | CH₃ | H | OCO(CH₂)₁₄CH₃ |
| Ia1.107 or Ib1.107 | CH₃ | H | CH₃ | H | OCOCH₂CH₂CH=CH₂ |
| Ia1.108 or Ib1.108 | CH₃ | H | CH₃ | H | OCOcyclopropyl |
| Ia1.109 or Ib1.109 | CH₃ | H | CH₃ | H | OCOcyclopentyl |
| Ia1.110 or Ib1.110 | CH₃ | H | CH₃ | H | OCOcyclohexyl |
| Ia1.111 or Ib1.111 | CH₃ | H | CH₃ | H | OCO(2-tetrahydrofuryl) |
| Ia1.112 or Ib1.112 | CH₃ | H | CH₃ | H | OCO(2-furyl) |
| Ia1.113 or Ib1.113 | CH₃ | H | CH₃ | H | OCO(2-thienyl) |
| Ia1.114 or Ib1.114 | CH₃ | H | CH₃ | H | OCO(3-pyridyl) |
| Ia1.115 or Ib1.115 | CH₃ | H | CH₃ | CH₃ | F |
| Ia1.116 or Ib1.116 | CH₃ | H | CH₃ | CH₃ | Cl |
| Ia1.117 or Ib1.117 | CH₃ | H | CH₃ | CH₃ | Br |
| Ia1.118 or Ib1.118 | CH₃ | H | CH₃ | CH₃ | I |
| Ia1.119 or Ib1.119 | CH₃ | H | CH₃ | CH₃ | SO₂CH₃ |
| Ia1.120 or Ib1.120 | CH₃ | H | CH₃ | CH₃ | SO₂CH₂CH₃ |
| Ia1.121 or Ib1.121 | CH₃ | H | CH₃ | CH₃ | SC₆H₅ |
| Ia1.122 or Ib1.122 | CH₃ | H | CH₃ | CH₃ | S(4-CH₃—C₆H₄) |
| Ia1.123 or Ib1.123 | CH₃ | H | CH₃ | CH₃ | S(4-Cl—C₆H₄) |
| Ia1.124 or Ib1.124 | CH₃ | H | CH₃ | CH₃ | SO₂C₆H₅ |
| Ia1.125 or Ib1.125 | CH₃ | H | CH₃ | CH₃ | SO₂(4-CH₃—C₆H₄) |
| Ia1.126 or Ib1.126 | CH₃ | H | CH₃ | CH₃ | SO₂(4-Cl—C₆H₄) |
| Ia1.127 or Ib1.127 | CH₃ | H | CH₃ | CH₃ | 4-morpholinyl |
| Ia1.128 or Ib1.128 | CH₃ | H | CH₃ | CH₃ | 1-pyrrolidinyl |
| Ia1.129 or Ib1.129 | CH₃ | H | CH₃ | CH₃ | 1-(1,2,4-triazolyl) |
| Ia1.130 or Ib1.130 | CH₃ | H | CH₃ | CH₃ | 1-imidazolyl |
| Ia1.131 or Ib1.131 | CH₃ | H | CH₃ | CH₃ | N(OCH₃)CH₃ |
| Ia1.132 or Ib1.132 | CH₃ | H | CH₃ | CH₃ | 2-tetrahydroisoxazolyl |
| Ia1.133 or Ib1.133 | CH₃ | H | CH₃ | CH₃ | N(CH₃)N(CH₃)₂ |
| Ia1.134 or Ib1.134 | CH₃ | H | CH₃ | CH₃ | N(CH₂CH=CH₂)N(CH₃)₂ |
| Ia1.135 or Ib1.135 | CH₃ | H | CH₃ | CH₃ | OPO(OCH₃)₂ |
| Ia1.136 or Ib1.136 | CH₃ | H | CH₃ | CH₃ | OPO(OCH₂CH₃)₂ |
| Ia1.137 or Ib1.137 | CH₃ | H | CH₃ | CH₃ | OPO(OC₆H₅)₂ |
| Ia1.138 or Ib1.138 | CH₃ | H | CH₃ | CH₃ | OPO(CH₃)₂ |
| Ia1.139 or Ib1.139 | CH₃ | H | CH₃ | CH₃ | OPO(CH₂CH₃)₂ |
| Ia1.140 or Ib1.140 | CH₃ | H | CH₃ | CH₃ | OPO(C₆H₅)₂ |
| Ia1.141 or Ib1.141 | CH₃ | H | CH₃ | CH₃ | OPS(OCH₃)₂ |
| Ia1.142 or Ib1.142 | CH₃ | H | CH₃ | CH₃ | OPS(OCH₂CH₃)₂ |
| Ia1.143 or Ib1.143 | CH₃ | H | CH₃ | CH₃ | PO(OCH₃)₂ |
| Ia1.144 or Ib1.144 | CH₃ | H | CH₃ | CH₃ | PO(OCH₂CH₃)₂ |
| Ia1.145 or Ib1.145 | CH₃ | H | CH₃ | CH₃ | PO(C₆H₅)₂ |
| Ia1.146 or Ib1.146 | CH₃ | H | CH₃ | CH₃ | OCH₂C₆H₅ |
| Ia1.147 or Ib1.147 | CH₃ | H | CH₃ | CH₃ | OCH₂(2-furyl) |

TABLE 1-continued

Ia1

Ib1

| No. | R¹ | R³ | R⁴ | R⁵ | R⁸ |
|---|---|---|---|---|---|
| Ia1.148 or Ib1.148 | CH₃ | H | CH₃ | CH₃ | OCH₂(3-furyl) |
| Ia1.149 or Ib1.149 | CH₃ | H | CH₃ | CH₃ | OCOOCH₃ |
| Ia1.150 or Ib1.150 | CH₃ | H | CH₃ | CH₃ | OCOOCH₂CH₃ |
| Ia1.151 or Ib1.151 | CH₃ | H | CH₃ | CH₃ | OCOOCH(CH₃)₂ |
| Ia1.152 or Ib1.152 | CH₃ | H | CH₃ | CH₃ | OCOOC₆H₅ |
| Ia1.153 or Ib1.153 | CH₃ | H | CH₃ | CH₃ | OCOOC(CH₃)₃ |
| Ia1.154 or Ib1.154 | CH₃ | H | CH₃ | CH₃ | OCSOC₆H₅ |
| Ia1.155 or Ib1.155 | CH₃ | H | CH₃ | CH₃ | OCSN(CH₃)₂ |
| Ia1.156 or Ib1.156 | CH₃ | H | CH₃ | CH₃ | OCON(CH₃)₂ |
| Ia1.157 or Ib1.157 | CH₃ | H | CH₃ | CH₃ | OCOSCH₃ |
| Ia1.158 or Ib1.158 | CH₃ | H | CH₃ | CH₃ | ON(CH₃)₂ |
| Ia1.159 or Ib1.159 | CH₃ | H | CH₃ | CH₃ | O-1-piperidyl |
| Ia1.160 or Ib1.160 | CH₃ | H | CH₃ | CH₃ | OCO(CH₂)₆CH₃ |
| Ia1.161 or Ib1.161 | CH₃ | H | CH₃ | CH₃ | OCO(CH₂)₇CH₃ |
| Ia1.162 or Ib1.162 | CH₃ | H | CH₃ | CH₃ | OCO(CH₂)₁₆CH₃ |
| Ia1.163 or Ib1.163 | CH₃ | H | CH₃ | CH₃ | OCO(CH₂)₁₄CH₃ |
| Ia1.164 or Ib1.164 | CH₃ | H | CH₃ | CH₃ | OCOCH₂CH₂CH=CH₂ |
| Ia1.165 or Ib1.165 | CH₃ | H | CH₃ | CH₃ | OCOcyclopropyl |
| Ia1.166 or Ib1.166 | CH₃ | H | CH₃ | CH₃ | OCOcyclopentyl |
| Ia1.167 or Ib1.167 | CH₃ | H | CH₃ | CH₃ | OCOcyclohexyl |
| Ia1.168 or Ib1.168 | CH₃ | H | CH₃ | CH₃ | OCO(2-tetrahydrofuryl) |
| Ia1.169 or Ib1.169 | CH₃ | H | CH₃ | CH₃ | OCO(2-furyl) |
| Ia1.170 or Ib1.170 | CH₃ | H | CH₃ | CH₃ | OCO(2-thienyl) |
| Ia1.171 or Ib1.171 | CH₃ | H | CH₃ | CH₃ | OCO(3-pyridyl) |
| Ia1.172 or Ib1.172 | Cl | H | H | H | F |
| Ia1.173 or Ib1.173 | Cl | H | H | H | Cl |
| Ia1.174 or Ib1.174 | Cl | H | H | H | Br |
| Ia1.175 or Ib1.175 | Cl | H | H | H | I |
| Ia1.176 or Ib1.176 | Cl | H | H | H | SO₂CH₃ |
| Ia1.177 or Ib1.177 | Cl | H | H | H | SO₂CH₂CH₃ |
| Ia1.178 or Ib1.178 | Cl | H | H | H | SC₆H₅ |
| Ia1.179 or Ib1.179 | Cl | H | H | H | S(4-CH₃—C₆H₄) |
| Ia1.180 or Ib1.180 | Cl | H | H | H | S(4-Cl—C₆H₄) |
| Ia1.181 or Ib1.181 | Cl | H | H | H | SO₂C₆H₅ |
| Ia1.182 or Ib1.182 | Cl | H | H | H | SO₂(4-CH₃—C₆H₄) |
| Ia1.183 or Ib1.183 | Cl | H | H | H | SO₂(4-Cl—C₆H₄) |
| Ia1.184 or Ib1.184 | Cl | H | H | H | 4-morpholinyl |
| Ia1.185 or Ib1.185 | Cl | H | H | H | 1-pyrrolidinyl |
| Ia1.186 or Ib1.186 | Cl | H | H | H | 1-(1,2,4-triazolyl) |
| Ia1.187 or Ib1.187 | Cl | H | H | H | 1-imidazolyl |
| Ia1.188 or Ib1.188 | Cl | H | H | H | N(OCH₃)CH₃ |
| Ia1.189 or Ib1.189 | Cl | H | H | H | 2-tetrahydroisoxazolyl |
| Ia1.190 or Ib1.190 | Cl | H | H | H | N(CH₃)N(CH₃)₂ |
| Ia1.191 or Ib1.191 | Cl | H | H | H | N(CH₂CH=CH₂)N(CH₃)₂ |
| Ia1.192 or Ib1.192 | Cl | H | H | H | OPO(OCH₃)₂ |
| Ia1.193 or Ib1.193 | Cl | H | H | H | OPO(OCH₂CH₃)₂ |
| Ia1.194 or Ib1.194 | Cl | H | H | H | OPO(OC₆H₅)₂ |
| Ia1.195 or Ib1.195 | Cl | H | H | H | OPO(CH₃)₂ |
| Ia1.196 or Ib1.196 | Cl | H | H | H | OPO(CH₂CH₃)₂ |
| Ia1.197 or Ib1.197 | Cl | H | H | H | OPO(C₆H₅)₂ |
| Ia1.198 or Ib1.198 | Cl | H | H | H | OPS(OCH₃)₂ |
| Ia1.199 or Ib1.199 | Cl | H | H | H | OPS(OCH₂CH₃)₂ |
| Ia1.200 or Ib1.200 | Cl | H | H | H | PO(OCH₃)₂ |
| Ia1.201 or Ib1.201 | Cl | H | H | H | PO(OCH₂CH₃)₂ |

TABLE 1-continued

Ia1

Ib1

| No. | R¹ | R³ | R⁴ | R⁵ | R⁸ |
|---|---|---|---|---|---|
| Ia1.202 or Ib1.202 | Cl | H | H | H | PO(C$_6$H$_5$)$_2$ |
| Ia1.203 or Ib1.203 | Cl | H | H | H | OCH$_2$C$_6$H$_5$ |
| Ia1.204 or Ib1.204 | Cl | H | H | H | OCH$_2$(2-furyl) |
| Ia1.205 or Ib1.205 | Cl | H | H | H | OCH$_2$(3-furyl) |
| Ia1.206 or Ib1.206 | Cl | H | H | H | OCOOCH$_3$ |
| Ia1.207 or Ib1.207 | Cl | H | H | H | OCOOCH$_2$CH$_3$ |
| Ia1.208 or Ib1.208 | Cl | H | H | H | OCOOCH(CH$_3$)$_2$ |
| Ia1.209 or Ib1.209 | Cl | H | H | H | OCOOC$_6$H$_5$ |
| Ia1.210 or Ib1.210 | Cl | H | H | H | OCOOC(CH$_3$)$_3$ |
| Ia1.211 or Ib1.211 | Cl | H | H | H | OCSOC$_6$H$_5$ |
| Ia1.212 or Ib1.212 | Cl | H | H | H | OCSN(CH$_3$)$_2$ |
| Ia1.213 or Ib1.213 | Cl | H | H | H | OCON(CH$_3$)$_2$ |
| Ia1.214 or Ib1.214 | Cl | H | H | H | OCOSCH$_3$ |
| Ia1.215 or Ib1.215 | Cl | H | H | H | ON(CH$_3$)$_2$ |
| Ia1.216 or Ib1.216 | Cl | H | H | H | O-1-piperidyl |
| Ia1.217 or Ib1.217 | Cl | H | H | H | OCO(CH$_2$)$_6$CH$_3$ |
| Ia1.218 or Ib1.218 | Cl | H | H | H | OCO(CH$_2$)$_7$CH$_3$ |
| Ia1.219 or Ib1.219 | Cl | H | H | H | OCO(CH$_2$)$_{16}$CH$_3$ |
| Ia1.220 or Ib1.220 | Cl | H | H | H | OCO(CH$_2$)$_{14}$CH$_3$ |
| Ia1.221 or Ib1.221 | Cl | H | H | H | OCOCH$_2$CH$_2$CH=CH$_2$ |
| Ia1.222 or Ib1.222 | Cl | H | H | H | OCOcyclopropyl |
| Ia1.223 or Ib1.223 | Cl | H | H | H | OCOcyclopentyl |
| Ia1.224 or Ib1.224 | Cl | H | H | H | OCOcyclohexyl |
| Ia1.225 or Ib1.225 | Cl | H | H | H | OCO(2-tetrahydrofuryl) |
| Ia1.226 or Ib1.226 | Cl | H | H | H | OCO(2-furyl) |
| Ia1.227 or Ib1.227 | Cl | H | H | H | OCO(2-thienyl) |
| Ia1.228 or Ib1.228 | Cl | H | H | H | OCO(3-pyridyl) |
| Ia1.229 or Ib1.229 | Cl | H | CH$_3$ | H | F |
| Ia1.230 or Ib1.230 | Cl | H | CH$_3$ | H | Cl |
| Ia1.231 or Ib1.231 | Cl | H | CH$_3$ | H | Br |
| Ia1.232 or Ib1.232 | Cl | H | CH$_3$ | H | I |
| Ia1.233 or Ib1.233 | Cl | H | CH$_3$ | H | SO$_2$CH$_3$ |
| Ia1.234 or Ib1.234 | Cl | H | CH$_3$ | H | SO$_2$CH$_2$CH$_3$ |
| Ia1.235 or Ib1.235 | Cl | H | CH$_3$ | H | SC$_6$H$_5$ |
| Ia1.236 or Ib1.236 | Cl | H | CH$_3$ | H | S(4-CH$_3$—C$_6$H$_4$) |
| Ia1.237 or Ib1.237 | Cl | H | CH$_3$ | H | S(4-Cl—C$_6$H$_4$) |
| Ia1.238 or Ib1.238 | Cl | H | CH$_3$ | H | SO$_2$C$_6$H$_5$ |
| Ia1.239 or Ib1.239 | Cl | H | CH$_3$ | H | SO$_2$(4-CH$_3$—C$_6$H$_4$) |
| Ia1.240 or Ib1.240 | Cl | H | CH$_3$ | H | SO$_2$(4-Cl—C$_6$H$_4$) |
| Ia1.241 or Ib1.241 | Cl | H | CH$_3$ | H | 4-morpholinyl |
| Ia1.242 or Ib1.242 | Cl | H | CH$_3$ | H | 1-pyrrolidinyl |
| Ia1.243 or Ib1.243 | Cl | H | CH$_3$ | H | 1-(1,2,4-triazolyl) |
| Ia1.244 or Ib1.244 | Cl | H | CH$_3$ | H | 1-imidazolyl |
| Ia1.245 or Ib1.245 | Cl | H | CH$_3$ | H | N(OCH$_3$)CH$_3$ |
| Ia1.246 or Ib1.246 | Cl | H | CH$_3$ | H | 2-tetrahydroisoxazolyl |
| Ia1.247 or Ib1.247 | Cl | H | CH$_3$ | H | N(CH$_3$)N(CH$_3$)$_3$ |
| Ia1.248 or Ib1.248 | Cl | H | CH$_3$ | H | N(CH$_2$CH=CH$_2$)N(CH$_3$)$_2$ |
| Ia1.249 or Ib1.249 | Cl | H | CH$_3$ | H | OPO(OCH$_3$)$_2$ |
| Ia1.250 or Ib1.250 | Cl | H | CH$_3$ | H | OPO(OCH$_2$CH$_3$)$_2$ |
| Ia1.251 or Ib1.251 | Cl | H | CH$_3$ | H | OPO(OC$_6$H$_5$)$_2$ |
| Ia1.252 or Ib1.252 | Cl | H | CH$_3$ | H | OPO(CH$_3$)$_2$ |
| Ia1.253 or Ib1.253 | Cl | H | CH$_3$ | H | OPO(CH$_2$CH$_3$)$_2$ |
| Ia1.254 or Ib1.254 | Cl | H | CH$_3$ | H | OPO(C$_6$H$_5$)$_2$ |
| Ia1.255 or Ib1.255 | Cl | H | CH$_3$ | H | OPS(OCH$_3$)$_2$ |

TABLE 1-continued

Ia1

Ib1

| No. | R$^1$ | R$^3$ | R$^4$ | R$^5$ | R$^8$ |
|---|---|---|---|---|---|
| Ia1.256 or Ib1.256 | Cl | H | CH$_3$ | H | OPS(OCH$_2$CH$_3$)$_2$ |
| Ia1.257 or Ib1.257 | Cl | H | CH$_3$ | H | PO(OCH$_3$)$_2$ |
| Ia1.258 or Ib1.258 | Cl | H | CH$_3$ | H | PO(OCH$_2$CH$_3$)$_2$ |
| Ia1.259 or Ib1.259 | Cl | H | CH$_3$ | H | PO(C$_6$H$_5$)$_2$ |
| Ia1.260 or Ib1.260 | Cl | H | CH$_3$ | H | OCH$_2$C$_6$H$_5$ |
| Ia1.261 or Ib1.261 | Cl | H | CH$_3$ | H | OCH$_2$(2-furyl) |
| Ia1.262 or Ib1.262 | Cl | H | CH$_3$ | H | OCH$_2$(3-furyl) |
| Ia1.263 or Ib1.263 | Cl | H | CH$_3$ | H | OCOOCH$_3$ |
| Ia1.264 or Ib1.264 | Cl | H | CH$_3$ | H | OCOOCH$_2$CH$_3$ |
| Ia1.265 or Ib1.265 | Cl | H | CH$_3$ | H | OCOOCH(CH$_3$)$_2$ |
| Ia1.266 or Ib1.266 | Cl | H | CH$_3$ | H | OCOOC$_6$H$_5$ |
| Ia1.267 or Ib1.267 | Cl | H | CH$_3$ | H | OCOOC(CH$_3$)$_3$ |
| Ia1.268 or Ib1.268 | Cl | H | CH$_3$ | H | OCSOC$_6$H$_5$ |
| Ia1.269 or Ib1.269 | Cl | H | CH$_3$ | H | OCSN(CH$_3$)$_2$ |
| Ia1.270 or Ib1.270 | Cl | H | CH$_3$ | H | OCON(CH$_3$)$_2$ |
| Ia1.271 or Ib1.271 | Cl | H | CH$_3$ | H | OCOSCH$_3$ |
| Ia1.272 or Ib1.272 | Cl | H | CH$_3$ | H | ON(CH$_3$)$_2$ |
| Ia1.273 or Ib1.273 | Cl | H | CH$_3$ | H | O-1-piperidyl |
| Ia1.274 or Ib1.274 | Cl | H | CH$_3$ | H | OCO(CH$_2$)$_6$CH$_3$ |
| Ia1.275 or Ib1.275 | Cl | H | CH$_3$ | H | OCO(CH$_2$)$_7$CH$_3$ |
| Ia1.276 or Ib1.276 | Cl | H | CH$_3$ | H | OCO(CH$_2$)$_{16}$CH$_3$ |
| Ia1.277 or Ib1.277 | Cl | H | CH$_3$ | H | OCO(CH$_2$)$_{14}$CH$_3$ |
| Ia1.278 or Ib1.278 | Cl | H | CH$_3$ | H | OCOCH$_2$CH$_2$CH=CH$_2$ |
| Ia1.279 or Ib1.279 | Cl | H | CH$_3$ | H | OCOcyclopropyl |
| Ia1.280 or Ib1.280 | Cl | H | CH$_3$ | H | OCOcyclopentyl |
| Ia1.281 or Ib1.281 | Cl | H | CH$_3$ | H | OCOcyclohexyl |
| Ia1.282 or Ib1.282 | Cl | H | CH$_3$ | H | OCO(2-tetrahydrofuryl) |
| Ia1.283 or Ib1.283 | Cl | H | CH$_3$ | H | OCO(2-furyl) |
| Ia1.284 or Ib1.284 | Cl | H | CH$_3$ | H | OCO(2-thienyl) |
| Ia1.285 or Ib1.285 | Cl | H | CH$_3$ | H | OCO(3-pyridyl) |
| Ia1.286 or Ib1.286 | Cl | H | CH$_3$ | CH$_3$ | F |
| Ia1.287 or Ib1.287 | Cl | H | CH$_3$ | CH$_3$ | Cl |
| Ia1.288 or Ib1.288 | Cl | H | CH$_3$ | CH$_3$ | Br |
| Ia1.289 or Ib1.289 | Cl | H | CH$_3$ | CH$_3$ | I |
| Ia1.290 or Ib1.290 | Cl | H | CH$_3$ | CH$_3$ | SO$_2$CH$_3$ |
| Ia1.291 or Ib1.291 | Cl | H | CH$_3$ | CH$_3$ | SO$_2$CH$_2$CH$_3$ |
| Ia1.292 or Ib1.292 | Cl | H | CH$_3$ | CH$_3$ | SC$_6$H$_5$ |
| Ia1.293 or Ib1.293 | Cl | H | CH$_3$ | CH$_3$ | S(4-CH$_3$—C$_6$H$_4$) |
| Ia1.294 or Ib1.294 | Cl | H | CH$_3$ | CH$_3$ | S(4-Cl—C$_6$H$_4$) |
| Ia1.295 or Ib1.295 | Cl | H | CH$_3$ | CH$_3$ | SO$_2$C$_6$H$_5$ |
| Ia1.296 or Ib1.296 | Cl | H | CH$_3$ | CH$_3$ | SO$_2$(4-CH$_3$—C$_6$H$_4$) |
| Ia1.297 or Ib1.297 | Cl | H | CH$_3$ | CH$_3$ | SO$_2$(4-Cl—C$_6$H$_4$) |
| Ia1.298 or Ib1.298 | Cl | H | CH$_3$ | CH$_3$ | 4-morpholinyl |
| Ia1.299 or Ib1.299 | Cl | H | CH$_3$ | CH$_3$ | 1-pyrrolidinyl |
| Ia1.300 or Ib1.300 | Cl | H | CH$_3$ | CH$_3$ | 1-(1,2,4-triazolyl) |
| Ia1.301 or Ib1.301 | Cl | H | CH$_3$ | CH$_3$ | 1-imidazolyl |
| Ia1.302 or Ib1.302 | Cl | H | CH$_3$ | CH$_3$ | N(OCH$_3$)CH$_3$ |
| Ia1.303 or Ib1.303 | Cl | H | CH$_3$ | CH$_3$ | 2-tetrahydroisoxazolyl |

TABLE 1-continued

Ia1

Ib1

| No. | $R^1$ | $R^3$ | $R^4$ | $R^5$ | $R^8$ |
|---|---|---|---|---|---|
| Ia1.304 or Ib1.304 | Cl | H | $CH_3$ | $CH_3$ | $N(CH_3)N(CH_3)_2$ |
| Ia1.305 or Ib1.305 | Cl | H | $CH_3$ | $CH_3$ | $N(CH_2CH=CH_2)N(CH_3)_2$ |
| Ia1.306 or Ib1.306 | Cl | H | $CH_3$ | $CH_3$ | $OPO(OCH_3)_2$ |
| Ia1.307 or Ib1.307 | Cl | H | $CH_3$ | $CH_3$ | $OPO(OCH_2CH_3)_2$ |
| Ia1.308 or Ib1.308 | Cl | H | $CH_3$ | $CH_3$ | $OPO(OC_6H_5)_2$ |
| Ia1.309 or Ib1.309 | Cl | H | $CH_3$ | $CH_3$ | $OPO(CH_3)_2$ |
| Ia1.310 or Ib1.310 | Cl | H | $CH_3$ | $CH_3$ | $OPO(CH_2CH_3)_2$ |
| Ia1.311 or Ib1.311 | Cl | H | $CH_3$ | $CH_3$ | $OPO(C_6H_5)_2$ |
| Ia1.312 or Ib1.312 | Cl | H | $CH_3$ | $CH_3$ | $OPS(OCH_3)_2$ |
| Ia1.313 or Ib1.313 | Cl | H | $CH_3$ | $CH_3$ | $OPS(OCH_2CH_3)_2$ |
| Ia1.314 or Ib1.314 | Cl | H | $CH_3$ | $CH_3$ | $PO(OCH_3)_2$ |
| Ia1.315 or Ib1.315 | Cl | H | $CH_3$ | $CH_3$ | $PO(OCH_2CH_3)_2$ |
| Ia1.316 or Ib1.316 | Cl | H | $CH_3$ | $CH_3$ | $PO(C_6H_5)_2$ |
| Ia1.317 or Ib1.317 | Cl | H | $CH_3$ | $CH_3$ | $OCH_2C_6H_5$ |
| Ia1.318 or Ib1.318 | Cl | H | $CH_3$ | $CH_3$ | $OCH_2$(2-furyl) |
| Ia1.319 or Ib1.319 | Cl | H | $CH_3$ | $CH_3$ | $OCH_2$(3-furyl) |
| Ia1.320 or Ib1.320 | Cl | H | $CH_3$ | $CH_3$ | $OCOOCH_3$ |
| Ia1.321 or Ib1.321 | Cl | H | $CH_3$ | $CH_3$ | $OCOOCH_2CH_3$ |
| Ia1.322 or Ib1.322 | Cl | H | $CH_3$ | $CH_3$ | $OCOOCH(CH_3)_2$ |
| Ia1.323 or Ib1.323 | Cl | H | $CH_3$ | $CH_3$ | $OCOC_6H_5$ |
| Ia1.324 or Ib1.324 | Cl | H | $CH_3$ | $CH_3$ | $OCOOC(CH_3)_3$ |
| Ia1.325 or Ib1.325 | Cl | H | $CH_3$ | $CH_3$ | $OCSOC_6H_5$ |
| Ia1.326 or Ib1.326 | Cl | H | $CH_3$ | $CH_3$ | $OCSN(CH_3)_2$ |
| Ia1.327 or Ib1.327 | Cl | H | $CH_3$ | $CH_3$ | $OCON(CH_3)_2$ |
| Ia1.328 or Ib1.328 | Cl | H | $CH_3$ | $CH_3$ | $OCOSCH_3$ |
| Ia1.329 or Ib1.329 | Cl | H | $CH_3$ | $CH_3$ | $ON(CH_3)_2$ |
| Ia1.330 or Ib1.330 | Cl | H | $CH_3$ | $CH_3$ | O-1-piperidyl |
| Ia1.331 or Ib1.331 | Cl | H | $CH_3$ | $CH_3$ | $OCO(CH_2)_6CH_3$ |
| Ia1.332 or Ib1.332 | Cl | H | $CH_3$ | $CH_3$ | $OCO(CH_2)_7CH_3$ |
| Ia1.333 or Ib1.333 | Cl | H | $CH_3$ | $CH_3$ | $OCO(CH_2)_{16}CH_3$ |
| Ia1.334 or Ib1.334 | Cl | H | $CH_3$ | $CH_3$ | $OCO(CH_2)_{14}CH_3$ |
| Ia1.335 or Ib1.335 | Cl | H | $CH_3$ | $CH_3$ | $OCOCH_2CH_2CH=CH_2$ |
| Ia1.336 or Ib1.336 | Cl | H | $CH_3$ | $CH_3$ | OCOcyclopropyl |
| Ia1.337 or Ib1.337 | Cl | H | $CH_3$ | $CH_3$ | OCOcyclopentyl |
| Ia1.338 or Ib1.338 | Cl | H | $CH_3$ | $CH_3$ | OCOcyclohexyl |
| Ia1.339 or Ib1.339 | Cl | H | $CH_3$ | $CH_3$ | OCO(2-tetrahydrofuryl) |
| Ia1.340 or Ib1.340 | Cl | H | $CH_3$ | $CH_3$ | OCO(2-furyl) |
| Ia1.341 or Ib1.341 | Cl | H | $CH_3$ | $CH_3$ | OCO(2-thienyl) |
| Ia1.342 or Ib1.342 | Cl | H | $CH_3$ | $CH_3$ | OCO(3-pyridyl) |

Furthermore, extraordinary preference is given to the following cyclohexenonedioxothiochromanoyl derivatives of the formula I:

The compounds of the formulae Ia2 and Ib2, in particular the compounds Ia2.1 to Ia2.342 and the compounds Ib2.1 to Ib2.342 which differ from the compounds Ia1.1 to Ia1.342 and Ib1.1 to Ib1.342, respectively, in that $(R^9)_q$ is "5,5-dimethyl".

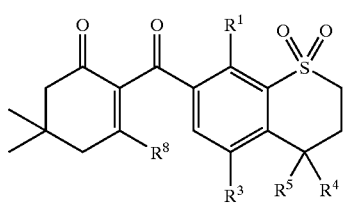

Ia2

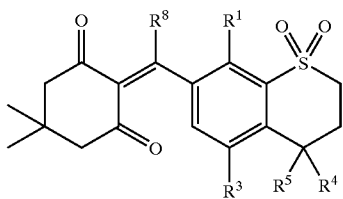

Ib2

The compounds of the formulae Ia3 and Ib3, in particular the compounds Ia3.1 to Ia3.342 and the compounds Ib3.1 to Ib3.342 which differ from the compounds Ia1.1 to Ia1.342 and Ib1.1 to Ib1.342, respectively, in that $(R^9)_q$ is "5-methyl".

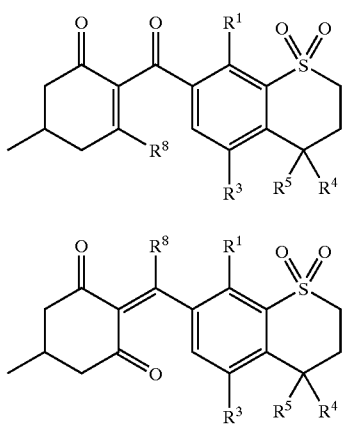

Ia3

Ib3

The compounds of the formulae Ia4 and Ib4, in particular the compounds Ia4.1 to Ia4.342 and the compounds Ib4.1 to Ib4.342 which differ from the compounds Ia1.1 to Ia1.342 and Ib1.1 to Ib1.342, respectively, in that $(R^9)_q$ is "4,4-dimethyl".

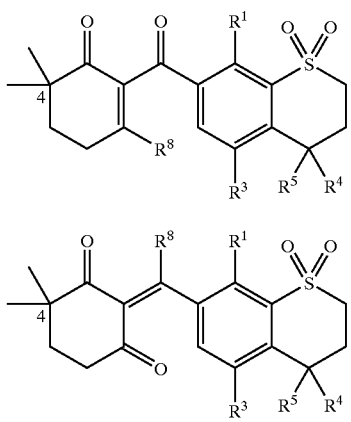

Ia4

Ib4

The compounds of the formulae Ia5 and Ib5, in particular the compounds Ia5.1 to Ia5.342 and the compounds Ib5.1 to Ib5.342 which differ from the compounds Ia1.1 to Ia1.342 and Ib1.1 to Ib1.342, respectively, in that $(R^9)_q$ is "6,6-dimethyl".

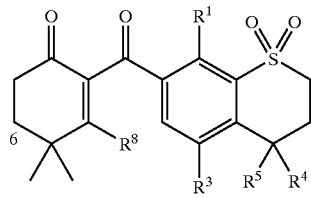

Ia5

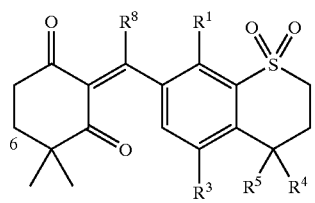

Ib5

The compounds of the formulae Ia6 and Ib6, in particular the compounds Ia6.1 to Ia6.342 and the compounds Ib6.1 to Ib6.342 which differ from the compounds Ia1.1 to Ia1.342 and Ib1.1 to Ib1.342, respectively, in that $(R^9)_q$ is "4,4,6,6-tetramethyl-5-oxo".

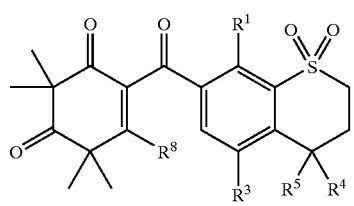

Ia6

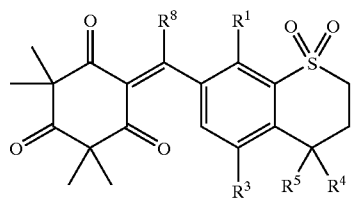

Ib6

The compounds of the formulae Ia7 and Ib7, in particular the compounds Ia7.1 to Ia7.342 and the compounds Ib7.1 to Ib7.342 which differ from the compounds Ia1.1 to Ia1.342 and Ib1.1 to Ib1.342, respectively, in that $(R^9)_q$ is "6-methyl".

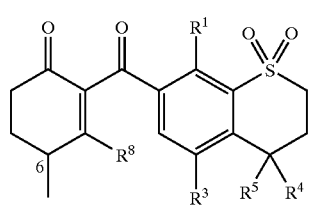

Ia7

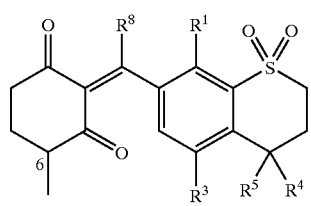

Ib7

The compounds of the formulae Ia8 and Ib8, in particular the compounds Ia8.1 to Ia8.342 and the compounds Ib8.1 to Ib8.342 which differ from the compounds Ia1.1 to Ia1.342 and Ib1.1 to Ib1.342, respectively, in that $(R^9)_q$ is "5-hydroxy-4,4,6,6-tetramethyl".

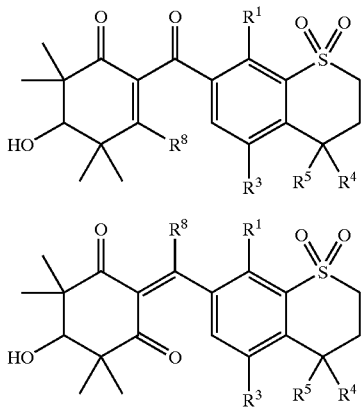

Ia8

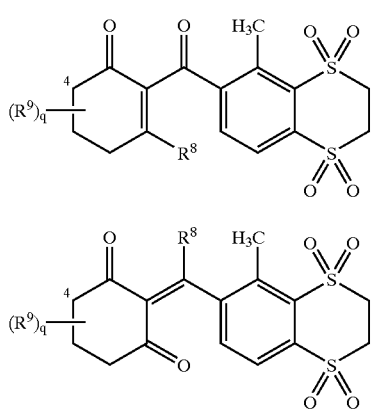

Ia8

Extraordinary preference is also given to the compounds of the formulae Ia9 and Ib9 (=I where X=SO$_2$, R$^1$=CH$_3$, R$^3$=H and l=0), in particular to the compounds Ia9.1 to Ia9.456 and Ib9.1 to Ib9.456 where the radical definitions R$^1$ to R$^9$, l and q not only in combination with one another, but in each case also on their own, have a particular meaning for the compounds according to the invention.

TABLE 2

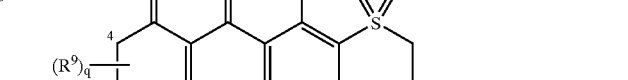

Ia9

Ib9

| No. | R$^8$ | $(R^9)_q$ |
|---|---|---|
| Ia9.1 or Ib9.1 | F | q = 0 |
| Ia9.2 or Ib9.2 | Cl | q = 0 |
| Ia9.3 or Ib9.3 | Br | q = 0 |
| Ia9.4 or Ib9.4 | I | q = 0 |
| Ia9.5 or Ib9.5 | SO$_2$CH$_3$ | q = 0 |
| Ia9.6 or Ib9.6 | SO$_2$CH$_2$CH$_3$ | q = 0 |
| Ia9.7 or Ib9.7 | SC$_6$H$_5$ | q = 0 |
| Ia9.8 or Ib9.8 | S(4-CH$_3$—C$_6$H$_4$) | q = 0 |
| Ia9.9 or Ib9.9 | S(4-Cl—C$_6$H$_4$) | q = 0 |
| Ia9.10 or Ib9.10 | SO$_2$C$_6$H$_5$ | q = 0 |
| Ia9.11 or Ib9.11 | SO$_2$(4-CH$_3$—C$_6$H$_4$) | q = 0 |
| Ia9.12 or Ib9.12 | SO$_2$(4-Cl—C$_6$H$_4$) | q = 0 |
| Ia9.13 or Ib9.13 | 4-morpholinyl | q = 0 |
| Ia9.14 or Ib9.14 | 1-pyrrolidinyl | q = 0 |
| Ia9.15 or Ib9.15 | 1-(1,2,4-triazolyl) | q = 0 |
| Ia9.16 or Ib9.16 | 1-imidazolyl | q = 0 |
| Ia9.17 or Ib9.17 | N(OCH$_3$)CH$_3$ | q = 0 |
| Ia9.18 or Ib9.18 | 2-tetrahydroisoxazolyl | q = 0 |
| Ia9.19 or Ib9.19 | N(CH$_3$)N(CH$_3$)$_2$ | q = 0 |
| Ia9.20 or Ib9.20 | N(CH$_2$CH=CH$_2$)N(CH$_3$)$_2$ | q = 0 |

TABLE 2-continued

| No. | R$^8$ | $(R^9)_q$ |
|---|---|---|
| Ia9.21 or Ib9.21 | OPO(OCH$_3$)$_2$ | q = 0 |
| Ia9.22 or Ib9.22 | OPO(OCH$_2$CH$_3$)$_2$ | q = 0 |
| Ia9.23 or Ib9.23 | OPO(OC$_6$H$_5$)$_2$ | q = 0 |
| Ia9.24 or Ib9.24 | OPO(CH$_3$)$_2$ | q = 0 |
| Ia9.25 or Ib9.25 | OPO(CH$_2$CH$_3$)$_2$ | q = 0 |
| Ia9.26 or Ib9.26 | OPO(C$_6$H$_5$)$_2$ | q = 0 |
| Ia9.27 or Ib9.27 | OPS(OCH$_3$)$_2$ | q = 0 |
| Ia9.28 or Ib9.28 | OPS(OCH$_2$CH$_3$)$_2$ | q = 0 |
| Ia9.29 or Ib9.29 | PO(OCH$_3$)$_2$ | q = 0 |
| Ia9.30 or Ib9.30 | PO(OCH$_2$CH$_3$)$_2$ | q = 0 |
| Ia9.31 or Ib9.31 | PO(C$_6$H$_5$)$_2$ | q = 0 |
| Ia9.32 or Ib9.32 | OCH$_2$C$_6$H$_5$ | q = 0 |
| Ia9.33 or Ib9.33 | OCH$_2$(2-furyl) | q = 0 |
| Ia9.34 or Ib9.34 | OCH$_2$(3-furyl) | q = 0 |
| Ia9.35 or Ib9.35 | OCOOCH$_3$ | q = 0 |
| Ia9.36 or Ib9.36 | OCOOCH$_2$CH$_3$ | q = 0 |
| Ia9.37 or Ib9.37 | OCOOCH(CH$_3$)$_2$ | q = 0 |
| Ia9.38 or Ib9.38 | OCOOC$_6$H$_5$ | q = 0 |
| Ia9.39 or Ib9.39 | OCOOC(CH$_3$)$_3$ | q = 0 |
| Ia9.40 or Ib9.40 | OCSOC$_6$H$_5$ | q = 0 |
| Ia9.41 or Ib9.41 | OCSN(CH$_3$)$_2$ | q = 0 |
| Ia9.42 or Ib9.42 | OCON(CH$_3$)$_2$ | q = 0 |
| Ia9.43 or Ib9.43 | OCOSCH$_3$ | q = 0 |
| Ia9.44 or Ib9.44 | ON(CH$_3$)$_2$ | q = 0 |
| Ia9.45 or Ib9.45 | O-1-piperidyl | q = 0 |
| Ia9.46 or Ib9.46 | OCO(CH$_2$)$_6$CH$_3$ | q = 0 |
| Ia9.47 or Ib9.47 | OCO(CH$_2$)$_7$CH$_3$ | q = 0 |
| Ia9.48 or Ib9.48 | OCO(CH$_2$)$_{16}$CH$_3$ | q = 0 |
| Ia9.49 or Ib9.49 | OCO(CH$_2$)$_{14}$CH$_3$ | q = 0 |
| Ia9.50 or Ib9.50 | OCOCH$_2$CH$_2$CH=CH$_2$ | q = 0 |
| Ia9.51 or Ib9.51 | OCOcyclopropyl | q = 0 |
| Ia9.52 or Ib9.52 | OCOcyclopentyl | q = 0 |
| Ia9.53 or Ib9.53 | OCOcyclohexyl | q = 0 |
| Ia9.54 or Ib9.54 | OCO(2-tetrahydrofuryl) | q = 0 |
| Ia9.55 or Ib9.55 | OCO(2-furyl) | q = 0 |
| Ia9.56 or Ib9.56 | OCO(2-thienyl) | q = 0 |
| Ia9.57 or Ib9.57 | OCO(3-pyridyl) | q = 0 |
| Ia9.58 or Ib9.58 | F | 4,4-dimethyl |
| Ia9.59 or Ib9.59 | Cl | 4,4-dimethyl |
| Ia9.60 or Ib9.60 | Br | 4,4-dimethyl |
| Ia9.61 or Ib9.61 | I | 4,4-dimethyl |
| Ia9.62 or Ib9.62 | SO$_2$CH$_3$ | 4,4-dimethyl |
| Ia9.63 or Ib9.63 | SO$_2$CH$_2$CH$_3$ | 4,4-dimethyl |
| Ia9.64 or Ib9.64 | SC$_6$H$_5$ | 4,4-dimethyl |
| Ia9.65 or Ib9.65 | S(4-CH$_3$—C$_6$H$_4$) | 4,4-dimethyl |
| Ia9.66 or Ib9.66 | S(4-Cl—C$_6$H$_4$) | 4,4-dimethyl |
| Ia9.67 or Ib9.67 | SO$_2$C$_6$H$_5$ | 4,4-dimethyl |
| Ia9.68 or Ib9.68 | SO$_2$(4-CH$_3$—C$_6$H$_4$) | 4,4-dimethyl |
| Ia9.69 or Ib9.69 | SO$_2$(4-Cl—C$_6$H$_4$) | 4,4-dimethyl |
| Ia9.70 or Ib9.70 | 4-morpholinyl | 4,4-dimethyl |
| Ia9.71 or Ib9.71 | 1-pyrrolidinyl | 4,4-dimethyl |
| Ia9.72 or Ib9.72 | 1-(1,2,4-triazolyl) | 4,4-dimethyl |
| Ia9.73 or Ib9.73 | 1-imidazolyl | 4,4-dimethyl |
| Ia9.74 or Ib9.74 | N(OCH$_3$)CH$_3$ | 4,4-dimethyl |
| Ia9.75 or Ib9.75 | 2-tetrahydroisoxazolyl | 4,4-dimethyl |
| Ia9.76 or Ib9.76 | N(CH$_3$)N(CH$_3$)$_2$ | 4,4-dimethyl |

TABLE 2-continued

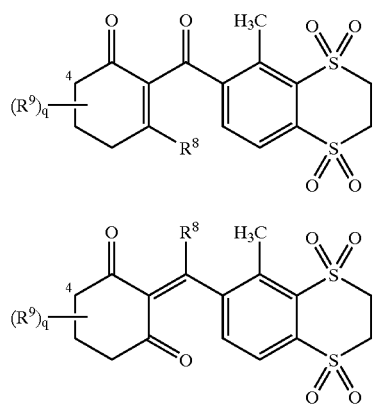

Ia9

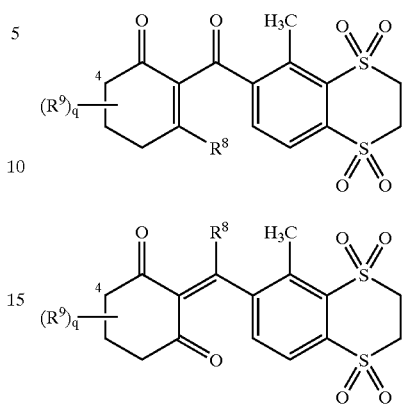

Ia9

Ib9

Ib9

| No. | R⁸ | (R⁹)q |
|---|---|---|
| Ia9.77 or Ib9.77 | N(CH₂—CH=CH₂)-N(CH₃)₂ | 4,4-dimethyl |
| Ia9.78 or Ib9.78 | OPO(OCH₃)₂ | 4,4-dimethyl |
| Ia9.79 or Ib9.79 | OPO(OCH₂CH₃)₂ | 4,4-dimethyl |
| Ia9.80 or Ib9.80 | OPO(OC₆H₅)₂ | 4,4-dimethyl |
| Ia9.81 or Ib9.81 | OPO(CH₃)₂ | 4,4-dimethyl |
| Ia9.82 or Ib9.82 | OPO(CH₂CH₃)₂ | 4,4-dimethyl |
| Ia9.83 or Ib9.83 | OPO(C₆H₅)₂ | 4,4-dimethyl |
| Ia9.84 or Ib9.84 | OPS(OCH₃)₂ | 4,4-dimethyl |
| Ia9.85 or Ib9.85 | OPS(OCH₂CH₃)₂ | 4,4-dimethyl |
| Ia9.86 or Ib9.86 | PO(OCH₃)₂ | 4,4-dimethyl |
| Ia9.87 or Ib9.87 | PO(OCH₂CH₃)₂ | 4,4-dimethyl |
| Ia9.88 or Ib9.88 | PO(C₆H₅)₂ | 4,4-dimethyl |
| Ia9.89 or Ib9.89 | OCH₂C₆H₅ | 4,4-dimethyl |
| Ia9.90 or Ib9.90 | OCH₂(2-furyl) | 4,4-dimethyl |
| Ia9.91 or Ib9.91 | OCH₂(3-furyl) | 4,4-dimethyl |
| Ia9.92 or Ib9.92 | OCOOCH₃ | 4,4-dimethyl |
| Ia9.93 or Ib9.93 | OCOOCH₂CH₃ | 4,4-dimethyl |
| Ia9.94 or Ib9.94 | OCOOCH(CH₃)₂ | 4,4-dimethyl |
| Ia9.95 or Ib9.95 | OCOOC₆H₅ | 4,4-dimethyl |
| Ia9.96 or Ib9.96 | OCOOC(CH₃)₃ | 4,4-dimethyl |
| Ia9.97 or Ib9.97 | OCSOC₆H₅ | 4,4-dimethyl |
| Ia9.98 or Ib9.98 | OCSN(CH₃)₂ | 4,4-dimethyl |
| Ia9.99 or Ib9.99 | OCON(CH₃)₂ | 4,4-dimethyl |
| Ia9.100 or Ib9.100 | OCOSCH₃ | 4,4-dimethyl |
| Ia9.101 or Ib9.101 | ON(CH₃)₂ | 4,4-dimethyl |
| Ia9.102 or Ib9.102 | O-1-piperidyl | 4,4-dimethyl |
| Ia9.103 or Ib9.103 | OCO(CH₂)₆CH₃ | 4,4-dimethyl |
| Ia9.104 or Ib9.104 | OCO(CH₂)₇CH₃ | 4,4-dimethyl |
| Ia9.105 or Ib9.105 | OCO(CH₂)₁₆CH₃ | 4,4-dimethyl |
| Ia9.106 or Ib9.106 | OCO(CH₂)₁₄CH₃ | 4,4-dimethyl |
| Ia9.107 or Ib9.107 | OCOCH₂CH₂CH=CH₂ | 4,4-dimethyl |
| Ia9.108 or Ib9.108 | OCOcyclopropyl | 4,4-dimethyl |
| Ia9.109 or Ib9.109 | OCOcyclopentyl | 4,4-dimethyl |
| Ia9.110 or Ib9.110 | OCOcyclohexyl | 4,4-dimethyl |
| Ia9.111 or Ib9.111 | OCO-(2-tetrahydrofuryl) | 4,4-dimethyl |
| Ia9.112 or Ib9.112 | OCO(2-furyl) | 4,4-dimethyl |
| Ia9.113 or Ib9.113 | OCO(2-thienyl) | 4,4-dimethyl |
| Ia9.114 or Ib9.114 | OCO (3-pyridyl) | 4,4-dimethyl |
| Ia9.115 or Ib9.115 | F | 5,5-dimethyl |
| Ia9.116 or Ib9.116 | Cl | 5,5-dimethyl |
| Ia9.117 or Ib9.117 | Br | 5,5-dimethyl |
| Ia9.118 or Ib9.118 | I | 5,5-dimethyl |
| Ia9.119 or Ib9.119 | SO₂CH₃ | 5,5-dimethyl |
| Ia9.120 or Ib9.120 | SO₂CH₂CH₃ | 5,5-dimethyl |
| Ia9.121 or Ib9.121 | SC₆H₅ | 5,5-dimethyl |
| Ia9.122 or Ib9.122 | S(4-CH₃—C₆H₄) | 5,5-dimethyl |
| Ia9.123 or Ib9.123 | S(4-Cl—C₆H₄) | 5,5-dimethyl |
| Ia9.124 or Ib9.124 | SO₂C₆H₅ | 5,5-dimethyl |
| Ia9.125 or Ib9.125 | SO₂(4-CH₃—C₆H₄) | 5,5-dimethyl |
| Ia9.126 or Ib9.126 | SO₂(4-Cl—C₆H₄) | 5,5-dimethyl |
| Ia9.127 or Ib9.127 | 4-morpholinyl | 5,5-dimethyl |
| Ia9.128 or Ib9.128 | 1-pyrrolidinyl | 5,5-dimethyl |
| Ia9.129 or Ib9.129 | 1-(1,2,4-triazolyl) | 5,5-dimethyl |
| Ia9.130 or Ib9.130 | 1-imidazolyl | 5,5-dimethyl |
| Ia9.131 or Ib9.131 | N(OCH₃)CH₃ | 5,5-dimethyl |
| Ia9.132 or Ib9.132 | 2-tetrahydroisoxazolyl | 5,5-dimethyl |
| Ia9.133 or Ib9.133 | N(CH₃N(CH₃)₂ | 5,5-dimethyl |
| Ia9.134 or Ib9.134 | N(CH₂CH=CH₂)N(CH₃)₂ | 5,5-dimethyl |
| Ia9.135 or Ib9.135 | OPO(OCH₃)₂ | 5,5-dimethyl |
| Ia9.136 or Ib9.136 | OPO(OCH₂CH₃)₂ | 5,5-dimethyl |
| Ia9.137 or Ib9.137 | OPO(OC₆H₅)₂ | 5,5-dimethyl |
| Ia9.138 or Ib9.138 | OPO(CH₃)₂ | 5,5-dimethyl |
| Ia9.139 or Ib9.139 | OPO(CH₂CH₃)₂ | 5,5-dimethyl |
| Ia9.140 or Ib9.140 | OPO(C₆H₅)₂ | 5,5-dimethyl |
| Ia9.141 or Ib9.141 | OPS(OCH₃)₂ | 5,5-dimethyl |
| Ia9.142 or Ib9.142 | OPS(OCH₂CH₃)₂ | 5,5-dimethyl |
| Ia9.143 or Ib9.143 | PO(OCH₃)₂ | 5,5-dimethyl |
| Ia9.144 or Ib9.144 | PO(OCH₂CH₃)₂ | 5,5-dimethyl |
| Ia9.145 or Ib9.145 | PO(C₆H₅)₂ | 5,5-dimethyl |
| Ia9.146 or Ib9.146 | OCH₂C₆H₅ | 5,5-dimethyl |
| Ia9.147 or Ib9.147 | OCH₂(2-furyl) | 5,5-dimethyl |
| Ia9.148 or Ib9.148 | OCH₂(3-furyl) | 5,5-dimethyl |
| Ia9.149 or Ib9.149 | OCOOCH₃ | 5,5-dimethyl |
| Ia9.150 or Ib9.150 | OCOOCH₂CH₃ | 5,5-dimethyl |
| Ia9.151 or Ib9.151 | OCOOCH(CH₃)₂ | 5,5-dimethyl |
| Ia9.152 or Ib9.152 | OCOOC₆H₅ | 5,5-dimethyl |
| Ia9.153 or Ib9.153 | OCOOC(CH₃)₃ | 5,5-dimethyl |
| Ia9.154 or Ib9.154 | OCSOC₆H₅ | 5,5-dimethyl |
| Ia9.155 or Ib9.155 | OCSN(CH₃)₂ | 5,5-dimethyl |
| Ia9.156 or Ib9.156 | OCON(CH₃)₂ | 5,5-dimethyl |
| Ia9.157 or Ib9.157 | OCOSCH₃ | 5,5-dimethyl |
| Ia9.158 or Ib9.158 | ON(CH₃)₂ | 5,5-dimethyl |
| Ia9.159 or Ib9.159 | O-1-piperidyl | 5,5-dimethyl |
| Ia9.160 or Ib9.160 | OCO(CH₂)₆CH₃ | 5,5-dimethyl |
| Ia9.161 or Ib9.161 | OCO(CH₂)₇CH₃ | 5,5-dimethyl |
| Ia9.162 or Ib9.162 | OCO(CH₂)₁₆CH₃ | 5,5-dimethyl |
| Ia9.163 or Ib9.163 | OCO(CH₂)₁₄CH₃ | 5,5-dimethyl |
| Ia9.164 or Ib9.164 | OCOCH₂CH₂CH=CH₂ | 5,5-dimethyl |
| Ia9.165 or Ib9.165 | OCOcyclopropyl | 5,5-dimethyl |
| Ia9.166 or Ib9.166 | OCOcyclopentyl | 5,5-dimethyl |
| Ia9.167 or Ib9.167 | OCOcyclohexyl | 5,5-dimethyl |
| Ia9.168 or Ib9.168 | OCO(2-tetrahydrofuryl) | 5,5-dimethyl |
| Ia9.169 or Ib9.169 | OCO(2-furyl) | 5,5-dimethyl |
| Ia9.170 or Ib9.170 | OCO(2-thienyl) | 5,5-dimethyl |
| Ia9.171 or Ib9.171 | OCO(3-pyridyl) | 5,5-dimethyl |
| Ia9.172 or Ib9.172 | F | 4,4,6,6-tetra-methyl-5-oxo |
| Ia9.173 or Ib9.173 | Cl | 4,4,6,6-tetra-methyl-5-oxo |
| Ia9.174 or Ib9.174 | Br | 4,4,6,6-tetra-methyl-5-oxo |
| Ia9.175 or Ib9.175 | I | 4,4,6,6-tetra-methyl-5-oxo |
| Ia9.176 or Ib9.176 | SO₂CH₃ | 4,4,6,6-tetra-methyl-5-oxo |
| Ia9.177 or Ib9.177 | SO₂CH₂CH₃ | 4,4,6,6-tetra-methyl-5-oxo |
| Ia9.178 or Ib9.178 | SC₆H₅ | 4,4,6,6-tetra-methyl-5-oxo |
| Ia9.179 or Ib9.179 | S(4-CH₃—C₆H₄) | 4,4,6,6-tetra-methyl-5-oxo |

TABLE 2-continued

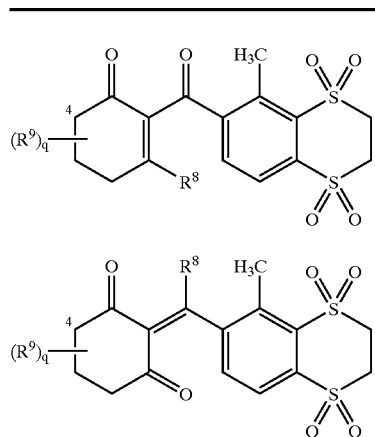

Ia9

Ib9

Ia9

Ib9

| No. | R⁸ | (R⁹)q |
|---|---|---|
| Ia9.180 or Ib9.180 | S(4-Cl—$C_6H_4$) | 4,4,6,6-tetra-methyl-5-oxo |
| Ia9.181 or Ib9.181 | $SO_2C_6H_5$ | 4,4,6,6-tetra-methyl-5-oxo |
| Ia9.182 or Ib9.182 | $SO_2$(4-$CH_3$—$C_6H_4$) | 4,4,6,6-tetra-methyl-5-oxo |
| Ia9.183 or Ib9.183 | $SO_2$(4-Cl—$C_6H_4$) | 4,4,6,6-tetra-methyl-5-oxo |
| Ia9.184 or Ib9.184 | 4-morpholinyl | 4,4,6,6-tetra-methyl-5-oxo |
| Ia9.185 or Ib9.185 | 1-pyrrolidinyl | 4,4,6,6-tetra-methyl-5-oxo |
| Ia9.186 or Ib9.186 | 1-(1,2,4-triazolyl) | 4,4,6,6-tetra-methyl-5-oxo |
| Ia9.187 or Ib9.187 | 1-imidazolyl | 4,4,6,6-tetra-methyl-5-oxo |
| Ia9.188 or Ib9.188 | N(OCH$_3$)CH$_3$ | 4,4,6,6-tetra-methyl-5-oxo |
| Ia9.189 or Ib9.189 | 2-tetrahydroisoxazolyl | 4,4,6,6-tetra-methyl-5-oxo |
| Ia9.190 or Ib9.190 | N(CH$_3$)N(CH$_3$)$_2$ | 4,4,6,6-tetra-methyl-5-oxo |
| Ia9.191 or Ib9.191 | N(CH$_2$—CH=CH$_2$)-N(CH$_3$)$_2$ | 4,4,6,6-tetra-methyl-5-oxo |
| Ia9.192 or Ib9.192 | OPO(OCH$_3$)$_2$ | 4,4,6,6-tetra-methyl-5-oxo |
| Ia9.193 or Ib9.193 | OPO(OCH$_2$CH$_3$)$_2$ | 4,4,6,6-tetra-methyl-5-oxo |
| Ia9.194 or Ib9.194 | OPO(OC$_6$H$_5$)$_2$ | 4,4,6,6-tetra-methyl-5-oxo |
| Ia9.195 or Ib9.195 | OPO(CH$_3$)$_2$ | 4,4,6,6-tetra-methyl-5-oxo |
| Ia9.196 or Ib9.196 | OPO(CH$_2$CH$_3$)$_2$ | 4,4,6,6-tetra-methyl-5-oxo |
| Ia9.197 or Ib9.197 | OPO(C$_6$H$_5$)$_2$ | 4,4,6,6-tetra-methyl-5-oxo |
| Ia9.198 or Ib9.198 | OPS(OCH$_3$)$_2$ | 4,4,6,6-tetra-methyl-5-oxo |
| Ia9.199 or Ib9.199 | OPS(OCH$_2$CH$_3$)$_2$ | 4,4,6,6-tetra-methyl-5-oxo |
| Ia9.200 or Ib9.200 | PO(OCH$_3$)$_2$ | 4,4,6,6-tetra-methyl-5-oxo |
| Ia9.201 or Ib9.201 | PO(OCH$_2$CH$_3$)$_2$ | 4,4,6,6-tetra-methyl-5-oxo |
| Ia9.202 or Ib9.202 | PO(C$_6$H$_5$)$_2$ | 4,4,6,6-tetra-methyl-5-oxo |
| Ia9.203 or Ib9.203 | OCH$_2$C$_6$H$_5$ | 4,4,6,6-tetra-methyl-5-oxo |
| Ia9.204 or Ib9.204 | OCH$_2$(2-furyl) | 4,4,6,6-tetra-methyl-5-oxo |
| Ia9.205 or Ib9.205 | OCH$_2$(3-furyl) | 4,4,6,6-tetra-methyl-5-oxo |
| Ia9.206 or Ib9.206 | OCOOCH$_3$ | 4,4,6,6-tetra-methyl-5-oxo |
| Ia9.207 or Ib9.207 | OCOOCH$_2$CH$_3$ | 4,4,6,6-tetra-methyl-5-oxo |
| Ia9.208 or Ib9.208 | OCOOCH(CH$_3$)$_2$ | 4,4,6,6-tetra-methyl-5-oxo |
| Ia9.209 or Ib9.209 | OCOOC$_6$H$_5$ | 4,4,6,6-tetra-methyl-5-oxo |
| Ia9.210 or Ib9.210 | OCOOC(CH$_3$)$_3$ | 4,4,6,6-tetra-methyl-5-oxo |
| Ia9.211 or Ib9.211 | OCSOC$_6$H$_5$ | 4,4,6,6-tetra-methyl-5-oxo |
| Ia9.212 or Ib9.212 | OCSN(CH$_3$)$_2$ | 4,4,6,6-tetra-methyl-5-oxo |
| Ia9.213 or Ib9.213 | OCON(CH$_3$)$_2$ | 4,4,6,6-tetra-methyl-5-oxo |
| Ia9.214 or Ib9.214 | OCOSCH$_3$ | 4,4,6,6-tetra-methyl-5-oxo |
| Ia9.215 or Ib9.215 | ON(CH$_3$)$_2$ | 4,4,6,6-tetra-methyl-5-oxo |
| Ia9.216 or Ib9.216 | O-1-piperidyl | 4,4,6,6-tetra-methyl-5-oxo |
| Ia9.217 or Ib9.217 | OCO(CH$_3$)$_6$CH$_3$ | 4,4,6,6-tetra-methyl-5-oxo |
| Ia9.218 or Ib9.218 | OCO(CH$_2$)$_7$CH$_3$ | 4,4,6,6-tetra-methyl-5-oxo |
| Ia9.219 or Ib9.219 | OCO(CH$_2$)$_{16}$CH$_3$ | 4,4,6,6-tetra-methyl-5-oxo |
| Ia9.220 or Ib9.220 | OCO(CH$_2$)$_{14}$CH$_3$ | 4,4,6,6-tetra-methyl-5-oxo |
| Ia9.221 or Ib9.221 | OCOCH$_2$CH$_2$CH=CH$_2$ | 4,4,6,6-tetra-methyl-5-oxo |
| Ia9.222 or Ib9.222 | OCOcyclopropyl | 4,4,6,6-tetra-methyl-5-oxo |
| Ia9.223 or Ib9.223 | OCOcyclopentyl | 4,4,6,6-tetra-methyl-5-oxo |
| Ia9.224 or Ib9.224 | OCOcyclohexyl | 4,4,6,6-tetra-methyl-5-oxo |
| Ia9.225 or Ib9.225 | OCO(2-tetrahydrofuryl) | 4,4,6,6-tetra-methyl-5-oxo |
| Ia9.226 or Ib9.226 | OCO(2-furyl) | 4,4,6,6-tetra-methyl-5-oxo |
| Ia9.227 or Ib9.227 | OCO(2-thienyl) | 4,4,6,6-tetra-methyl-5-oxo |
| Ia9.228 or Ib9.228 | OCO(3-pyridyl) | 4,4,6,6-tetra-methyl-5-oxo |
| Ia9.229 or Ib9.229 | F | 4,4,6,6-tetra-methyl-5-hydroxy |
| Ia9.230 or Ib9.230 | Cl | 4,4,6,6-tetra-methyl-5-hydroxy |
| Ia9.231 or Ib9.231 | Br | 4,4,6,6-tetra-methyl-5-hydroxy |
| Ia9.232 or Ib9.232 | I | 4,4,6,6-tetra-methyl-5-hydroxy |

TABLE 2-continued

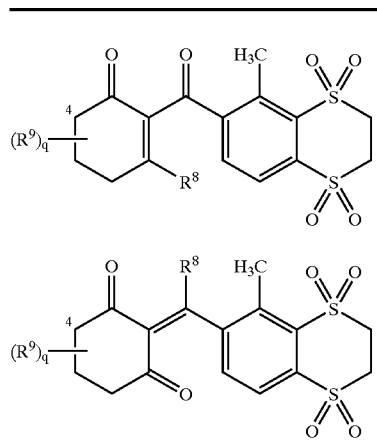

| No. | $R^8$ | $(R^9)_q$ |
|---|---|---|
| Ia9.233 or Ib9.233 | $SO_2CH_3$ | 4,4,6,6-tetramethyl-5-hydroxy |
| Ia9.234 or Ib9.234 | $SO_2CH_2CH_3$ | 4,4,6,6-tetramethyl-5-hydroxy |
| Ia9.235 or Ib9.235 | $SC_6H_5$ | 4,4,6,6-tetramethyl-5-hydroxy |
| Ia9.236 or Ib9.236 | $S(4-CH_3-C_6H_4)$ | 4,4,6,6-tetramethyl-5-hydroxy |
| Ia9.237 or Ib9.237 | $S(4-Cl-C_6H_4)$ | 4,4,6,6-tetramethyl-5-hydroxy |
| Ia9.238 or Ib9.238 | $SO_2C_6H_5$ | 4,4,6,6-tetramethyl-5-hydroxy |
| Ia9.239 or Ib9.239 | $SO_2(4-CH_3-C_6H_4)$ | 4,4,6,6-tetramethyl-5-hydroxy |
| Ia9.240 or Ib9.240 | $SO_2(4-Cl-C_6H_4)$ | 4,4,6,6-tetramethyl-5-hydroxy |
| Ia9.241 or Ib9.241 | 4-morpholinyl | 4,4,6,6-tetramethyl-5-hydroxy |
| Ia9.242 or Ib9.242 | 1-pyrrolidinyl | 4,4,6,6-tetramethyl-5-hydroxy |
| Ia9.243 or Ib9.243 | 1-triazolyl | 4,4,6,6-tetramethyl-5-hydroxy |
| Ia9.244 or Ib9.244 | 1-imidazolyl | 4,4,6,6-tetramethyl-5-hydroxy |
| Ia9.245 or Ib9.245 | $N(OCH_3)CH_3$ | 4,4,6,6-tetramethyl-5-hydroxy |
| Ia9.246 or Ib9.246 | 2-tetrahydroisoxazolyl | 4,4,6,6-tetramethyl-5-hydroxy |
| Ia9.247 or Ib9.247 | $N(CH_3)N(CH_3)_2$ | 4,4,6,6-tetramethyl-5-hydroxy |
| Ia9.248 or Ib9.248 | $N(CH_2CH=CH_2)N(CH_3)_2$ | 4,4,6,6-tetramethyl-5-hydroxy |
| Ia9.249 or Ib9.249 | $OPO(OCH_3)_2$ | 4,4,6,6-tetramethyl-5-hydroxy |
| Ia9.250 or Ib9.250 | $OPO(OCH_2CH_3)_2$ | 4,4,6,6-tetramethyl-5-hydroxy |
| Ia9.251 or Ib9.251 | $OPO(OC_6H_5)_2$ | 4,4,6,6-tetramethyl-5-hydroxy |
| Ia9.252 or Ib9.252 | $OPO(CH_3)_2$ | 4,4,6,6-tetramethyl-5-hydroxy |
| Ia9.253 or Ib9.253 | $OPO(CH_2CH_3)_2$ | 4,4,6,6-tetramethyl-5-hydroxy |
| Ia9.254 or Ib9.254 | $OPO(C_6H_5)_2$ | 4,4,6,6-tetramethyl-5-hydroxy |
| Ia9.255 or Ib9.255 | $OPS(OCH_3)_2$ | 4,4,6,6-tetramethyl-5-hydroxy |
| Ia9.256 or Ib9.256 | $OPS(OCH_2CH_3)_2$ | 4,4,6,6-tetramethyl-5-hydroxy |
| Ia9.257 or Ib9.257 | $PO(OCH_3)_2$ | 4,4,6,6-tetramethyl-5-hydroxy |
| Ia9.258 or Ib9.258 | $PO(OCH_2CH_3)_2$ | 4,4,6,6-tetramethyl-5-hydroxy |
| Ia9.259 or Ib9.259 | $PO(C_6H_5)_2$ | 4,4,6,6-tetramethyl-5-hydroxy |
| Ia9.260 or Ib9.260 | $OCH_2C_6H_5$ | 4,4,6,6-tetramethyl-5-hydroxy |
| Ia9.261 or Ib9.261 | $OCH_2(2-furyl)$ | 4,4,6,6-tetramethyl-5-hydroxy |
| Ia9.262 or Ib9.262 | $OCH_2(3-furyl)$ | 4,4,6,6-tetramethyl-5-hydroxy |
| Ia9.263 or Ib9.263 | $OCOOCH_3$ | 4,4,6,6-tetramethyl-5-hydroxy |
| Ia9.264 or Ib9.264 | $OCOOCH_2CH_3$ | 4,4,6,6-tetramethyl-5-hydroxy |
| Ia9.265 or Ib9.265 | $OCOOCH(CH_3)_2$ | 4,4,6,6-tetramethyl-5-hydroxy |
| Ia9.266 or Ib9.266 | $OCOOC_6H_5$ | 4,4,6,6-tetramethyl-5-hydroxy |
| Ia9.267 or Ib9.267 | $OCOOC(CH_3)_3$ | 4,4,6,6-tetramethyl-5-hydroxy |
| Ia9.268 or Ib9.268 | $OCSOC_6H_5$ | 4,4,6,6-tetramethyl-5-hydroxy |

TABLE 2-continued

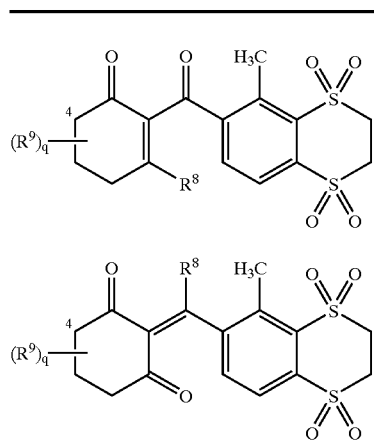

Ia9

Ib9

| No. | R⁸ | (R⁹)q |
|---|---|---|
| Ia9.269 or Ib9.269 | OCSN(CH₃)₂ | 4,4,6,6-tetramethyl-5-hydroxy |
| Ia9.270 or Ib9.270 | OCON(CH₃)₂ | 4,4,6,6-tetramethyl-5-hydroxy |
| Ia9.271 or Ib9.271 | OCOSCH₃ | 4,4,6,6-tetramethyl-5-hydroxy |
| Ia9.272 or Ib9.272 | ON(CH₃)₂ | 4,4,6,6-tetramethyl-5-hydroxy |
| Ia9.273 or Ib9.273 | O-1-piperidyl | 4,4,6,6-tetramethyl-5-hydroxy |
| Ia9.274 or Ib9.274 | OCO(CH₂)₆CH₃ | 4,4,6,6-tetramethyl-5-hydroxy |
| Ia9.275 or Ib9.275 | OCO(CH₂)₇CH₃ | 4,4,6,6-tetramethyl-5-hydroxy |
| Ia9.276 or Ib9.276 | OCO(CH₂)₁₆CH₃ | 4,4,6,6-tetramethyl-5-hydroxy |
| Ia9.277 or Ib9.277 | OCO(CH₂)₁₄CH₃ | 4,4,6,6-tetramethyl-5-hydroxy |
| Ia9.278 or Ib9.278 | OCOCH₂CH₂CH=CH₂ | 4,4,6,6-tetramethyl-5-hydroxy |
| Ia9.279 or Ib9.279 | OCOcyclopropyl | 4,4,6,6-tetramethyl-5-hydroxy |
| Ia9.280 or Ib9.280 | OCOcyclopentyl | 4,4,6,6-tetramethyl-5-hydroxy |
| Ia9.281 or Ib9.281 | OCOcyclohexyl | 4,4,6,6-tetramethyl-5-hydroxy |
| Ia9.282 or Ib9.282 | OCO(2-tetrahydrofuryl) | 4,4,6,6-tetramethyl-5-hydroxy |
| Ia9.283 or Ib9.283 | OCO(2-furyl) | 4,4,6,6-tetramethyl-5-hydroxy |
| Ia9.284 or Ib9.284 | OCO(2-thienyl) | 4,4,6,6-tetramethyl-5-hydroxy |
| Ia9.285 or Ib9.285 | OCO(3-pyridyl) | 4,4,6,6-tetramethyl-5-hydroxy |
| Ia9.286 or Ib9.286 | F | 5-methyl |
| Ia9.287 or Ib9.287 | Cl | 5-methyl |
| Ia9.288 or Ib9.288 | Br | 5-methyl |
| Ia9.289 or Ib9.289 | I | 5-methyl |
| Ia9.290 or Ib9.290 | SO₂CH₃ | 5-methyl |
| Ia9.291 or Ib9.291 | SO₂CH₂CH₃ | 5-methyl |
| Ia9.292 or Ib9.292 | SC₆H₅ | 5-methyl |
| Ia9.293 or Ib9.293 | S(4-CH₃—C₆H₄) | 5-methyl |
| Ia9.294 or Ib9.294 | S(4-Cl—C₆H₄) | 5-methyl |
| Ia9.295 or Ib9.295 | SO₂C₆H₅ | 5-methyl |
| Ia9.296 or Ib9.296 | SO₂(4-CH₃—C₆H₄) | 5-methyl |
| Ia9.297 or Ib9.297 | SO₂(4-Cl—C₆H₄) | 5-methyl |
| Ia9.298 or Ib9.298 | 4-morpholinyl | 5-methyl |
| Ia9.299 or Ib9.299 | 1-pyrrolidinyl | 5-methyl |
| Ia9.300 or Ib9.300 | 1-(1,2,4-triazolyl) | 5-methyl |
| Ia9.301 or Ib9.301 | 1-imidazolyl | 5-methyl |
| Ia9.302 or Ib9.302 | N(OCH₃)CH₃ | 5-methyl |
| Ia9.303 or Ib9.303 | 2-tetrahydroisoxazolyl | 5-methyl |
| Ia9.304 or Ib9.304 | N(CH₃)N(CH₃)₂ | 5-methyl |
| Ia9.305 or Ib9.305 | N(CH₂CH=CH₂)N(CH₃)₂ | 5-methyl |
| Ia9.306 or Ib9.306 | OPO(OCH₃)₂ | 5-methyl |
| Ia9.307 or Ib9.307 | OPO(OCH₂CH₃)₂ | 5-methyl |
| Ia9.308 or Ib9.308 | OPO(OC₆H₅)₂ | 5-methyl |
| Ia9.309 or Ib9.309 | OPO(CH₃)₂ | 5-methyl |
| Ia9.310 or Ib9.310 | OPO(CH₂CH₃)₂ | 5-methyl |
| Ia9.311 or Ib9.311 | OPO(C₆H₅)₂ | 5-methyl |
| Ia9.312 or Ib9.312 | OPS(OCH₃)₂ | 5-methyl |
| Ia9.313 or Ib9.313 | OPS(OCH₂CH₃)₂ | 5-methyl |
| Ia9.314 or Ib9.314 | PO(OCH₃)₂ | 5-methyl |
| Ia9.315 or Ib9.315 | PO(OCH₂CH₃)₂ | 5-methyl |
| Ia9.316 or Ib9.316 | PO(C₆H₅)₂ | 5-methyl |
| Ia9.317 or Ib9.317 | OCH₂C₆H₅ | 5-methyl |
| Ia9.318 or Ib9.318 | OCH₂(2-furyl) | 5-methyl |
| Ia9.319 or Ib9.319 | OCH₂(3-furyl) | 5-methyl |
| Ia9.320 or Ib9.320 | OCOOCH₃ | 5-methyl |
| Ia9.321 or Ib9.321 | OCOOCH₂CH₃ | 5-methyl |
| Ia9.322 or Ib9.322 | OCOOCH(CH₃)₂ | 5-methyl |
| Ia9.323 or Ib9.323 | OCOOC₆H₅ | 5-methyl |
| Ia9.324 or Ib9.324 | OCOOC(CH₃)₃ | 5-methyl |
| Ia9.325 or Ib9.325 | OCSOC₆H₅ | 5-methyl |
| Ia9.326 or Ib9.326 | OCSN(CH₃)₂ | 5-methyl |
| Ia9.327 or Ib9.327 | OCON(CH₃)₂ | 5-methyl |
| Ia9.328 or Ib9.328 | OCOSCH₃ | 5-methyl |
| Ia9.329 or Ib9.329 | ON(CH₃)₂ | 5-methyl |
| Ia9.330 or Ib9.330 | O-1-piperidyl | 5-methyl |
| Ia9.331 or Ib9.331 | OCO(CH₂)₆CH₃ | 5-methyl |
| Ia9.332 or Ib9.332 | OCO(CH₂)₇CH₃ | 5-methyl |
| Ia9.333 or Ib9.333 | OCO(CH₂)₁₆CH₃ | 5-methyl |
| Ia9.334 or Ib9.334 | OCO(CH₂)₁₄CH₃ | 5-methyl |
| Ia9.335 or Ib9.335 | OCOCH₂CH₂CH=CH₂ | 5-methyl |
| Ia9.336 or Ib9.336 | OCOcyclopropyl | 5-methyl |
| Ia9.337 or Ib9.337 | OCOcyclopentyl | 5-methyl |
| Ia9.338 or Ib9.338 | OCOcyclohexyl | 5-methyl |
| Ia9.339 or Ib9.339 | OCO(2-tetrahydrofuryl) | 5-methyl |
| Ia9.340 or Ib9.340 | OCO(2-furyl) | 5-methyl |
| Ia9.341 or Ib9.341 | OCO(2-thienyl) | 5-methyl |
| Ia9.342 or Ib9.342 | OCO(3-pyridyl) | 5-methyl |
| Ia9.343 or Ib9.343 | F | 4,4-spirocyclohexyl-6-methyl |
| Ia9.344 or Ib9.344 | Cl | 4,4-spirocyclohexyl-6-methyl |

TABLE 2-continued

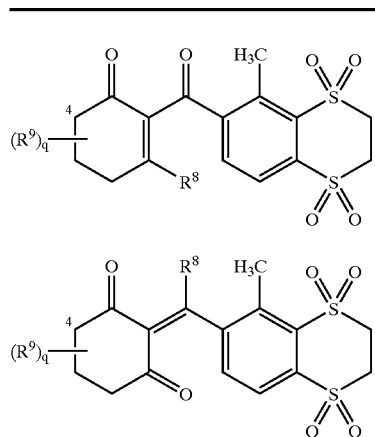

Ia9

Ib9

Ia9

Ib9

| No. | $R^8$ | $(R^9)_q$ |
|---|---|---|
| Ia9.345 or Ib9.345 | Br | 4,4-spirocyclohexyl-6-methyl |
| Ia9.346 or Ib9.346 | I | 4,4-spirocyclohexyl-6-methyl |
| Ia9.347 or Ib9.347 | $SO_2CH_3$ | 4,4-spirocyclohexyl-6-methyl |
| Ia9.348 or Ib9.348 | $SO_2CH_2CH_3$ | 4,4-spirocyclohexyl-6-methyl |
| Ia9.349 or Ib9.349 | $SC_6H_5$ | 4,4-spirocyclohexyl-6-methyl |
| Ia9.350 or Ib9.350 | $S(4\text{-}CH_3\text{—}C_6H_4)$ | 4,4-spirocyclohexyl-6-methyl |
| Ia9.351 or Ib9.351 | $S(4\text{-}Cl\text{—}C_6H_4)$ | 4,4-spirocyclohexyl-6-methyl |
| Ia9.352 or Ib9.352 | $SO_2C_6H_5$ | 4,4-spirocyclohexyl-6-methyl |
| Ia9.353 or Ib9.353 | $SO_2(4\text{-}CH_3\text{—}C_6H_4)$ | 4,4-spirocyclohexyl-6-methyl |
| Ia9.354 or Ib9.354 | $SO_2(4\text{-}Cl\text{—}C_6H_4)$ | 4,4-spirocyclohexyl-6-methyl |
| Ia9.355 or Ib9.355 | 4-morpholinyl | 4,4-spirocyclohexyl-6-methyl |
| Ia9.356 or Ib9.356 | 1-pyrrolidinyl | 4,4-spirocyclohexyl-6-methyl |
| Ia9.357 or Ib9.357 | 1-(1,2,4-triazolyl) | 4,4-spirocyclohexyl-6-methyl |
| Ia9.358 or Ib9.358 | 1-imidazolyl | 4,4-spirocyclohexyl-6-methyl |
| Ia9.359 or Ib9.359 | $N(OCH_3)CH_3$ | 4,4-spirocyclohexyl-6-methyl |
| Ia9.360 or Ib9.360 | 2-tetrahydroisoxazolyl | 4,4-spirocyclohexyl-6-methyl |
| Ia9.361 or Ib9.361 | $N(CH_3)N(CH_3)_2$ | 4,4-spirocyclohexyl-6-methyl |
| Ia9.362 or Ib9.362 | $N(CH_2CH=CH_2)N(CH_3)_2$ | 4,4-spirocyclohexyl-6-methyl |
| Ia9.363 or Ib9.363 | $OPO(OCH_3)_2$ | 4,4-spirocyclohexyl-6-methyl |
| Ia9.364 or Ib9.364 | $OPO(OCH_2CH_3)_2$ | 4,4-spirocyclohexyl-6-methyl |
| Ia9.365 or Ib9.365 | $OPO(OC_6H_5)_2$ | 4,4-spirocyclohexyl-6-methyl |
| Ia9.366 or Ib9.366 | $OPO(CH_3)_2$ | 4,4-spirocyclohexyl-6-methyl |
| Ia9.367 or Ib9.367 | $OPO(CH_2CH_3)_2$ | 4,4-spirocyclohexyl-6-methyl |
| Ia9.368 or Ib9.368 | $OPO(C_6H_5)_2$ | 4,4-spirocyclohexyl-6-methyl |
| Ia9.369 or Ib9.369 | $OPS(OCH_3)_2$ | 4,4-spirocyclohexyl-6-methyl |
| Ia9.370 or Ib9.370 | $OPS(OCH_2CH_3)_2$ | 4,4-spirocyclohexyl-6-methyl |
| Ia9.371 or Ib9.371 | $PO(OCH_3)_2$ | 4,4-spirocyclohexyl-6-methyl |
| Ia9.372 or Ib9.372 | $PO(OCH_2CH_3)_2$ | 4,4-spirocyclohexyl-6-methyl |
| Ia9.373 or Ib9.373 | $PO(C_6H_5)_2$ | 4,4-spirocyclohexyl-6-methyl |
| Ia9.374 or Ib9.374 | $OCH_2C_6H_5$ | 4,4-spirocyclohexyl-6-methyl |
| Ia9.375 or Ib9.375 | $OCH_2(\text{2-furyl})$ | 4,4-spirocyclohexyl-6-methyl |
| Ia9.376 or Ib9.376 | $OCH_2(\text{3-furyl})$ | 4,4-spirocyclohexyl-6-methyl |
| Ia9.377 or Ib9.377 | $OCOOCH_3$ | 4,4-spirocyclohexyl-6-methyl |
| Ia9.378 or Ib9.378 | $OCOOCH_2CH_3$ | 4,4-spirocyclohexyl-6-methyl |
| Ia9.379 or Ib9.379 | $OCOOCH(CH_3)_2$ | 4,4-spirocyclohexyl-6-methyl |
| Ia9.380 or Ib9.380 | $OCOOC_6H_5$ | 4,4-spirocyclohexyl-6-methyl |
| Ia9.381 or Ib9.381 | $OCOOC(CH_3)_3$ | 4,4-spirocyclohexyl-6-methyl |
| Ia9.382 or Ib9.382 | $OCSOC_6H_5$ | 4,4-spirocyclohexyl-6-methyl |
| Ia9.383 or Ib9.383 | $OCSN(CH_3)_2$ | 4,4-spirocyclohexyl-6-methyl |
| Ia9.384 or Ib9.384 | $OCON(CH_3)_2$ | 4,4-spirocyclohexyl-6-methyl |
| Ia9.385 or Ib9.385 | $OCOSCH_3$ | 4,4-spirocyclohexyl-6-methyl |
| Ia9.386 or Ib9.386 | $ON(CH_3)_2$ | 4,4-spirocyclohexyl-6-methyl |
| Ia9.387 or Ib9.387 | O-1-piperidyl | 4,4-spirocyclohexyl-6-methyl |
| Ia9.388 or Ib9.388 | $OCO(CH_2)_6CH_3$ | 4,4-spirocyclohexyl-6-methyl |
| Ia9.389 or Ib9.389 | $OCO(CH_2)_7CH_3$ | 4,4-spirocyclohexyl-6-methyl |
| Ia9.390 or Ib9.390 | $OCO(CH_2)_{16}CH_3$ | 4,4-spirocyclohexyl-6-methyl |
| Ia9.391 or Ib9.391 | $OCO(CH_2)_{14}CH_3$ | 4,4-spirocyclohexyl-6-methyl |
| Ia9.392 or Ib9.392 | $OCOCH_2CH_2CH=CH_2$ | 4,4-spirocyclohexyl-6-methyl |
| Ia9.393 or Ib9.393 | OCOcyclopropyl | 4,4-spirocyclohexyl-6-methyl |
| Ia9.394 or Ib9.394 | OCOcyclopentyl | 4,4-spirocyclohexyl-6-methyl |
| Ia9.395 or Ib9.395 | OCOcyclohexyl | 4,4-spirocyclohexyl-6-methyl |
| Ia9.396 or Ib9.396 | OCO-(2-tetrahydrofuryl) | 4,4-spirocyclohexyl-6-methyl |
| Ia9.397 or Ib9.397 | OCO(2-furyl) | 4,4-spirocyclohexyl-6-methyl |
| Ia9.398 or Ib9.398 | OCO(2-thienyl) | 4,4-spirocyclohexyl-6-methyl |
| Ia9.399 or Ib9.399 | OCO(3-pyridyl) | 4,4-spirocyclohexyl-6-methyl |
| Ia9.400 or Ib9.400 | F | 4-methyl-4-thiomethyl |

TABLE 2-continued

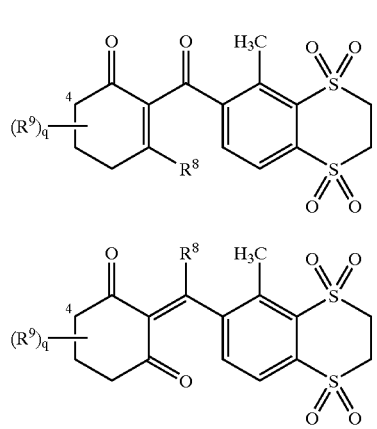

| No. | R⁸ | (R⁹)q |
|---|---|---|
| Ia9.401 or Ib9.401 | Cl | 4-methyl-4-thiomethyl |
| Ia9.402 or Ib9.402 | Br | 4-methyl-4-thiomethyl |
| Ia9.403 or Ib9.403 | I | 4-methyl-4-thiomethyl |
| Ia9.404 or Ib9.404 | $SO_2CH_3$ | 4-methyl-4-thiomethyl |
| Ia9.405 or Ib9.405 | $SO_2CH_2CH_3$ | 4-methyl-4-thiomethyl |
| Ia9.406 or Ib9.406 | $SC_6H_5$ | 4-methyl-4-thiomethyl |
| Ia9.407 or Ib9.407 | $S(4-CH_3-C_6H_4)$ | 4-methyl-4-thiomethyl |
| Ia9.408 or Ib9.408 | $S(4-Cl-C_6H_4)$ | 4-methyl-4-thiomethyl |
| Ia9.409 or Ib9.409 | $SO_2C_6H_5$ | 4-methyl-4-thiomethyl |
| Ia9.410 or Ib9.410 | $SO_2(4-CH_3-C_6H_4)$ | 4-methyl-4-thiomethyl |
| Ia9.411 or Ib9.411 | $SO_2(4-Cl-C_6H_4)$ | 4-methyl-4-thiomethyl |
| Ia9.412 or Ib9.412 | 4-morpholinyl | 4-methyl-4-thiomethyl |
| Ia9.413 or Ib9.413 | 1-pyrrolidinyl | 4-methyl-4-thiomethyl |
| Ia9.414 or Ib9.414 | 1-(1,2,4-triazolyl) | 4-methyl-4-thiomethyl |
| Ia9.415 or Ib9.415 | 1-imidazolyl | 4-methyl-4-thiomethyl |
| Ia9.416 or Ib9.416 | $N(OCH_3)CH_3$ | 4-methyl-4-thiomethyl |
| Ia9.417 or Ib9.417 | 2-tetrahydroisoxazolyl | 4-methyl-4-thiomethyl |
| Ia9.418 or Ib9.418 | $N(CH_3)N(CH_3)_2$ | 4-methyl-4-thiomethyl |
| Ia9.419 or Ib9.419 | $N(CH_2CH=CH_2)N(CH_3)_2$ | 4-methyl-4-thiomethyl |
| Ia9.420 or Ib9.420 | $OPO(OCH_3)_2$ | 4-methyl-4-thiomethyl |
| Ia9.421 or Ib9.421 | $OPO(OCH_2CH_3)_2$ | 4-methyl-4-thiomethyl |
| Ia9.422 or Ib9.422 | $OPO(OC_6H_5)_2$ | 4-methyl-4-thiomethyl |
| Ia9.423 or Ib9.423 | $OPO(CH_3)_2$ | 4-methyl-4-thiomethyl |
| Ia9.424 or Ib9.424 | $OPO(CH_2CH_3)_2$ | 4-methyl-4-thiomethyl |
| Ia9.425 or Ib9.425 | $OPO(C_6H_5)_2$ | 4-methyl-4-thiomethyl |
| Ia9.426 or Ib9.426 | $OPS(OCH_3)_2$ | 4-methyl-4-thiomethyl |
| Ia9.427 or Ib9.427 | $OPS(OCH_2CH_3)_2$ | 4-methyl-4-thiomethyl |
| Ia9.428 or Ib9.428 | $PO(OCH_3)_2$ | 4-methyl-4-thiomethyl |
| Ia9.429 or Ib9.429 | $PO(OCH_2CH_3)_2$ | 4-methyl-4-thiomethyl |
| Ia9.430 or Ib9.430 | $PO(C_6H_5)_2$ | 4-methyl-4-thiomethyl |
| Ia9.431 or Ib9.431 | $OCH_2C_6H_5$ | 4-methyl-4-thiomethyl |
| Ia9.432 or Ib9.432 | $OCH_2$(2-furyl) | 4-methyl-4-thiomethyl |
| Ia9.433 or Ib9.433 | $OCH_2$(3-furyl) | 4-methyl-4-thiomethyl |
| Ia9.434 or Ib9.434 | $OCOOCH_3$ | 4-methyl-4-thiomethyl |
| Ia9.435 or Ib9.435 | $OCOOCH_2CH_3$ | 4-methyl-4-thiomethyl |
| Ia9.436 or Ib9.436 | $OCOOCH(CH_3)_2$ | 4-methyl-4-thiomethyl |
| Ia9.437 or Ib9.437 | $OCOOC_6H_5$ | 4-methyl-4-thiomethyl |
| Ia9.438 or Ib9.438 | $OCOOC(CH_3)_3$ | 4-methyl-4-thiomethyl |
| Ia9.439 or Ib9.439 | $OCSOC_6H_5$ | 4-methyl-4-thiomethyl |
| Ia9.440 or Ib9.440 | $OCSN(CH_3)_2$ | 4-methyl-4-thiomethyl |
| Ia9.441 or Ib9.441 | $OCON(CH_3)_2$ | 4-methyl-4-thiomethyl |
| Ia9.442 or Ib9.442 | $OCOSCH_3$ | 4-methyl-4-thiomethyl |
| Ia9.443 or Ib9.443 | $ON(CH_3)_2$ | 4-methyl-4-thiomethyl |
| Ia9.444 or Ib9.444 | O-1-piperidyl | 4-methyl-4-thiomethyl |
| Ia9.445 or Ib9.445 | $OCO(CH_2)_6CH_3$ | 4-methyl-4-thiomethyl |
| Ia9.446 or Ib9.446 | $OCO(CH_2)_7CH_3$ | 4-methyl-4-thiomethyl |
| Ia9.447 or Ib9.447 | $OCO(CH_2)_{16}CH_3$ | 4-methyl-4-thiomethyl |
| Ia9.448 or Ib9.448 | $OCO(CH_2)_{14}CH_3$ | 4-methyl-4-thiomethyl |
| Ia9.449 or Ib9.449 | $OCOCH_2CH_2CH=CH_2$ | 4-methyl-4-thiomethyl |
| Ia9.450 or Ib9.450 | OCOcyclopropyl | 4-methyl-4-thiomethyl |
| Ia9.451 or Ib9.451 | OCOcyclopentyl | 4-methyl-4-thiomethyl |
| Ia9.452 or Ib9.452 | OCOcyclohexyl | 4-methyl-4-thiomethyl |
| Ia9.453 or Ib9.453 | OCO(2-tetrahydrofuryl) | 4-methyl-4-thiomethyl |
| Ia9.454 or Ib9.454 | OCO(2-furyl) | 4-methyl-4-thiomethyl |

TABLE 2-continued

Ia9

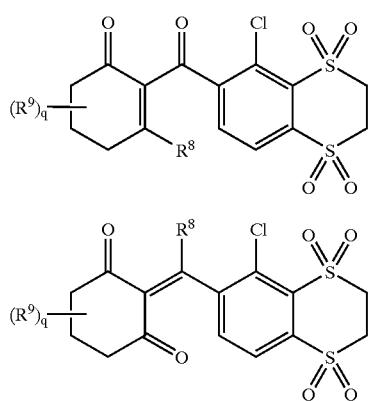

Ib9

| No. | R⁸ | $(R^9)_q$ |
|---|---|---|
| Ia9.455 or Ib9.455 | OCO(2-thienyl) | 4-methyl-4-thiomethyl |
| Ia9.456 or Ib9.456 | OCO(3-pyridyl) | 4-methyl-4-thiomethyl |

Furthermore, extraordinary preference is given to the compounds Ia10 and Ib10, in particular to the compounds Ia10.1 to Ia10.456 and Ib10.1 to Ib10.456, which differ from the compounds Ia9.1 to Ia9.456 and Ib9.1 to Ib9.456, respectively, in that $R^1$ is chlorine.

Ia10

Ib10

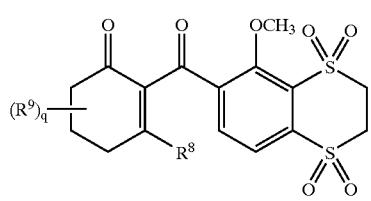

Likewise, extraordinary preference is given to the compounds Ia11 and Ib11 in particular to the compounds Ia11.1 to Ia11.456 and Ib11.1 to Ib11.456, which differ from the compounds Ia9.1 to Ia9.456 and Ib9.1 to Ib9.456, respectively, in that $R^1$ is methoxy.

Ia11

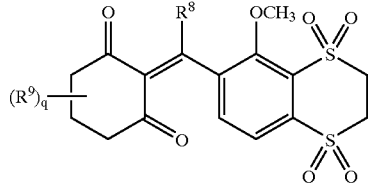

Ib11

Furthermore, extraordinary preference is given to the compounds Ia, in particular to the compounds Ia1 to Ia11, and to the embodiments mentioned in each case.

The cyclohexenonedioxothiochromanoyl derivatives of the formula I can be obtained by various routes, for example by the following processes:

A. Preparation of the compounds of the formula I where $R^8$=halogen by reaction of cyclohexanedione derivatives of the formula III with halogenating agents:

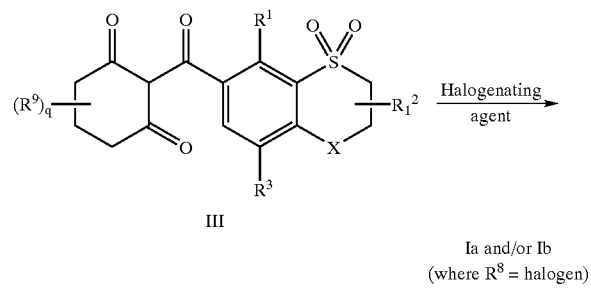

Suitable halogenating agents are, for example, phosgene, diphosgene, triphosgene, thionyl chloride, oxalyl chloride, phosphorus oxychloride, phosphorus pentachloride, mesyl chloride, chloromethylene-N,N-dimethylammonium chloride, oxylyl bromide, phosphorus oxybromide etc.

The starting materials are usually employed in equimolar amounts. However it can also be advantageous to employ one component or the other in excess.

Suitable solvents are, for example, chlorinated hydrocarbons, such as methylene chloride or 1,2-dichloroethane, aromatic hydrocarbons, for example toluene, xylene or chlorobenzene, polar aprotic solvents, such as acetonitrile, dimethylformamide or dimethyl sulfoxide, or mixtures of these. The reaction can also be carried out neat.

The reaction temperature is usually in the range from 0° C. to the boiling point of the reaction mixture.

Work-up to afford the product can be carried out in a manner known per se.

B. Preparation of compounds of the formula I where $R^8=OR^{10}$, $OSO_2R^{11}$, $OPOR^{11}R^{12}$ or $OPSR^{11}R^{12}$ by reaction of cyclohexanedione derivatives of the formula III with alkylating, sulfonylating or phosphonylating agents IVα, IVβ, IVγ or IVδ.

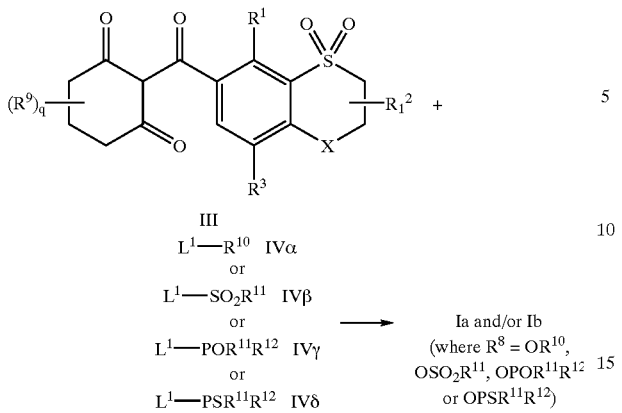

III

L¹—R¹⁰   IVα
or
L¹—SO₂R¹¹   IVβ
or
L¹—POR¹¹R¹²   IVγ
or
L¹—PSR¹¹R¹²   IVδ

⟶ Ia and/or Ib
(where $R^8 = OR^{10}$, $OSO_2R^{11}$, $OPOR^{11}R^{12}$ or $OPSR^{11}R^{12}$)

$L^1$ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula IVα, IVβ, IVγ or IVδ can be employed directly, such as, for example, in the case of the carbonyl halides, or be generated in situ, for example activated carboxylic acids (using carboxylic acid and dicyclohexylcarbodiimide, etc.).

The starting materials are usually employed in equimolar amounts. However it can also be advantageous to employ one component or the other in excess.

It may be advantageous to carry out the reactions in the presence of a base. It is advantageous to employ the starting materials and the base in equimolar amounts. In certain cases, an excess of base, for example 1.5 to 3 molar equivalents, may be advantageous.

Suitable bases include tertiary alkylamines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide, or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide or esters, such as ethyl acetate, or mixtures of these.

The reaction temperature is usually in the range from 0° C. to the boiling point of the reaction mixture.

Work-up to afford the product can be carried out in a manner known per se.

C. Preparation of compounds of the formula I where $R^8=OR^{10}$, $SR^{10}$, $POR^{11}R^{12}$, $NR^{13}R^{14}$, $ONR^{14}R^{14}$, N-bonded heterocyclyl or O—(N-bonded heterocyclyl) by reaction of compounds of the formula I where $R^8$=halogen, $OSO_2R^{11}$ (Iα) with compounds of the formula Vα, Vβ, Vγ, Vδ, Vε, Vη or Vθ, if appropriate in the presence of a base or with prior salt formation.

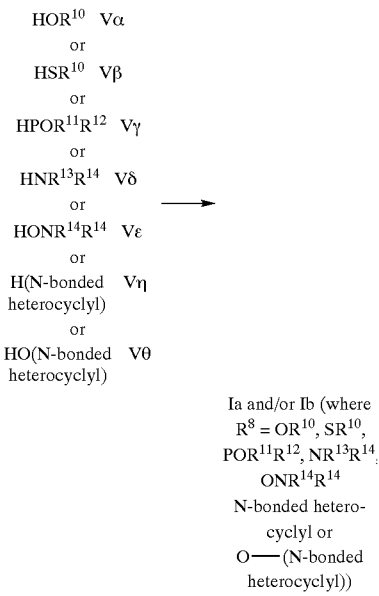

Ia and/or Ib
(where $R^8$ = halogen, $OSO_2R^{11}$) +

HOR¹⁰   Vα
or
HSR¹⁰   Vβ
or
HPOR¹¹R¹²   Vγ
or
HNR¹³R¹⁴   Vδ
or
HONR¹⁴R¹⁴   Vε
or
H(N-bonded heterocyclyl)   Vη
or
HO(N-bonded heterocyclyl)   Vθ

⟶

Ia and/or Ib (where $R^8 = OR^{10}$, $SR^{10}$, $POR^{11}R^{12}$, $NR^{13}R^{14}$, $ONR^{14}R^{14}$
N-bonded heterocyclyl or
O—(N-bonded heterocyclyl))

The starting materials are usually employed in equimolar amounts. However it can also be advantageous to employ one component or the other in excess.

It may be advantageous to carry out the reactions in the presence of a base. It is advantageous to employ the starting materials and the base in equimolar amounts. In certain cases, an excess of base, for example 1.5 to 3 molar equivalents based on Ia and/or Ib (where $R^8$=halogen), may be advantageous.

Suitable bases include tertiary alkylamines, such as tertiary alkylamines [sic], such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium methoxide [sic], potassium tert-butoxide, or alkali metal hydrides, for example sodium hydride. Preference is given to using sodium hydroxide or potassium tert-butoxide.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or mixtures of these.

In general, the reaction temperature is in the range from 0° C. to the boiling point of the reaction mixture.

Work-up to give the product can be carried out in a manner known per se.

D. Preparation of compounds of the formula I where $R^8=SOR^{11}$, $SO_2R^{11}$ by reaction of compounds of the formula I where $R^8=SR^{11}$ (Iβ) with an oxidizing agent.

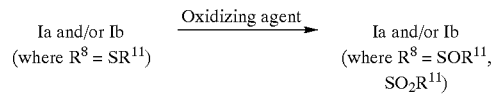

Ia and/or Ib (where $R^8 = SR^{11}$) —Oxidizing agent→ Ia and/or Ib (where $R^8 = SOR^{11}$, $SO_2R^{11}$)

Suitable oxidizing agents are, for example, m-chloroperbenzoic acid, peroxoacetic acid, trifluoroperoxoacetic acid, hydrogen peroxide, if appropriate in the presence of a catalyst such as tungstate.

The starting materials are usually employed in equimolar amounts. However it can also be advantageous to employ one component or the other in excess.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl tert-butyl ether, tetrahydrofuran or dioxan, polar aprotic solvents, such as acetonitrile or dimethylformamide, or esters, such as ethyl acetate, or mixtures of these.

The reaction temperature is usually in the range from 0° C. to the boiling point of the reaction mixture.

Work-up to afford the product can be carried out in a manner known per se.

Depending on the reaction conditions, the compounds Ia, Ib or mixtures thereof can be formed. The mixtures can be separated by classic separation methods, such as, for example crystallization, chromatography, etc.

The cyclohexanedione derivatives of the formula III are known or can be prepared by processes known per se (for example DE 19 532 311), for example by reacting cyclohexanones of the formula VI with an activated benzoic acid VIIa or a benzoic acid VIIb, which is preferably activated in situ, to give the acylation product, and subsequent rearrangement.

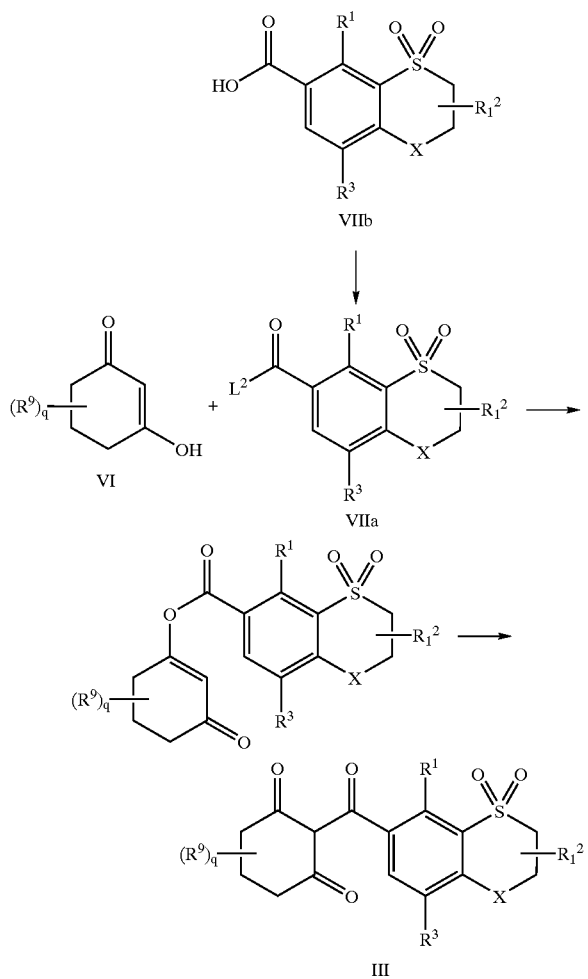

$L^2$ is a nucleophilically replaceable leaving group, such as halogen, for example bromine or chlorine, hetaryl, for example imidazolyl or pyridyl, carboxylate, for example acetate or trifluoroacetate, etc.

The activated benzoic acid VIIa can be employed directly, as in the case of the benzoyl halides, or be generated in situ, for example using dicyclohexylcarbodiimide, triphenylphosphine/azodicarboxylic ester, 2-pyridine disulfide/triphenylphosphine, carbonyldiimidazole, etc.

It may be advantageous to carry out the acylation reaction in the presence of a base. It is advantageous to employ the starting materials and the auxiliary base in equimolar amounts. In certain cases, a small excess of the auxiliary base, for example 1.2 to 1.5 molar equivalents based on VII, may be advantageous.

Suitable auxiliary bases include tertiary alkylamines, pyridine and alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide or esters, such as ethyl acetate, or mixtures of these.

If benzoyl halides are employed as activated carboxylic acid component, it may be advantageous to cool the reaction mixture to 0–10° C. when adding this reactant. Stirring is then continued at 20–100° C., preferably at 25–50° C., until the reaction has ended. Work-up is carried out in a conventional manner; for instance, the reaction mixture is poured into water and the product of value is extracted. Suitable solvents for this purpose are in particular methylene chloride, diethyl ether and ethyl acetate. After drying of the organic phase and removal of the solvent, the crude ester can be used for the rearrangement without any further purification.

The rearrangement of the esters to give the compounds of the formula III is advantageously carried out at from 20 to 100° C. in a solvent and in the presence of a base using, if appropriate, a cyano compound as catalyst.

Suitable solvents are, for example, acetonitrile, methylene chloride, 1,2-dichloroethane, dioxan, ethyl acetate, toluene or mixtures of these. Preferred solvents are acetonitrile and dioxan.

Suitable bases are tertiary amines such as triethylamine, aromatic amines such as pyridine or alkali metal carbonates, such as sodium carbonate or potassium carbonate, which are preferably employed in equimolar amounts or up to a four-fold excess, based on the ester. Preference is given to using triethylamine or alkali metal carbonate, preferably in double the equimolar amount based on the ester.

Suitable cyano compounds are inorganic cyanides, such as sodium cyanide or potassium cyanide, and organic cyano compounds, such as acetone cyanohydrin and trimethylsilyl cyanide. They are employed in an amount of from 1 to 50 mol percent, based on the ester. Preference is given to using acetone cyanohydrin or trimethylsilyl cyanide, for example in an amount of from 5 to 15, preferably 10, mol percent, based on the ester.

Work-up can be carried out in a manner known per se. The reaction mixture is acidified, for example with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated.

The benzoyl halides of the formula VIIa (where $L^2$=Cl, Br) can be prepared in a manner known per se by reacting the benzoic acids of the formula VIIb with halogenating agents such as thionyl chloride, thionyl bromide, phosgene, diphosgene, triphosgene, oxalyl chloride or oxalyl bromide.

The benzoic acids of the formula VIIb can be prepared in a known manner from the corresponding esters by acid or basic hydrolysis.

PREPARATION EXAMPLES

1–Chloro-2-(8-chloro-4,4-dimethyl-1,1-dioxothiochroman-7-yl)carbonylcyclohex-1-en-3-one (Compound 3.2)

Step a) Methyl 3-(3-Methyl-2-butenylthio)-2-chlorobenzoate 37.2 g (0.27 mol) of potassium carbonate were added to 80.3 g (0.27 mol) of methyl 3-thio-2-chlorobenzoate in 500 ml of acetone, 40.2 g (0.27 mol) of 3-methyl-2-butenyl bromide were added dropwise and the reaction mixture was stirred at room temperature for 3 hours. The solvent was distilled off, the residue was taken up in water/ethyl acetate and the organic phase was dried, filtered off and concentrated. The brown oil that remained was chromatographed over silica gel using ethyl acetate/cyclohexane.

Yield : 63.4 g (86.9%) yellow oil. $^1$H NMR (CDCl$_3$, δ in ppm): 7.52 (d,1H); 7.32 (d,1H); 7.26 (t,1H); 5.26 (m,1H); 3.90 (s,3H), 3.49 (d,2H); 2.60 (s,3H); 1.70 (s,3H); 1.59 (s,3H).

Step b) Methyl 8-Chloro-4,4-dimethylthiochroman-7-carboxylate 63.4 g (0.234 mol) of methyl 3-(3-methyl-2-butenylthio)-2-chlorobenzoate were dissolved in 600 ml of methylene chloride, and 94 g (0.94 mol) of conc. sulfuric acid were added dropwise at 0° C. This solution was stirred for 30 minutes and then poured into ice-water, and the organic phase was separated off, dried and concentrated. The resulting orange oil (57.1 g) was used for the next step without any further purification.

$^1$H NMR (CDCl$_3$, δ in ppm): 7.40 (d,1H); 7.32 (d,1H); 3.90 (s,3H); 3.05 (m,2H); 1.98 (m,1H); 1.32 (s,6H).

Step c) 8-Chloro-4,4-dimethylthiochroman-7-carboxylic Acid 53.1 g of the crude methyl 8-chloro-4,4-dimethylthiochroman-7-carboxylate were initially charged in 500 ml of a 1:1 water/methanol mixture, and 11.8 g (0.29 mol) of sodium hydroxide were added. The solution was then heated under reflux for 3 hours. After cooling, the organic solvent was removed and the residue was diluted with 200 ml of water and acidified with cooling using conc. hydrochloric acid. The precipitate was filtered off with suction, washed with acetic acid and water and dried.

Yield: 27.1 g Melting point: 227° C.

Step d) 8-Chloro-4,4-dimethyl-1,1-dioxothiochroman-7-carboxylic Acid 27.1 g (0.106 mol) of 8-chloro-4,4-dimethylthiochroman-7-carboxylic acid were dissolved in 200 ml of acetic acid, and a spatula tip of sodium tungstate was added. At 50–60° C., 26.3 g (0.23 mol) of 30% strength hydrogen peroxide were added dropwise, the solution was stirred at 50° C. for another 2 hours, then stirred into ice-water, and the precipitated white needles were filtered off, washed with water and dried.

Yield: 26.0 g (85.3%) Melting point: 252° C.

Step e) 8-Chloro-4,4-dimethyl-1,1-dioxothiochroman-7-carbonyl Chloride 26.0 g (0.09 mol) of 8-chloro-4,4-dimethyl-1,1-dioxothiochroman-7-carboxylic acid were dissolved in 200 ml of toluene, and three drops of dimethylformamide were added. 11.8 g (0.099 mol) of thionyl chloride were added dropwise, the mixture was heated to reflux for three hours and the solvent was then removed. This gave a colorless oil (yield 27.5 g) which was directly employed for the next step.

Step f) 2-(8-Chloro-4,4-dimethyl-1,1-dioxothiochroman-7-yl)carbonyl-1,3-cyclohexanedione 7.8 g (0.07 mol) of cyclohexane-1,3-dione and 21.2 g (0.07 mol) of triethylamine were dissolved in 50 ml of acetonitrile, and 20.0 g (0.07 mol) of 8-chloro-4,4-dimethyl-1,1-dioxothiochroman-7-carbonyl chloride in 200 ml of acetonitrile were added dropwise. The mixture was stirred at room temperature for two hours, 0.5 ml of trimethylsilyl cyanide were added dropwise, the mixture was then heated at 40° C. for three hours, the solvent was removed and the residue was taken up in 2% strength sodium bicarbonate solution and extracted once each with ethyl acetate and diethyl ether. The aqueous phase was then adjusted to pH 3 using conc. hydrochloric acid and the precipitate was filtered off, washed with water and dried.

Yield: 20.3 g (80.3%) of cream-colored crystals Melting point: 165° C.

Step g) 1-Chloro-2-(8-chloro-4,4-dimethyl-1,1-dioxothiochroman-7-yl)carbonylcyclohex-1-en-3-one (Compound 3.2)

2.0 g (5.2 mmol) of 2-(8-chloro-4,4-dimethyl-1,1-dioxothiochroman-7-yl)carbonyl-1,3-cyclohexanedione were dissolved in 30 ml of methylene chloride and 2.2 g (17.3 mmol) of oxalyl chloride and 2 drops of dimethylformamide were added. After 1 hour of stirring at 25° C., the solvent was removed. This gave 2.1 g of colored crystals.

2-(8-Chloro-4,4-dimethyl-1,1-dioxothiochroman-7-yl)carbonyl-1-(4-chlorophenylthio)cyclohex-1-en-3-one (Compound 3.6)

0.8 g (2 mmol) of 1-chloro-2-(8-chloro-4,4-dimethyl-1,1-dioxothiochroman-7-yl)carbonylcyclohex-1-en-3-one was dissolved in 10 ml of tetrahydrofuran and 0.29 g (2 mmol) of 4-chlorothiophenol and 0.22 g (2.2 mmol) of triethylamine were added dropwise. The mixture was stirred at 25° C. for 2 hours, stirred into water, extracted with ethyl acetate and the organic phases were extracted with 1N hydrochloric acid and dried, and the solvent was removed. This gave 0.9 g of beige crystals.

2-(8-Chloro-4,4-dimethyl-1,1-dioxothiochroman-7-yl)carbonyl-1-(4-chlorophenylsulfonyl)cyclohex-1-en-3-one (Compound 3.4)

0.5 g (0.98 mmol) of 2-(8-chloro-4,4-dimethyl-1,1-dioxothiochroman-7-yl)carbonyl-1-(4-chlorophenylthio) cyclohex-1-en-3-one were dissolved in 20 ml of methylene chloride and 0.68 g (2.16 mmol) of 3-chloroperbenzoic acid (55% strength) were added. The mixture was stirred at 25° C. for 16 hours, diluted with more methylene chloride, washed with sodium bisulfite solution and sodium bicarbonate solution and dried, and the solvent was removed. This gave 0.5 g of cream-colored crystals.

2-(8-Chloro-4,4-dimethyl-1,1-dioxothiochroman-7-yl)carbonyl-1-phenylthiocyclohex-1-en-3-one (Compound 3.7)

0.7 g (1.75 mmol) of 1-chloro-2-(8-chloro-4,4-dimethyl-1,1-dioxothiochroman-7-yl)carbonylcyclohex-1-en-3-one were dissolved in 10 ml of tetrahydrofuran, and 0.19 g (1.75 mmol) of thiophenol and 0.19 g (1.92 mmol) of triethylamine were added dropwise. The mixture was stirred at 25° C. for two hours and then stirred into water, extracted with ethyl acetate and the organic phases were extracted with 1N hydrochloric acid, dried and concentrated. This gave 0.8 g of beige crystals.

2-(8-Chloro-4,4-dimethyl-1,1-dioxothiochroman-7-yl)carbonyl-1-phenylsulfonylcyclohex-1-en-3-one (Compound 3.5)

0.4 g (0.84 mmol) of 2-(8-chloro-4,4-dimethyl-1,1-dioxothiochroman-7-yl)carbonyl-1-phenylthiocyclohex-1-en-3-one was dissolved in 20 ml of methylene chloride, and 0.66 g (2.16 mmol) of 3-chloroperbenzoic acid (55% strength) was added. The mixture was stirred at 25° C. for 16 hours, diluted with more methylene chloride, washed with sodium bisulfite solution and sodium bicarbonate solution and dried, and the solvent was removed. This gave 0.4 g of cream-colored crystals.

2-(8-Chloro-4,4-dimethyl-1,1-dioxothiochroman-7-yl)carbonyl-1-ethylthiocyclohex-1-en-3-one (Compound 3.8)

0.7 g (1.75 mmol) of 1-chloro-2-(8-chloro-4,4-dimethyl-1,1-dioxothiochroman-7-yl)carbonylcyclohex-1-en-3-one is dissolved in 20 ml of tetrahydrofuran, and 0.11 g (1.75 mmol) of ethanethiol and 0.19 g (1.92 mmol) of triethylamine were added dropwise. The mixture was stirred at 25° C. for 2 hours, stirred into water, extracted with ethyl acetate and the organic phases were extracted with 1N hydrochloric acid and dried and the solvent was removed. This gave 0.4 g of beige crystals.

2-(8-Chloro-4,4-dimethyl-1,1-dioxothiochroman-7-yl)carbonyl-1-ethylsulfonylcyclohex-1-en-3-one (Compound 3.9)

0.2 g (0.47 mmol) of 2-(8-chloro-4,4-dimethyl-1,1-dioxothiochroman-7-yl)carbonyl)-1-ethylthiocyclohex-1-en-3-one [sic] was dissolved in 20 ml of methylene chloride, and 0.37 g (1.17 mmol) of 3-chloroperbenzoic acid (55% strength) was added. The mixture was stirred at 25° C. for 16 hours, diluted with more methylene chloride, washed with sodium bisulfite solution and sodium bicarbonate solution, and dried, and the solvent was removed. This gave 0.17 g of cream-colored crystals.

2-(8-Chloro-4,4-dimethyl-1,1-dioxothiochroman-7-yl)carbonyl-1-(N,O-dimethylhydroxylamino)cyclohex-1-en-3-one (Compound 3.10)

0.5 g (1.25 mmol) of 1-chloro-2-(8-chloro-4,4-dimethyl-1,1-dioxothiochroman-7-yl)carbonylcyclohex-1-en-3-one was dissolved in 10 ml of tetrahydrofuran, and 0.13 g (1.37 mmol) of N,O-dimethylhydroxylamine hydrochloride and 0.28 g (2.74 mmol) of triethylamine were added dropwise. The mixture was stirred at 25° C. for 25 hours, stirred into water and extracted with ethyl acetate, the organic phases were extracted with 1N hydrochloric acid and dried and the solvent was removed. This gave 0.4 g of beige crystals.

1-(Phenylcarbonyloxy)-2-(4,4,8-trimethyl-1,1-dioxothiochroman-7-yl)carbonylcyclohex-1-en-3-one (Compound 3.22)

Step a) Methyl 3-(3-Methyl-2-butenylthio)-2-methylbenzoate 37.9 g (0.27 mol) of potassium carbonate and 43.5 g (0.275 mol) of 3-methyl-2-butenyl bromide were added dropwise to 50 g (0.275 mol) of methyl 3-thio-2-methylbenzoate in 250 ml of acetone, and the mixture was stirred at room temperature for 10 hours. The solvent was distilled off, the residue was taken up in water/ethyl acetate and the organic phase was dried, filtered off and concentrated.

Yield: 67.9 g (98.9%) yellow oil. $^1$H NMR (CDCl$_3$, δ in ppm): 7.63 (d,1H); 7.41 (d,1H); 7.16 (t,1H); 5.25 (m,1H); 3.90 (s,3H); 3.49 (d,2H); 2.60 (s,3H); 1.70 (s,3H); 1.56 (s,3H).

Step b) Methyl 4,4,8-Trimethylthiochroman-7-carboxylate 67.9 g (0.27 mol) of methyl 3-(3-methyl-2-butenylthio)-2-methylbenzoate were dissolved in 600 ml of methylene chloride, 206.4 g (1.09 mol) of titanium tetrachloride in 600 ml of methylene chloride were added dropwise at from −5 to 0° C. and the mixture was stirred at 0° C. for another 3 hours. The mixture was subsequently stirred into 1.5 kg of ice and 500 ml of saturated ammonium chloride solution, the organic phase was separated off and dried and the solvent was removed. This gave 62.9 g of a yellow oil which was directly employed for the next step. For product characterization, a sample was chromatographed over silica gel (mobile phase: cyclohexane/ethyl acetate=10/1).

Melting point: 63° C.

Step c) 4,4,8-Trimethylthiochroman-7-carboxylic Acid 62.9 g of methyl 4,4,8-trimethylthiochroman-7-carboxylate were initially charged in 600 ml of a 1:1 water/methanol mixture, and 15.1 g (0.377 mol) of sodium hydroxide were added. The solution was then heated at reflux for 3 hours, the organic solvent was removed, 200 ml of water were added and the mixture was acidified with cooling using conc. hydrochloric acid. The precipitate was filtered off with suction, washed with water and dried.

Yield: 57.2 g Melting point: 212° C.

Step d) 4,4,8-Trimethyl-1,1-dioxothiochroman-7-carboxylic Acid 57.2 g (0.24 mol) of 4,4,8-trimethylthiochroman-7-carboxylic acid were dissolved in 500 ml of glacial acetic acid, and a spatula tip of sodium tungstate was added. At 50–60° C., 60.4 g (0.53 mol) of 30% strength hydrogen peroxide were added dropwise, the mixture was stirred at 50° C. for another three hours and then stirred into ice-water and the precipitated white needles were filtered off, washed with water and dried.

Yield: 47.2 g (72.7%) Melting point: 280° C. (decomposition)

Step e) 4,4,8-Trimethyl-1,1-dioxothiochroman-7-carbonyl Chloride 20.0 g (0.075 mol) of 4,4,8-trimethyl-1,1-dioxothiochroman-7-carboxylic acid were dissolved in 200 ml of toluene and three drops of dimethylformamide and 10.7 g (0.09 mol) of thionyl chloride were added. The mixture was heated under reflux for three hours, the solvent was removed and the colorless oil that remained (yield 21.3 g) was directly employed for the next step.

Step f) 2-(4,4,8-Trimethyl-1,1-dioxothiochroman-7-yl)carbonyl-1,3-cyclohexanedione 2.1 g (19 mmol) of 1,3-cyclohexanedione and 4.9 g (49 mmol) of triethylamine were dissolved in 50 ml of acetonitrile, and 5.0 g (19 mmol) of 4,4,8-trimethyl-1,1-dioxothiochroman-7-carbonyl chloride in 50 ml of acetonitrile were added dropwise. The mixture was stirred at room temperature for fourteen hours, 0.05 ml of trimethylsilyl cyanide was added dropwise, the mixture was stirred at room temperature for 4 hours, the solvent was removed and the residue was taken up in 2% strength sodium bicarbonate solution and extracted once each with ethyl acetate and diethyl ether. The aqueous phase was adjusted to pH 3 using conc. hydrochloric acid and the precipitate was filtered off, washed with water and dried.

Yield: 5.1 g (74%) colorless crystals Melting point: 165° C.

Step g) 1-(Phenylcarbonyloxy)-2-(4,4,8-trimethyl-1,1-dioxothiochroman-7-yl)carbonylcyclohex-1-en-3-one (Compound 3.22)

0.8 g (2.2 mmol) of 2-(4,4,8-trimethyl-1,1-dioxothiochroman-7-yl)carbonyl-1,3-cyclohexanedione was dissolved in 10 ml of methylene chloride, and 0.17 g (2.2 mmol) of pyridine and 0.31 g (2.2 mmol) of benzoyl chloride was added. The mixture was stirred at room temperature for 2 hours, water was added, and the organic phase was separated off, extracted with 2 N hydrochloric acid and dried. The solvent was subsequently distilled off and the residue was chromatographed over silica gel.

Yield: 0.35 g (47%) colorless crystals Melting point: 189° C. (decomposition)

1-Chloro-2-[(8-methyl-2,3-dihydro-1,1,4,4-tetraoxobenz[1,4]dithiyn-7-yl)carbonyl]-4,4,6,6-tetramethyl-1-cyclohexene-3,5-dione (Compound 4.1)

Step a) Methyl 3-(2-Bromoethylthio)-2-methylbenzoate 30.3 g (0.22 mol) of potassium carbonate were added to 40.0 g (0.22 mol) of methyl 3-thio-2-methylbenzoate in 500 ml of acetone, and 82.6 g (0.22 mol) of 1,2-dibromoethane were added dropwise. The mixture was stirred at room temperature for 10 hours, the solvent was distilled off, the residue was taken up in water/ethyl acetate and the organic phase was dried and concentrated. The oil that remained was chromatographed over silica gel using ethyl acetate/cyclohexane=1/10.

Yield: 42.7 g (67.2%) colorless crystals. $^1$H NMR (CDCl$_3$, δ in ppm): 7.68 (d,1H); 7.51 (d,1H); 7.20 (t,1H); 3.90 (s,3H); 3.41 (m,2H); 3.25 (m,2H); 2.62 (s,3H).

Step b) Methyl 3-(2-Methylsulfonylthioethylthio)-2-methylbenzoate 33.2 g (0.22 mol) of potassium methylsulfonylthiolate were added to 42.7 g (0.148 mol) of methyl 3-(2-bromoethylthio)-2-methylbenzoate in 400 ml of ethanol, and the mixture was heated under reflux for five hours. The solvent was removed and the residue was taken up in water/ethyl acetate, dried and concentrated. The oil that remained was chromatographed over silica gel using ethyl acetate/cyclohexane=1/4.

Yield: 33.2 g (67.2%) yellow oil. Melting point: 55° C.

Step c) Methyl 8-Methyl-2,3-dihydrobenz[1,4]dithiin-7-carboxylate 49.2 g (0.154 mol) of methyl 3-(2-methylsulfonylthioethylthio)-2-methylbenzoate were dissolved in 500 ml of methylene chloride, 80.2 g (0.308 mol) of tin tetrachloride were added and the mixture was heated under reflux for 3 hours and then stirred at room temperature for 10 hours. The mixture was then washed with water and saturated sodium bicarbonate solution and the organic phase was separated off, dried and concentrated. The oil that remained was chromatographed over silica gel using ethyl acetate/cyclohexane=1/10.

Yield: 17.1 g (46.3%) colorless crystals Melting point: 57° C.

Step d) 8-Methyl-2,3-dihydrobenz[1,4]dithiin-7-carboxylic Acid 9.6 g (0.04 mol) of methyl 8-methyl-2,3-dihydrobenz[1,4]dithiin-7-carboxylate were initially charged in 100 ml of a 1:1 mixture of water/methanol, and 2.4 g (0.06 mol) of sodium hydroxide were added. The mixture was heated under reflux for two hours and the organic solvent was then distilled off, 200 ml of water were added and the mixture was then acidified with cooling using conc. hydrochloric acid. The precipitate was filtered off with suction, washed with water and dried.

Yield: 8.1 g (89.6%) colorless crystals Melting point: 175° C.

Step e) 8-Methyl-2,3-dihydro-1,1,4,4-tetraoxobenz[1,4]dithiin-7-carboxylic Acid 19.4 g (0.086 mol) of 8-methyl-2,3-dihydrobenz[1,4]dithiin-7-carboxylic acid were dissolved in 200 ml of acetic acid and a spatula tip of sodium tungstate was added. At 50–60° C., 42.8 g (0.38 mol) of 30% strength hydrogen peroxide were then added dropwise. After five hours of stirring at 50° C., the mixture was cooled and stirred into ice-water and the precipitated white needles were filtered off, washed with water and dried.

Yield: 21.7 g (87.2%) Melting point: 282° C.

Step f) 8-Methyl-2,3-dihydro-1,1,4,4-tetraoxobenz[1,4]dithiin-7-carbonyl Chloride 10.0 g (0.0345 mol) of 8-methyl-2,3-dihydro-1,1,4,4-tetraoxobenz[1,4]dithiin-7-carboxylate were dissolved in 100 ml of toluene and two drops of dimethylformamide and subsequently 4.5 g (0.038 mol) of thionyl chloride were added. The mixture was stirred at reflux for four hours and then concentrated. The colorless oil that remained (yield 10.6 g) could be employed directly for the next step.

Step g) 2-(8-Methyl-2,3-dihydro-1,1,4,4-tetraoxobenz[1,4]dithiin-7-yl)carbonyl-4,4,6,6-tetramethyl-5-oxo-1,3-cyclohexanedione 2.95 g (16.2 mmol) of 4,4,6,6-tetramethyl-5-oxo-1,3-cyclohexanedione and 4.9 g (4.9 mmol) of triethylamine were dissolved in 50 ml of acetonitrile and 5.0 g (16.2 mmol) of 8-methyl-2,3-dihydro-1,1,4,4-tetraoxobenz[1,4]dithiin-7-carbonyl chloride in 50 ml of acetonitrile were added dropwise. The mixture was stirred at room temperature for fourteen hours, 0.05 ml of trimethylsilyl cyanide was added dropwise, the mixture was stirred at room temperature for four hours, the solvent was removed and the residue was taken up in 2% strength sodium bicarbonate solution and extracted once each with ethyl acetate and diethyl ether. The aqueous phase was adjusted to pH 3 using conc. hydrochloric acid and the precipitate was filtered off, washed with water and dried.

Yield: 4.8 g (65%) colorless crystals Melting point: 146° C. (decomposition)

Step h) 1-Chloro-2-(8-methyl-2,3-dihydro-1,1,4,4-tetraoxobenz[1,4]dithiin-7-yl)carbonyl-4,4,6,6-tetramethyl-1-cyclohexene-3,5-dione (Compound 4.1)

0.5 g (1.1 mmol) of 2-(8-methyl-2,3-dihydro-1,1,4,4-tetraoxobenz[1,4]dithiin-7-yl)carbonyl-4,4,6,6-tetramethyl-1,3,5-cyclohexanetrione was dissolved in 10 ml of methylene chloride and 0.28 g (2.2 mmol) of oxalyl chloride and 2 drops of dimethylformamide were added. The mixture was stirred at 25° C. for one hour and the solvent was then removed.

Yield: 0.3 g (58%) colorless crystals

TABLE 3

Ia (where X = CR⁴R⁵ and I = O)

| No. | $R^1$ | $R^3$ | $R^4$ | $R^5$ | $R^8$ | $(R^9)_q$ | m.p. [° C.]; $^1$H NMR [CDCl$_3$; δ in ppm]; MS[$^m/_z$] |
|---|---|---|---|---|---|---|---|
| 3.1 | CH$_3$ | H | CH$_3$ | CH$_3$ | Cl | (q = 0) | 208 (decomposition) |
| 3.2 | Cl | H | CH$_3$ | CH$_3$ | Cl | (q = 0) | 218 (decomposition) |
| 3.3 | CH$_3$ | H | OCH$_3$ | H | Cl | 4,4,6,6-tetramethyl-5-oxo | 145 |
| 3.4 | Cl | H | CH$_3$ | CH$_3$ | SO$_2$(4-Cl—C$_6$H$_4$) | (q = 0) | 235 (decomposition) |
| 3.5 | Cl | H | CH$_3$ | CH$_3$ | SO$_2$C$_6$H$_5$ | (q = 0) | 239 (decomposition) |
| 3.6 | Cl | H | CH$_3$ | CH$_3$ | S(4-Cl—C$_6$H$_4$) | (q = 0) | 245 (decomposition) |
| 3.7 | Cl | H | CH$_3$ | CH$_3$ | SC$_6$H$_5$ | (q = 0) | 199 (decomposition) |
| 3.8 | Cl | H | CH$_3$ | CH$_3$ | SO$_2$C$_2$H$_5$ | (q = 0) | 105 (decomposition) |
| 3.9 | Cl | H | CH$_3$ | CH$_3$ | SC$_2$H$_5$ | (q = 0) | 191 |
| 3.10 | Cl | H | CH$_3$ | CH$_3$ | N(OCH$_3$)CH$_3$ | (q = 0) | 88 (decomposition) |
| 3.11 | CH$_3$ | H | CH$_3$ | CH$_3$ | SO$_2$(4-Cl—C$_6$H$_4$) | (q = 0) | 260 (decoinposition) |
| 3.12 | CH$_3$ | H | CH$_3$ | CH$_3$ | SO$_2$C$_2$H$_5$ | (q = 0) | 115 (decomposition) |
| 3.13 | CH$_3$ | H | CH$_3$ | CH$_3$ | S(4-Cl—C$_6$H$_4$) | (q = 0) | 244 (decomposition) |
| 3.14 | CH$_3$ | H | CH$_3$ | CH$_3$ | SC$_6$H$_5$ | (q = 0) | 222 (decomposition) |
| 3.15 | CH$_3$ | H | CH$_3$ | CH$_3$ | SO$_2$C$_6$H$_5$ | (q = 0) | 258 (decomposition) |
| 3.16 | CH$_3$ | H | CH$_3$ | CH$_3$ | SC$_2$H$_5$ | (q = 0) | 163 (decomposition) |
| 3.17 | CH$_3$ | H | CH$_3$ | CH$_3$ | N(OCH$_3$)CH$_3$ | (q = 0) | 204 (decomposition) |
| 3.18 | CH$_3$ | H | CH$_3$ | CH$_3$ | 4-morpholinyl | (q = 0) | 7.27 (m, 2H); 3.86 (m, 4H); 3.50 (m, 4H); 3.40 (m, 2H); 2.78 (s, 3H); 2.75 (m, 2H); 2.31 (m, 4H); 1.98 (m, 2H); 1.38 (s, 6H) |
| 3.19 | CH$_3$ | H | CH$_3$ | CH$_3$ | 1-pyrolidinyl | (q = 0) | 126 (decomposition) |
| 3.20 | CH$_3$ | H | CH$_3$ | CH$_3$ | 1-pyrazolyl | (q = 0) | 242 (decomposition) |
| 3.21 | CH$_3$ | H | CH$_3$ | CH$_3$ | 1-(1,2,4)triazolyl | (q = 0) | 208 (decomposition) |
| 3.22 | CH$_3$ | H | CH$_3$ | CH$_3$ | OCOC$_6$H$_5$ | (q = 0) | 189 (decomposition) |
| 3.23 | CH$_3$ | H | OCH$_3$ | H | N(OCH$_3$)CH$_3$ | 4,4,6,6-tetramethyl-5-oxo | 7.20 (d, 1H); 7.12 (d, 1H); 4.18 (m, 1H); 3.83 (m, 1H); 3.65 (s, 3H); 3.41 (s, 3H); 3.27 (m, 4H); 2.85 (s, 3H); 2.60 (m, 2H); 1.60 (s, 3H); 1.57 (s, 3H); 1.38 (s, 3H); 1.32 (s, 3H); |
| 3.24 | CH$_3$ | H | CH$_3$ | CH$_3$ | 2-tetrahydroisoxazolyl | (q = 0) | 185 |
| 3.25 | Cl | H | CH$_3$ | CH$_3$ | 2-tetrahydroisoxazolyl | (q = 0) | 158 |
| 3.26 | Cl | H | CH$_3$ | CH$_3$ | SCH$_2$CH(CH$_3$)CH$_2$CH$_3$ | (q = 0) | 469.1 (MS) |
| 3.27 | Cl | H | CH$_3$ | CH$_3$ | SCH$_2$CH$_2$CH$_3$ | (q = 0) | 441.0 (MS) |
| 3.28 | Cl | H | CH$_3$ | CH$_3$ | S(CH$_2$)$_4$CH$_3$ | (q = 0) | 469.1 (MS) |
| 3.29 | Cl | H | CH$_3$ | CH$_3$ | SCH$_2$CH(CH$_3$)$_2$ | (q = 0) | 455.0 (MS) |
| 3.30 | Cl | H | CH$_3$ | CH$_3$ | SCH$_2$CF$_3$ | (q = 0) | 481.0 (MS) |
| 3.31 | Cl | H | CH$_3$ | CH$_3$ | S(CH$_2$)$_2$CH(CH$_3$)$_2$ | (q = 0) | 469.1 (MS) |
| 3.32 | Cl | H | CH$_3$ | CH$_3$ | S(CH$_2$)$_5$CH$_3$ | (q = 0) | 483.1 (MS) |
| 3.33 | Cl | H | CH$_3$ | CH$_3$ | S(CH$_2$)$_3$CH$_3$ | (q = 0) | 455.0 (MS) |
| 3.34 | Cl | H | CH$_3$ | CH$_3$ | SCH$_2$CH$_3$ | (q = 0) | 427.0 (MS) |
| 3.35 | Cl | H | CH$_3$ | CH$_3$ | SCH$_2$CH=CH$_2$ | (q = 0) | 439.0 (MS) |
| 3.36 | Cl | H | CH$_3$ | CH$_3$ | SCH$_2$C(CH$_3$)=CCl$_2$ | (q = 0) | 521.9 (MS) |
| 3.37 | Cl | H | CH$_3$ | CH$_3$ | S(CH$_2$)$_2$OCH$_2$CH$_3$ | (q = 0) | 471.0 (MS) |
| 3.38 | Cl | H | CH$_3$ | CH$_3$ | S(CH$_2$)$_2$COCH$_3$ | (q = 0) | 469.0 (MS) |
| 3.39 | Cl | H | CH$_3$ | CH$_3$ | S(CH$_2$)$_2$OCH$_3$ | (q = 0) | 557.0 (MS) |
| 3.40 | Cl | H | CH$_3$ | CH$_3$ | S(CH$_2$)$_2$CO$_2$CH$_2$CH$_3$ | (q = 0) | 499.0 (MS) |
| 3.41 | Cl | H | CH$_3$ | CH$_3$ | SCH$_2$CO$_2$(CH$_2$)$_3$CH$_3$ | (q = 0) | 513.1 (MS) |
| 3.42 | Cl | H | CH$_3$ | CH$_3$ | S(CH$_2$)$_2$CO$_2$CH$_3$ | (q = 0) | 485.0 (MS) |
| 3.43 | Cl | H | CH$_3$ | CH$_3$ | SCH(CH$_3$)CO$_2$CH$_2$CH$_3$ | (q = 0) | 499.0 (MS) |
| 3.44 | Cl | H | CH$_3$ | CH$_3$ | SCH$_2$(6-CH$_3$—C$_6$H$_4$) | (q = 0) | 503.1 (MS) |
| 3.45 | Cl | H | CH$_3$ | CH$_3$ | SCH$_2$(2-furyl) | (q = 0) | 479.0 (MS) |
| 3.46 | Cl | H | CH$_3$ | CH$_3$ | S[4-C(CH$_3$)$_3$—C$_6$H$_4$] | (q = 0) | 531.1 (MS) |
| 3.47 | Cl | H | CH$_3$ | CH$_3$ | S(3-CF$_3$—C$_6$H$_4$) | (q = 0) | 593.0 (MS) |
| 3.48 | Cl | H | CH$_3$ | CH$_3$ | S(4-OCH$_3$—C$_6$H$_4$) | (q = 0) | 505.1 (MS) |
| 3.49 | Cl | H | CH$_3$ | CH$_3$ | S(C$_6$F$_5$) | (q = 0) | 565.0 (MS) |
| 3.50 | Cl | H | CH$_3$ | CH$_3$ | S(4,6-dimethoxy-2-pyrimidinyl) | (q = 0) | 537.1 (MS) |
| 3.51 | Cl | H | CH$_3$ | CH$_3$ | S(4,6-dimethyl-2-pyrimidinyl) | (q = 0) | 505.1 (MS) |
| 3.52 | Cl | H | CH$_3$ | CH$_3$ | S(4-NO$_2$—C$_6$H$_4$) | (q = 0) | 520.0 (MS) |
| 3.53 | Cl | H | CH$_3$ | CH$_3$ | S(3,5-(CF$_3$)$_2$—C$_6$H$_3$) | (q = 0) | 611.0 (MS) |
| 3.54 | Cl | H | CH$_3$ | CH$_3$ | S(3-Cl—4-F—C$_6$H$_3$) | (q = 0) | 527.5 (MS) |
| 3.55 | Cl | H | CH$_3$ | CH$_3$ | S(3-C(CH$_3$)$_3$-6-CH$_3$—C$_6$H$_3$) | (q = 0) | 545.2 (MS) |

TABLE 3-continued

Ia (where X = CR$^4$R$^5$ and I = O)

| No. | R$^1$ | R$^3$ | R$^4$ | R$^5$ | R$^8$ | (R$^9$)$_q$ | m.p. [° C.]; $^1$H NMR [CDCl$_3$; δ in ppm]; MS[$^m/_z$] |
|---|---|---|---|---|---|---|---|
| 3.56 | Cl | H | CH$_3$ | CH$_3$ | SCH$_2$(3-Cl—C$_6$H$_4$) | (q = 0) | 523.5 (MS) |
| 3.57 | Cl | H | CH$_3$ | CH$_3$ | SCH$_2$(2-Cl—C$_6$H$_4$) | (q = 0) | 523.5 (MS) |
| 3.58 | Cl | H | CH$_3$ | CH$_3$ | SCH$_2$(3,4-Cl$_2$—C$_6$H$_3$) | (q = 0) | 557.9 (MS) |
| 3.59 | Cl | H | CH$_3$ | CH$_3$ | SCH$_2$(4-OCH$_3$—C$_6$H$_4$) | (q = 0) | 519.1 (MS) |
| 3.60 | Cl | H | CH$_3$ | CH$_3$ | SCH$_2$(2-F—C$_6$H$_4$) | (q = 0) | 507.0 (MS) |
| 3.61 | Cl | H | CH$_3$ | CH$_3$ | SCH$_2$(2,5-Cl$_2$—C$_6$H$_3$) | (q = 0) | 557.9 (MS) |
| 3.62 | Cl | H | CH$_3$ | CH$_3$ | SCH$_2$(4-F—C$_6$H$_4$) | (q = 0) | 507.0 (MS) |
| 3.63 | Cl | H | CH$_3$ | CH$_3$ | SCH$_2$(4-Cl—C$_6$H$_4$) | (q = 0) | 523.5 (MS) |
| 3.64 | Cl | H | CH$_3$ | CH$_3$ | S(CH$_2$)$_2$(C$_6$H$_5$) | (q = 0) | 503.1 (MS) |
| 3.65 | Cl | H | CH$_3$ | CH$_3$ | SCH$_2$CO$_2$CH$_3$ | (q = 0) | 471.0 (MS) |
| 3.66 | Cl | H | CH$_3$ | CH$_3$ | SCH$_2$CO$_2$CH(CH$_3$)$_2$ | (q = 0) | 499.0 (MS) |
| 3.59 | Cl | H | CH$_3$ | CH$_3$ | SCH$_2$(3-CH$_3$—C$_6$H$_4$) | (q = 0) | 503.1 (MS) |
| 3.60 | Cl | H | CH$_3$ | CH$_3$ | SCH$_2$(C$_6$H$_5$) | (q = 0) | 489.1 (MS) |
| 3.61 | Cl | H | CH$_3$ | CH$_3$ | SCH$_2$(4-CH$_3$—C$_6$H$_4$) | (q = 0) | 503.1 (MS) |
| 3.62 | Cl | H | CH$_3$ | CH$_3$ | SCH$_2$CO$_2$CH$_2$CH$_3$ | (q = 0) | 485.0 (MS) |

TABLE 4

Ia (where X = SO$_2$ and I = O)

| No. | R$^1$ | R$^3$ | R$^8$ | (R$^9$)$_q$ | m.p. [° C.]; |
|---|---|---|---|---|---|
| 4.1 | CH$_3$ | H | Cl | 4,4,6,6-tetramethyl-5-oxo | 118 |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or herbicidal compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the compounds of the formula I may also be used in crops which tolerate the action of herbicides owing to breeding, including genetic engineering methods.

The compounds of the formula I, or the compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, spreading or watering. The use forms depend on the intended purpose; in any case, they should guarantee the finest possible distribution of the active ingredients according to the invention.

The herbicidal compositions comprise a herbicidally effective amount of at least one compound of the formula I or an agriculturally useful salt of I, and auxiliaries which are customary for the formulation of crop protection agents.

Suitable as inert auxiliaries are essentially the following: mineral oil fractions of medium to high boiling point, such as kerosene and diesel oil, furthermore coal tar oils and oils of vegetable or animal origin, aliphatic, cyclic and aromatic hydrocarbons, eg. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the cyclohexenonedioxothiochromanoyl derivatives of the formula I, either as such or dissolved in an oil or solvent, can be homogenized in water by means of a wetting agent, tackifier, dispersant or emulsifier. Alternatively, it is also possible to prepare concentrates comprising active ingredient, wetting agent, tackifier, dispersant or emulsifier and, if desired, solvent or oil, which are suitable for dilution with water.

Suitable surfactants (adjuvants) are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active ingredients together with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

The formulation examples below illustrate the preparation of such compositions:

I. 20 parts by weight of the compound No. 3.1 are dissolved in a mixture composed of 80 parts by weight of alkylated benzene, 10 parts by weight of the adduct of from 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

II. 20 parts by weight of the compound No. 3.2 are dissolved in a mixture composed of 40 parts by weight of cyclohexanone, parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

III. 20 parts by weight of the compound No. 3.4 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active ingredient.

IV. 20 parts by weight of the compound No. 3.8 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

V. 3 parts by weight of the compound No. 3.9 are mixed with 97 parts by weight of finely divided kaolin. This gives a dust which comprises 3% by weight of the active ingredient.

VI. 20 parts by weight of the compound No. 3.18 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 3.23 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 4.1 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre- or post-emergence. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

The rates of application of the compound of the formula I are from 0.001 to 3.0, preferably 0.01 to 1.0, kg/ha of active substance (a.s.), depending on the control target, the season, the target plants and the growth stage.

To widen the spectrum of action and to achieve synergistic effects, the cyclohexenonedioxothiochromanoyl derivatives of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, amino-phosphoric acid and its derivatives, aminotriazoles, anilides, (het) aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitro-anilines, dinitrophenols, diphenyl ethers, dipyridyls, halo-carboxylic acids and their derivatives, ureas, 3-phenyluracils, imidazoles, imidazolinones, N-phenyl-3,4,5,6-tetrahydro-phthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or in combination with other herbicides, or in the form of a mixture with other crop protection agents, for example together with agents for controlling pests or phytopathogenic fungi or bacteria. Also of interest is the miscibility with mineral salt solutions, which are employed for treating nutritional and trace element deficiencies.

Non-phytotoxic oils and oil concentrates may also be added.

USE EXAMPLES

The herbicidal activity of the cyclohexenonedioxothiochromanoyl derivatives of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active ingredients.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The rate of application for the post-emergence treatment was 0.5 or 0.25 kg/ha of a.s. (active substance).

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments belonged to the following species:

| Scientific name | English name |
| --- | --- |
| Chenopodium album | lambsquarters (goosefoot) |
| Echinochloa crus-galli | barnyardgrass |
| Galium aparine | catchweed bedstraw |
| Setaria faberi | giant foxtail |
| Setaria viridis | green foxtail |
| Sinapis alba | white mustard |
| Solanum nigrum | black nightshade |

The compounds 3.2 and 4.1, applied post-emergence, showed very good activity against the abovementioned harmful plants at rates of application of 0.5 and 0.25 kg/ha, respectively.

We claim:

1. A cyclohexenonedioxothiochromanoyl derivative of the formula I

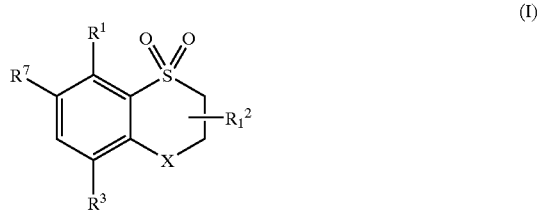

(I)

where:
X is oxygen, sulfur, S=O, $S(=O)_2$, $CR^4R^5$, C=O or $C=NR^6$;
$R^1$ is hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haoalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N,N-di($C_1$–$C_6$-alkyl)aminosulfonyl, N—($C_1$–$C_6$-alkylsulfonyl)amino, N—($C_1$–$C_6$-haloalkylsulfonyl)amino, N—($C_1$–$C_6$-alkyl)-N—($C_1$–$C_6$-alkylsulfonyl)amino or N—($C_1$–$C_6$-alkyl)-N—($C_1$–$C_6$-haloalkylsulfonyl)amino;
$R^2$ is $C_1$–$C_6$-alkyl, $C_1$–$C_6$-haloalkyl, $C_1$–$C_6$-alkoxy or $C_1$–$C_6$-haloalkoxy;
$R^3$ is hydrogen, $C_1$–$C_6$-alkyl or halogen;
$R^4$, $R^5$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, N—$C_1$–$C_6$-alkylamino, N—$C_1$–$C_6$-haloalkylamino, N,N-di-($C_1$–$C_6$-alkyl)amino, N—$C_1$–$C_6$-alkoxyamino, N—($C_1$–$C_6$-alkoxy)-N—($C_1$–$C_6$-alkyl)amino, 1-tetrahydropyrrolyl, 1-piperidinyl, 4-morpholinyl or 1-hexahydropyrazinyl; or
$R^4$ and $R^5$ together form an —O—$(CH_2)_m$—O—, —O—$(CH_2)_m$—S—, —S—$(CH_2)_m$—S— or —O—$(CH_2)_n$— chain which may be substituted by one to three radicals selected from the following group:
halogen, cyano, $C_1$–$C_4$-alkyl, $C_1$–$C_4$-haloalkyl or $C_1$–$C_4$-alkoxycarbonyl; or
$R^4$ and $R^5$ together form a —$(CH_2)_p$— chain which may be interrupted by oxygen or sulfur and/or may be substituted by one to four radicals selected from the following group:

halogen, cyano, $C_1$–$C_4$-alkyl, $C_1$–$C_4$-haloalkyl or $C_1$–$C_4$-alkoxycarbonyl; or $R^4$ and $R^5$ together form a methylidene group which may be substituted by one to two radicals selected from the following group:
halogen, cyano, hydroxyl, formyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$_6$-haloalkylsulfinyl, $C_1$–$C_6$-alkylsulfonyl or $C_1$–$C_6$-haloalkylsulfonyl;

$R^6$ is $C_1$–$C_6$-alkyl, $C_1$–$C_6$-haloalkyl, $C_1$–$C_6$-alkoxy or $C_1$–$C_6$-haloalkoxy;

l is 0 to 4;
m is 2 to 4;
n is 1 to 5;
p is 2 to 5;
$R^7$ is a compound IIa or IIb

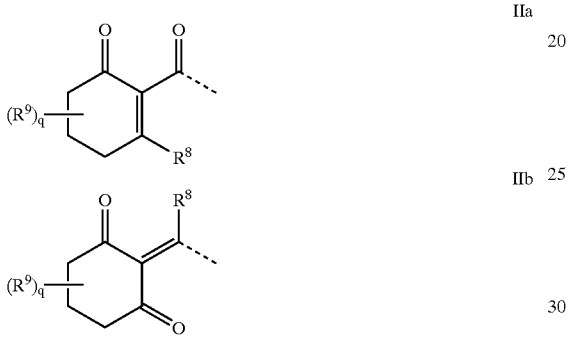

where
$R^8$ is halogen, $OR^{10}$, $SR^{10}$, $SOR^{11}$, $SO_2R^{11}$, $OSO_2R^{11}$, $POR^{11}R^{12}$, $OPOR^{11}R^{12}$, $OPSR^{11}R^{12}$, $NR^{13}R^{14}$, $ONR^{14}R^{14}$, N-bonded heterocyclyl or O—(N-bonded heterocyclyl), where the heterocyclyl radical of the two lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^9$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio) methyl, hydroxyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl; or two radical $R^9$ which are attached to the same carbon together form an —O—($CH_2$)$_m$—O—, —O—($CH_2$)$_m$—S—, —S—($CH_2$)$_m$—S— or —O—($CH_2$)$_n$— chain which may be substituted by one to three radicals selected from the following group:
halogen, cyano, $C_1$–$C_4$-alkyl, $C_1$–$C_4$-haloalkyl or $C_1$–$C_4$-alkoxycarbonyl; or two radicals $R^9$ which are attached to the same carbon together form a —($CH_2$)$_p$— chain which may be interrupted by oxygen or sulfur and/or may be substituted by one to four radicals selected from the following group:
halogen, cyano, $C_1$–$C_4$-alkyl, $C_1$–$C_4$-haloalkyl or $C_1$–$C_4$-alkoxycarbonyl; or two radicals $R^9$ which are attached to the same carbon together form a methylidene group which may be substituted by one to two radicals selected from the following group:
halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl; or two radicals $R^9$ which are attached to the same carbon together with this carbon form a carbonyl group; or two radicals $R^9$ which are attached to different carbons together form a —($CH_2$)$_n$— chain which may be substituted by one to three radicals selected from the following group:
halogen, $C_1$–$C_6$-alkyl, $C_1$–$C_6$-alkoxy, hydroxyl or $C_1$–$C_6$-alkoxycarbonyl;

$R^{10}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N—($C_3$–$C_6$-alkenyl)-N—($C_1$–$C_6$-alkyl)aminocarbonyl, N—($C_3$–$C_6$-alkynyl)-N—($C_1$–$C_6$-alkyl)aminocarbonyl, N—($C_1$–$C_6$-alkoxy)-N—($C_1$–$C_6$-alkyl)aminocarbonyl, N—($C_3$–$C_6$-alkenyl)-N—($C_1$–$C_6$-alkoxy)aminocarbonyl, N—($C_3$–$C_6$-alkynyl)-N—($C_1C_6$-alkoxy)aminocarbonyl, di($C_1$–$C_6$-alkyl) aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl or N,N-di($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di($C_1$–$C_4$-alkyl)amino-$C_1$–$C_4$-alkoxycarbonyl, hydroxycarbonyl, $C_1$–$C_4$-alkylaminocarbonyl, di($C_1$–$C_4$-alkyl) aminocarbonyl, aminocarbonyl, $C_1$–$C_4$-alkylcarbonyloxy or $C_3$–$C_6$-cycloalkyl;

is phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, phenyloxythiocarbonyl, heterocyclyloxycarbonyl, heterocyclyloxythiocarbonyl, phenylaminocarbonyl, N—($C_1$–$C_6$-alkyl)-N-(phenyl)aminocarbonyl, heterocyclylaminocarbonyl, N—($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 18 lastmentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di-($C_1$–$C_6$-alkyl)amino or di-($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

are phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{13}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals selected from the following group:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl; is phenyl, heterocyclyl, phenyl-$C_1$–$C_6$-alkyl or heterocyclyl-$C_1$–$C_6$-alkyl, where the phenyl or heterocyclyl radical of the four lastmentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{14}$ is $C_1$–$C_6$-alkyl, $C_3$–$C_6$-alkenyl, $C_3$–$C_6$-alkynyl or $C_1$–$C_6$-alkylcarbonyl;

q is 0 to 6 and agriculturally useful salts thereof.

2. A cyclohexenonedioxothiochromanoyl derivative of the formula I as defined in claim 1 where $R^9$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)—($C_1$–$C_6$-alkylthio) methyl, hydroxyl, $C_1$–$C_6$-alkoxy, $C_1$–$C_6$-haloalkoxy, $C_1$–$C_6$-alkylthio, $C_1$–$C_6$-halo-alkylthio, $C_1$–$C_6$-alkylsulfinyl, $C_1$–$C_6$-haloalkyl-sulfinyl, $C_1$–$C_6$-alkylsulfonyl, $C_1$–$C_6$-haloalkyl-sulfonyl, $C_1$–$C_6$-alkylcarbonyl, $C_1$–$C_6$-haloalkyl-carbonyl, $C_1$–$C_6$-alkoxycarbonyl or $C_1$–$C_6$-haloalkoxy-carbonyl; or two radicals $R^9$ which are attached to the same carbon together form an —O—($CH_2$)$_m$—O—, —O—($CH_2$)$_m$—S—, —S—($CH_2$)$_m$—S— or —O—($CH_2$)$_n$— chain which may be substituted by one to three radicals selected from the following group:

halogen, cyano, $C_1$–$C_4$-alkyl, $C_1$–$C_4$-haloalkyl or $C_1$–$C_4$-alkoxycarbonyl; or two radicals $R^9$ which are attached to the same carbon form a —($CH_2$)$_p$— chain which may be interrupted by oxygen or sulfur and/or may carry one to four radicals selected from the following group:

halogen, cyano, $C_1$–$C_4$-alkyl, $C_1$–$C_4$-haloalkyl or $C_1$–$C_4$-alkoxycarbonyl; or two radicals $R^9$ which are attached to the same carbon together with this carbon form a carbonyl group.

3. A process for preparing compounds of the formula I as defined in claim 1 where $R^8$=halogen, which comprises reacting a cyclohexanedione derivative of the formula III,

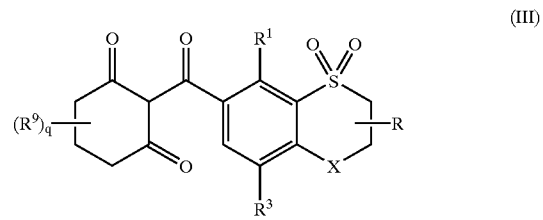

(III)

where the variables $R^1$ to $R^9$, X, l, q are as defined in claim 1 with a halogenating agent.

4. A process for preparing compounds of the formula I as defined in claim 1 where $R^8$=$OR^{10}$, $OSO_2R^{11}$, $OPOR^{11}R^{12}$ or $OPSR^{11}R^{12}$, which comprises reacting a cyclohexanedione derivative of the formula III,

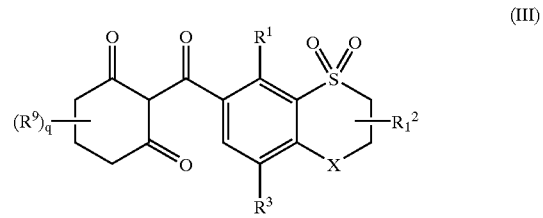

(III)

where the variables $R^1$ to $R^9$, X, l, q are as defined in claim 1 with a compound of the formula IVα, IVβ, IVγ or IVδ, $L^1$—$R^{10}$  (IVα)

$L^1$—$SO_2R^{11}$  (IVβ)

$L^1$—$POR^{11}R^{12}$  (IVγ)

$L^1$—$PSR^{11}R^{12}$  (IVδ)

where the variables $R^{10}$ to $R^{12}$ are as defined in claim 1 and $L^1$ is a nucleophilically replaceable leaving group.

5. A process for preparing compounds of the formula I as defined in claim 1 where $R^8$=$OR^{10}$, $SR^{10}$, $POR^{11}R^{12}$, $NR^{13}R^{14}$, $ONR^{14}R^{14}$, N-bonded heterocyclyl or O(N-bonded heterocyclyl), which comprises reacting a compound of the formula Iα,

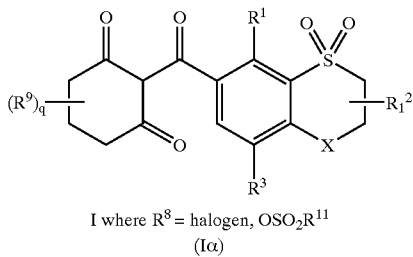

I where R⁸ = halogen, OSO₂R¹¹
(Iα)

where the variables $R^1$ to $R^3$, $R^9$ and $R^{11}$, X, l, q are as defined in claim 1 with a compound of the formula Vα, Vβ, Vγ, Vδ, Vε, Vη or Vθ,

| | |
|---|---|
| HOR¹⁰ | Vα |
| HSR¹⁰ | Vβ |
| HPOR¹¹R¹² | Vγ |
| HNR¹³R¹⁴ | Vδ |
| HONR¹⁴R¹⁴ | Vε | where the variables $R^{10}$ to $R^{14}$ are as defined in claim 1, if appropriate in the presence of a base.

6. A process for preparing compounds of the formula I as defined in claim 1 where $R^8$=SOR¹¹, SO₂R¹¹, which comprises reacting a compound of the formula Iβ,

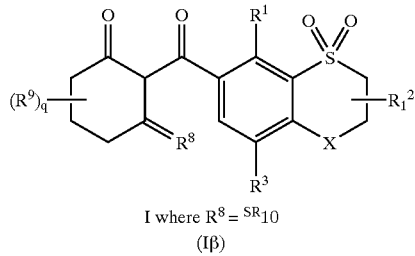

I where R⁸ = SR10
(Iβ)

where the variables $R^1$ to $R^3$, $R^9$, $R^{10}$, X, l, q are as defined in claim 1 with an oxidizing agent.

7. A composition, comprising a herbicidally effective amount of at least one cyclohexenonedioxothiochromanoyl derivative of the formula I or an agriculturally useful salt of I as defined in claim 1, and auxiliaries which are customary for the formulation of crop protection agents.

8. A process for preparing a composition as defined in claim 7, which comprises mixing a herbicidally effective amount of at least one cyclohexenonedioxothiochromanoyl derivative of the formula I or an agriculturally useful salt of I as defined in claim 1 and auxiliaries which are customary for the formulation of crop protection agents.

9. A method for controlling undesirable vegetation, which comprises allowing a herbicidally effective amount of at least one cyclohexenonedioxothiochromanoyl derivative of the formula I or an agriculturally useful salt of I as defined in claim 1 to act on plants, their habitat and/or on seed. comprises allowing a herbicidally effective amount of at least one cyclohexenonedioxothiochromanoyl derivative of the formula I or an agriculturally useful salt of I as defined in claim 1 to act on plants, their habitat and/or on seed. cyclohexenonedioxothiochromanoyl derivatives of the formula I where:

X is oxygen, sulfur, S=O, S(=O)₂, CR⁴R⁵, C=O or C=NR⁶, the other substituents are as defined in the specification, and and agriculturally useful salts thereof; processes for preparing the cyclohexenonedioxothiochromanoyl derivatives; compositions comprising them, and the use of these derivatives or of compositions comprising them for controlling undesirable plants.

* * * * *

UNITED STATES PATENT AND TRADEMARK OFFICE
CERTIFICATE OF CORRECTION

PATENT NO.    : 6,440,899 B1
DATED         : August 27, 2002
INVENTOR(S)   : Witschel et al.

It is certified that error appears in the above-identified patent and that said Letters Patent is hereby corrected as shown below:

<u>Title page,</u>
Item [57], ABSTRACT,
Line 11, "paints" should be -- plants --.

<u>Column 86,</u>
Lines 25 to 42, delete the extra material from "comprises allowing … able plants."

Signed and Sealed this

Fourteenth Day of January, 2003

JAMES E. ROGAN
*Director of the United States Patent and Trademark Office*